United States Patent
Marineau et al.

(10) Patent No.: US 10,336,760 B2
(45) Date of Patent: Jul. 2, 2019

(54) INHIBITORS OF CYCLIN-DEPENDENT KINASE 7 (CDK7)

(71) Applicant: SYROS PHARMACEUTICALS, INC., Cambridge, MA (US)

(72) Inventors: Jason J. Marineau, Franklin, MA (US); Kevin Sprott, Needham, MA (US); Darby Schmidt, Arlington, MA (US)

(73) Assignee: SYROS PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/301,819

(22) PCT Filed: Apr. 3, 2015

(86) PCT No.: PCT/US2015/024336
§ 371 (c)(1),
(2) Date: Oct. 4, 2016

(87) PCT Pub. No.: WO2015/154022
PCT Pub. Date: Oct. 8, 2015

(65) Prior Publication Data
US 2017/0174692 A1  Jun. 22, 2017

Related U.S. Application Data

(60) Provisional application No. 61/975,773, filed on Apr. 5, 2014.

(51) Int. Cl.
| | | |
|---|---|---|
| *A61K 31/53* | (2006.01) | |
| *A61K 31/519* | (2006.01) | |
| *A61K 31/454* | (2006.01) | |
| *A61K 31/4545* | (2006.01) | |
| *A61K 45/06* | (2006.01) | |
| *C07D 417/14* | (2006.01) | |
| *C07D 487/04* | (2006.01) | |

(52) U.S. Cl.
CPC .......... *C07D 487/04* (2013.01); *A61K 31/454* (2013.01); *A61K 31/4545* (2013.01); *A61K 31/519* (2013.01); *A61K 31/53* (2013.01); *A61K 45/06* (2013.01); *C07D 417/14* (2013.01)

(58) Field of Classification Search
CPC .... A61K 31/53; A61K 31/519; A61K 31/454; A61K 31/4545; A61K 45/06; C07D 417/14; C07D 487/04
See application file for complete search history.

(56) References Cited

U.S. PATENT DOCUMENTS

| | | | | |
|---|---|---|---|---|
| 5,571,813 A | | 11/1996 | Ruehter et al. | |
| 6,262,096 B1 * | | 7/2001 | Kim | C07D 231/12 514/369 |
| 6,515,004 B1 * | | 2/2003 | Misra | A61K 31/454 514/369 |
| 6,706,717 B2 * | | 3/2004 | Barrish | C07D 277/46 514/254.02 |
| 8,148,400 B2 * | | 4/2012 | Marinier | C07D 495/04 514/318 |
| 8,343,999 B2 * | | 1/2013 | Marinier | C07D 417/14 514/318 |
| 8,563,741 B2 * | | 10/2013 | Qian | C07D 417/14 544/331 |
| 8,691,820 B2 * | | 4/2014 | Qian | C07D 417/14 514/249 |
| 2008/0221132 A1 * | | 9/2008 | Cai | A61K 47/55 514/263.24 |

FOREIGN PATENT DOCUMENTS

| | | |
|---|---|---|
| EP | 1262828 A1 | 12/2002 |
| WO | 2004022561 A1 | 3/2004 |
| WO | 2004076458 A1 | 9/2004 |
| WO | 2004081013 A1 | 9/2004 |

(Continued)

OTHER PUBLICATIONS

International Search Report and Written Opinion for International Application No. PCT/US2015/024336 dated Sep. 21, 2015.
Shiota et al. "Synthesis and structure-activity relationship of a new series of potent angiotensin II receptor antagonists: pyrazolo [1,5-a] pyrimidine derivatives" Chemical and Pharmaceutical Bulletin (1999) vol. 47 pp. 928-938.
National Center for Biotechnology Information, PubChem Compound Database; CID: 71994675, https://pubchem.ncbi.nlm.gov/compound/71994675, 2013.
Hu et al. "Selective CDK7 inhibitors suppress super enhancer-genes, induce massive apoptosis in acute myeloid leukemia and demonstrate durable in vivo efficacy," American Association for Cancer Research Annual Meeting, 2016.

*Primary Examiner* — Brenda L Coleman
(74) *Attorney, Agent, or Firm* — Goodwin Procter LLP

(57) ABSTRACT

The present invention provides novel compounds described herein, such as of Formula (I), and pharmaceutically acceptable salts, solvates, hydrates, tautomers, stereoisomers, isotopically labeled derivatives, and compositions thereof. Also provided are methods and kits involving the compounds or compositions for treating or preventing proliferative diseases (e.g., cancers (e.g., leukemia, melanoma, multiple myeloma), benign neoplasms, angiogenesis, inflammatory diseases, autoinflammatory diseases, and autoimmune diseases) in a subject. Treatment of a subject with a proliferative disease using a compound or composition of the invention may inhibit the aberrant activity of cyclin-dependent kinase 7 (CDK7), and therefore, induce cellular apoptosis and/or inhibit transcription in the subject.

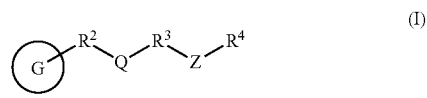

21 Claims, 3 Drawing Sheets

(56) References Cited

FOREIGN PATENT DOCUMENTS

| WO | 2008151304 A1 | 12/2008 |
| WO | 2013074986 A1 | 5/2013 |
| WO | 2013128028 A1 | 9/2013 |
| WO | 2013128029 A1 | 9/2013 |

* cited by examiner

| Patent Compound No. | Structure |
|---|---|
| 121 | 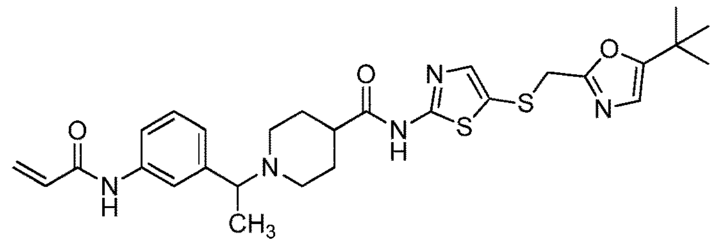 |
| 122 | 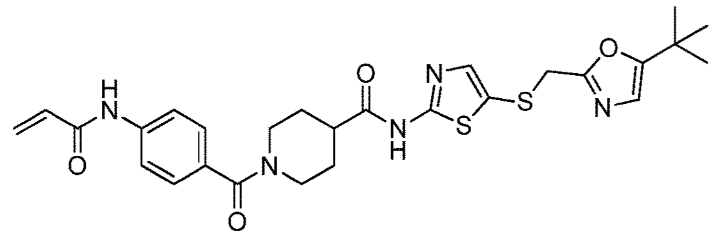 |
| 123 | 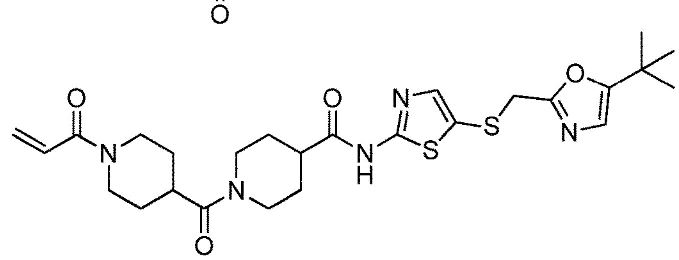 |
| 124 | 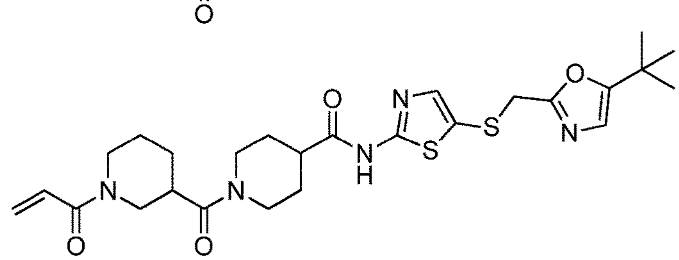 |
| 125 | 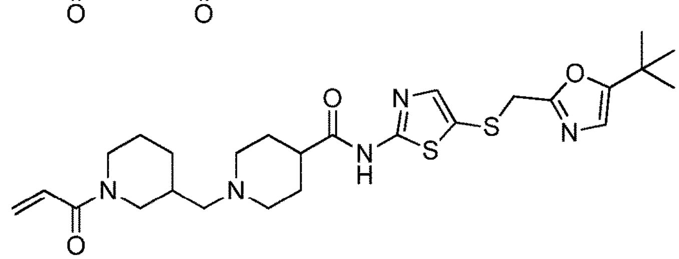 |
| 127 | 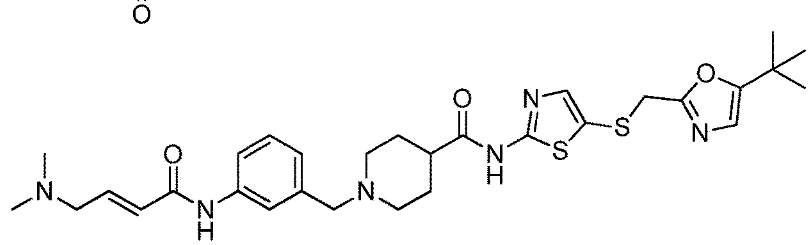 |

INHIBITORS OF CYCLIN-DEPENDENT KINASE 7 (CDK7)

CLAIM OF PRIORITY

The present application is a U.S. National Stage Application under 35 U.S.C. § 371 of International Application No. PCT/US2015/024336, filed Apr. 3, 2015, which claims priority under 35 U.S.C. § 119(e) to U.S. Provisional Application No. 61/975,773, filed Apr. 5, 2014. The entire contents of each of the foregoing applications are incorporated herein by reference.

BACKGROUND OF THE INVENTION

The members of the cyclin-dependent kinase (CDK) family play critical regulatory roles in proliferation. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression. In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation Together, the two functions of CDK7, i.e., CAK and CTD phosphorylation, support critical facets of cellular proliferation, cell cycling, and transcription.

Disruption of RNAP II CTD phosphorylation has been shown to preferentially affect proteins with short half-lives, including those of the anti-apoptotic BCL-2 family. Cancer cells have demonstrated ability to circumvent pro-cell death signaling through upregulation of BCL-2 family members. Therefore, inhibition of human CDK7 kinase activity is likely to result in anti-proliferative activity.

The discovery of selective inhibitors of CDK7 has been hampered by the high sequence and structural similarities of the kinase domain of CDK family members. Therefore, there is a need for the discovery and development of selective CDK7 inhibitors. Such CKD7 inhibitors hold promise as a therapeutic agent for the treatment of CLL and other cancers.

SUMMARY OF THE INVENTION

Figure 1A:
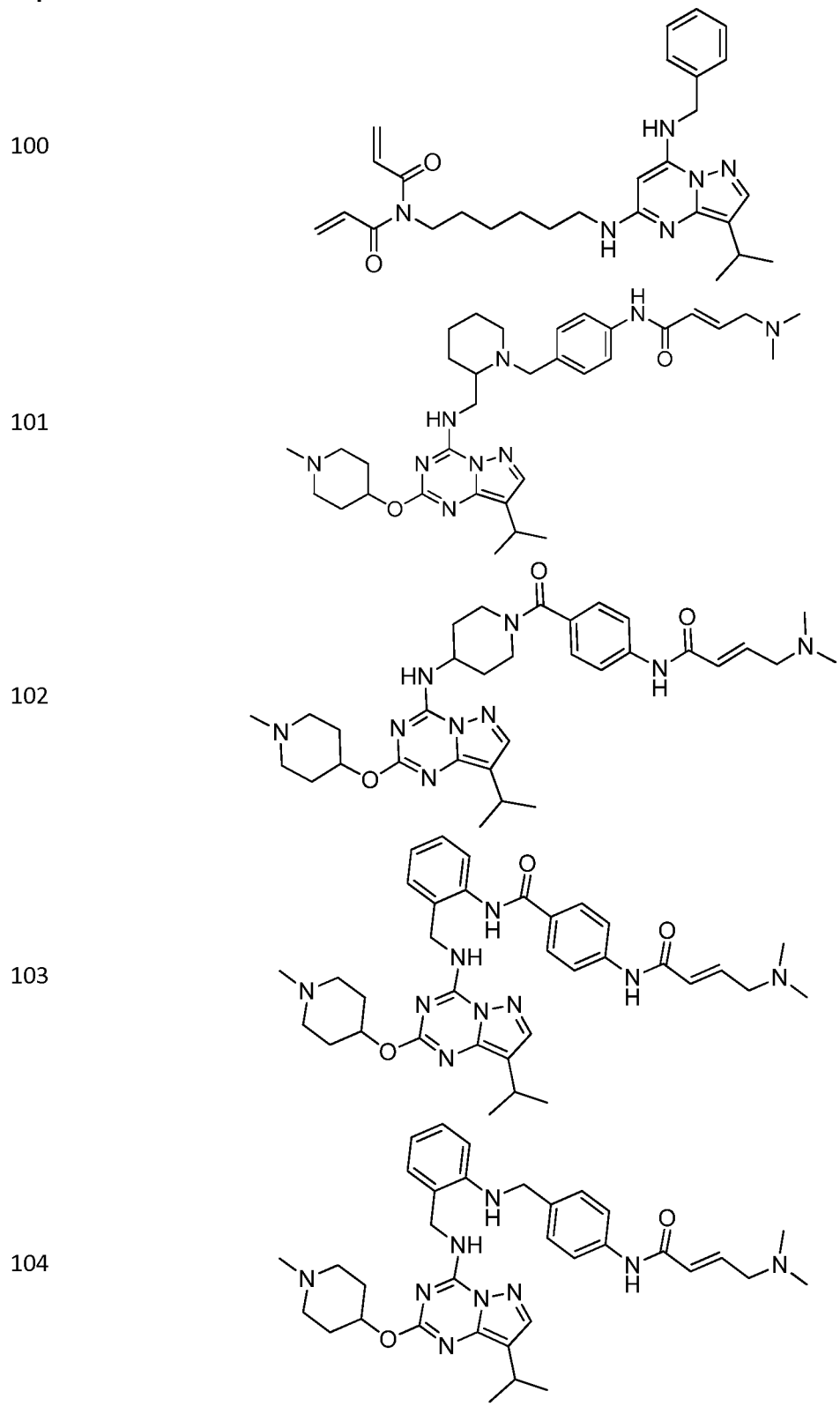
FIGS. 1A-1C are a table of exemplary compounds of the invention.

The present invention provides inhibitors of one or more of the family of CDK proteins. The present invention further provides CDK7 inhibitors, in particular selective CDK7 inhibitors of Formula (I), and pharmaceutically acceptable salts, solvates, hydrates, tautomers, stereoisomers, isotopically labeled derivatives, and compositions thereof. The present invention further provides methods of using the compounds of the invention, and pharmaceutically acceptable salts, solvates, hydrates, tautomers, stereoisomers, isotopically labeled derivatives, and compositions thereof, to study the inhibition of CDK7 and CDK12 and/or CDK13 as therapeutics for the prevention and/or treatment of diseases associated with overexpression and/or aberrant activity of CDK7 and/or CDK12 and/or CDK13. In certain embodiments, the inventive compounds are used for the prevention and/or treatment of proliferative diseases (e.g., cancers (e.g., leukemia, melanoma, multiple myeloma), benign neoplasms, angiogenesis, inflammatory diseases, autoinflammatory diseases, and autoimmune diseases) in a subject.

In one aspect, the present invention provides a compound described herein, such as of Formula (I):

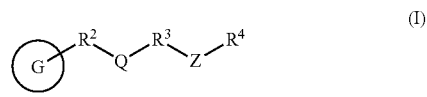

or a pharmaceutically acceptable salt, solvate, hydrate, tautomer, or stereoisomer thereof, wherein G, $R^2$, Q, $R^3$, Z, and $R^4$ and subvariables thereof are as defined herein.

In another aspect, the present invention provides pharmaceutical compositions comprising a compound described herein, such as of Formula (I), or a pharmaceutically acceptable salt, solvate, hydrate, tautomer, stereoisomer, or isotopically labeled derivative thereof, and optionally a pharmaceutically acceptable excipient. In certain embodiments, the pharmaceutical compositions described herein include a therapeutically effective amount of a compound described herein, such as of Formula (I), or a pharmaceutically acceptable salt, solvate, hydrate, tautomer, stereoisomer, or isotopically labeled derivative thereof. The pharmaceutical composition may be useful for treating and/or preventing a proliferative or infectious disease.

In another aspect, the present invention provides methods for treating and/or preventing proliferative diseases. Exemplary proliferative diseases include cancer (e.g., leukemia, melanoma, multiple myeloma), benign neoplasm, angiogenesis, inflammatory diseases, autoinflammatory diseases, and autoimmune diseases. In other embodiments, the present invention provides methods for treating and/or preventing an infectious disease (e.g., a viral infection).

In still another aspect, the present invention provides methods of down-regulating the expression of CDK7 in a biological sample or subject.

Another aspect of the invention relates to methods of inhibiting the activity of CDK7 in a biological sample or subject.

The present invention also provides methods of inhibiting cell growth in a biological sample or subject.

In still another aspect, the present invention provides methods of inducing apoptosis of a cell in a biological sample or a subject.

In yet another aspect, the present invention provides compounds described herein, such as of Formula (I), and pharmaceutically acceptable salts, solvates, hydrates, tautomers, stereoisomers, isotopically labeled derivatives, and compositions thereof, for use in the treatment of a proliferative disease in a subject.

In yet another aspect, the present invention provides compounds described herein, such as of Formula (I), and pharmaceutically acceptable salts, solvates, hydrates, tautomers, stereoisomers, isotopically labeled derivatives, and compositions thereof, for use in the treatment or prevention of an infectious disease in a subject. In certain embodiments, the infectious disease is a viral infection.

Another aspect of the present invention relates to kits comprising a container with a compound described herein, such as of Formula (I), or a pharmaceutically acceptable salt, solvate, hydrate, tautomer, stereoisomer, or isotopically labeled derivative thereof, or a pharmaceutical composition thereof. In certain embodiments, the kits described herein further include instructions for administering the compound described herein, such as of Formula (I), or the pharmaceutically acceptable salt, solvate, hydrate, tautomer, stereoisomer, or isotopically labeled derivative thereof, or the pharmaceutical composition thereof.

In still another aspect, the present invention provides methods of inhibiting other CDKs, specifically CDK12 and/or CDK13, with a compound described herein, such as of Formula (I), or a pharmaceutically acceptable salt, solvate, hydrate, tautomer, or stereoisomer, or a pharmaceutical composition thereof.

The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl. Aliphatic groups may be optionally substituted, e.g., as described herein.

The term "alkyl," as used herein, refers to a monovalent saturated, straight- or branched-chain hydrocarbon such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Alkyl groups may be optionally substituted, e.g., as described herein. Examples of alkyl groups include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, and the like. An alkyl may be optionally substituted, e.g., as described herein.

The terms "alkenyl" and "alkynyl" are art-recognized and refer to unsaturated aliphatic groups analogous in length and possible substitution to the alkyls described above, but that contain at least one double or triple bond, respectively. Exemplary alkenyl groups include, but are not limited to, —CH=CH$_2$ and —CH$_2$CH=CH$_2$.

The term "alkylene" refers to the diradical of an alkyl group.

The terms "alkenylene" and "alkynylene" refer to the diradicals of an alkenyl and an alkynyl group, respectively.

The term "methylene unit" refers to a divalent —CH$_2$— group present in an alkyl, alkenyl, alkynyl, alkylene, alkenylene, or alkynylene moiety.

The term "carbocyclic ring system", as used herein, means a monocyclic, or fused, spiro-fused, and/or bridged bicyclic or polycyclic hydrocarbon ring system, wherein each ring is either completely saturated or contains one or more units of unsaturation, but where no ring is aromatic.

The term "carbocyclyl" refers to a radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like). A carbocyclyl may be optionally substituted, e.g., as described herein.

The term "aromatic ring system" is art-recognized and refers to a monocyclic, bicyclic or polycyclic hydrocarbon ring system, wherein at least one ring is aromatic.

The term "aryl" refers to a radical of an aromatic ring system. Representative aryl groups include fully aromatic ring systems, such as phenyl, naphthyl, and anthracenyl, and ring systems where an aromatic carbon ring is fused to one or more non-aromatic carbon rings, such as indanyl, phthalimidyl, naphthimidyl, or tetrahydronaphthyl, and the like. An aryl may be optionally substituted, e.g., as described herein.

The term "heteroaromatic ring system" is art-recognized and refers to monocyclic, bicyclic or polycyclic ring system wherein at least one ring is both aromatic and comprises a heteroatom; and wherein no other rings are heterocyclyl (as defined below). In certain instances, a ring which is aromatic and comprises a heteroatom contains 1, 2, 3, or 4 independently selected ring heteroatoms in such ring.

The term "heteroaryl" refers to a radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl. In certain embodiments, the heteroaryl is a monocyclic or bicyclic ring, wherein each of said rings contains 5 or 6 ring atoms where 1, 2, 3, or 4 of said ring atoms are a heteroatom independently selected from N, O, and S. A heteroaryl may be optionally substituted, e.g., as described herein.

The term "heterocyclic ring system" refers to monocyclic, or fused, spiro-fused, and/or bridged bicyclic and polycyclic ring systems where at least one ring is saturated or partially unsaturated (but not aromatic) and comprises a heteroatom. A heterocyclic ring system can be attached to its pendant group at any heteroatom or carbon atom that results in a stable structure and any of the ring atoms can be optionally substituted.

The term "heterocyclyl" refers to a radical of a heterocyclic ring system. Representative heterocyclyls include ring systems in which (i) every ring is non-aromatic and at least one ring comprises a heteroatom, e.g., tetrahydrofuranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine. In certain embodiments, the heterocyclyl is a monocyclic or bicyclic ring, wherein each of said rings contains 3-7 ring atoms where 1, 2, 3, or 4 of said ring atoms are a heteroatom independently selected from N, O, and S. A heterocyclyl may be optionally substituted, e.g., as described herein.

The term "saturated heterocyclyl" refers to a radical of heterocyclic ring system wherein every ring is saturated, e.g., tetrahydrofuran, tetrahydro-2H-pyran, pyrrolidine, piperidine and piperazine.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group (such as an alkyl, alkenyl, alkynyl, alkylene, alkenylene, alkynylene or the carbon atom of a carbocyclyl, aryl, heterocyclyl or heteroaryl) are independently deuterium; halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph (where "Ph" is phenyl), which may be substituted with R°; —(CH$_2$)$_{0-4}$O(CH$_2$)$_{0-1}$Ph which may be substituted with R°; —CH=CHPh, which may be substituted with —R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$—C(O)—N(R°)—S(O)$_2$—R°, —(CH$_2$)$_{0-4}$OC(O)R°; —OC(O)(CH$_2$)$_{0-4}$SR°—, —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)R°; —C(O)C(O)R°; —C(O)CH$_2$C(O)R; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, deuterium, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently deuterium, halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include deuterium, halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently deuterium, halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

"Halo" or "halogen" refers to fluorine (fluoro, —F), chlorine (chloro, —Cl), bromine (bromo, —Br), or iodine (iodo, —I).

The term "one or more methylene units of the alkylene, alkenylene or alkynylene is optionally replaced with —O—, —S—, —S(=O)$_2$, or —NR$^X$—" as used herein means that none, one, more than one, or all of the methylene units present may be so replaced. Thus, for example, the moieties, —O—, —S—, and —NR$^X$— are included in this definition because in each case they represent a C$_1$ alkylene (i.e., methylene) replaced with —O—, —S—, or —NR$^X$—, respectively.

It should also be understood that reference to a variable or subvariable in Formula I (e.g., R$^2$, R$^3$, or R$^4$) being "an optionally substituted C$_1$-C$_4$ alkylene, and an optionally substituted C$_2$-C$_4$ alkenylene or alkynylene, wherein: one or more methylene units of the alkylene, alkenylene or alkynylene other than a methylene unit bound to a nitrogen atom is optionally and independently replaced with —O—, —S—, —N(R$^6$)—, —NHC(O)—, —C(O)NH—, —C(O)—, or —S(=O)$_2$—" is only intended to encompass chemically stable combinations of optionally substitutions and replacements.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

These and other exemplary substituents are described in more detail in the Detailed Description, Figures, Examples, and Claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein, such as of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat," and "treating" require that signs or symptoms of the disease disorder or condition have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

An "effective amount" of a compound described herein, such as of Formula (I) refers to an amount sufficient to elicit the desired biological response, i.e., treating the condition. As will be appreciated by those of ordinary skill in this art, the effective amount of a compound described herein, such as of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound described herein, such as of Formula (I) is an amount sufficient to provide a therapeutic benefit in the treatment of a condition or to delay or minimize one or more symptoms associated with the condition. In some embodiments, a therapeutically effective amount is an amount sufficient to provide a therapeutic benefit in the treatment of a condition or to minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound described herein, such as of Formula (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

As used herein, the term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases).

As used herein, an "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "autoinflammatory disease" refers to a category of diseases that are similar but different from autoimmune diseases. Autoinflammatory and autoimmune diseases share common characteristics in that both groups of disorders result from the immune system attacking a subject's own tissues and result in increased inflammation. In autoinflammatory diseases, a subject's innate immune system causes inflammation for unknown reasons. The innate immune system reacts even though it has never encountered autoantibodies or antigens in the subject. Autoinflammatory disorders are characterized by intense episodes of inflammation that result in such symptoms as fever, rash, or joint swelling. These diseases also carry the risk of amyloidosis, a potentially fatal buildup of a blood protein in vital organs. Autoinflammatory diseases include, but are not limited to, familial Mediterranean fever (FMF), neonatal onset multisystem inflammatory disease (NOMID), tumor necrosis factor (TNF) receptor-associated periodic syndrome (TRAPS), deficiency of the interleukin-1 receptor antagonist (DIRA), and Behçet's disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as transgenic oocyte, sperm cell, blastocyst, embryo, fetus, donor cell, or cell nucleus.

DETAILED DESCRIPTION OF CERTAIN EMBODIMENTS OF THE INVENTION

Compounds

In one aspect of the present invention, provided are compounds described herein, such as of Formula (I): compound having the structural Formula (I):

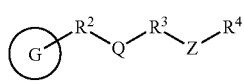

(I)

or a pharmaceutically acceptable salt, solvate, hydrate, tautomer, or stereoisomer thereof, wherein G is selected from:

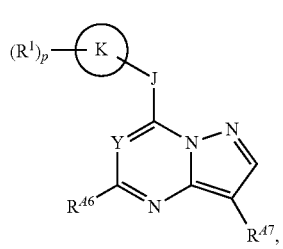

(II)

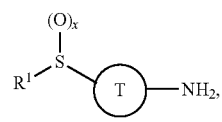

(III)

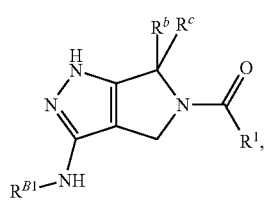

(IV)

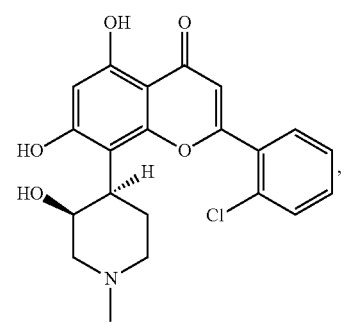

(V)

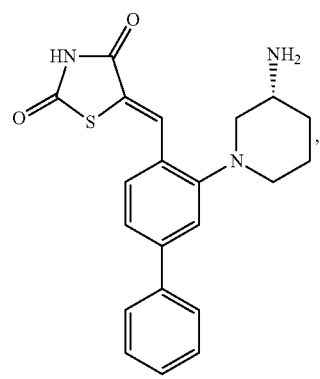

(VI)

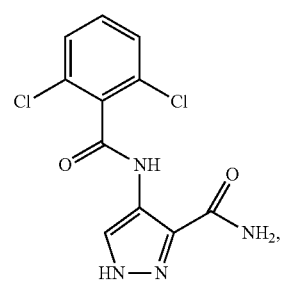

(VII)

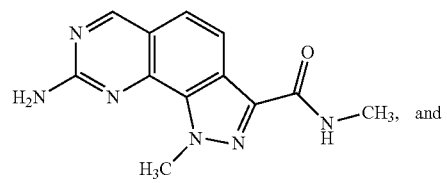

(VIII)

and

-continued

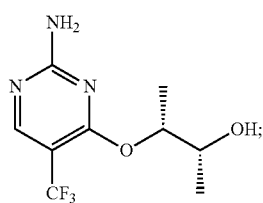
(IX)

wherein a hydrogen on G is replaced by a bond to $R^2$, and each $R^1$ is independently selected from hydrogen, halogen, heterocyclyl, aryl, heteroaryl, optionally substituted $C_1$-$C_6$ alkyl, carbocyclyl, —$OR^a$, —$NR^bR^c$, —$C(O)R^a$, —$C(O)NR^bR^c$, —$S(O)_xR^a$, and —$S(O)_xNR^bR^c$; $R^{46}$ is hydrogen, halogen, heterocyclyl, $C_1$-$C_6$ alkyl, carbocyclyl, —$OR^a$, —$NR^bR^c$, —$C(O)R^a$, —$C(O)NR^bR^c$, —$S(O)_xR^a$, or —$S(O)_xNR^bR^c$; $R^{47}$ is hydrogen, halogen, heterocyclyl, $C_1$-$C_6$ alkyl, carbocyclyl, —$OR^a$, —$NR^bR^c$, —$C(O)R^a$, —$C(O)NR^bR^c$, —$S(O)_xR^a$, or —$S(O)_xNR^bR^c$; each $R^a$ is independently selected from hydrogen, $C_1$-$C_6$ alkyl, optionally substituted aryl, optionally substituted heteroaryl, and optionally substituted heterocyclyl; each $R^b$ and $R^c$ is independently selected from hydrogen and —$C_1$-$C_6$ alkyl, or $R^b$ and $R^c$ taken together with the atom to which they are attached form a 3-7-membered ring; Y is N or CH; K is bond, aryl, heteroaryl, carbocyclyl, or heterocyclyl; J is —NH— or —O—; T is a 5-membered aryl or heteroaryl; p is 0, 1, 2, 3, 4, or 5; x is 0, 1, or 2; $R^2$ is a bond, an optionally substituted $C_1$-$C_4$ alkylene or an optionally substituted $C_2$-$C_4$ alkenylene or alkynylene, wherein one or more methylene units of the alkylene, alkenylene or alkynylene are optionally and independently replaced with —O—, —S—, —C(O)—, or —N($R^6$)—, wherein $R^6$ is hydrogen or a $C_1$-$C_6$ alkyl chain, and $Alk^1$ is an optionally substituted divalent hydrocarbyl chain containing from 1 to 6 carbon atoms in length and optionally unsaturated bonds between at least two carbon atoms of $Alk^1$ when $Alk^1$ contains at least two carbon atoms; Q is selected from a bond, an optionally substituted divalent carbocyclyl, an optionally substituted divalent heterocyclyl, an optionally substituted divalent aryl, and an optionally substituted divalent heteroaryl; $R^3$ is selected from a bond, an optionally substituted $C_1$-$C_4$ alkylene, and an optionally substituted $C_2$-$C_4$ alkenylene or alkynylene, wherein one or more methylene units of the alkylene, alkenylene or alkynylene is optionally and independently replaced with —O—, —S—, —N($R^6$)—, —NHC(O)—, —C(O)NH—, —C(O)—, or —S(=O)$_2$—; each $R^6$ is independently selected from hydrogen and optionally substituted —$C_1$-$C_6$ alkyl; Z is selected from a bond; a monocyclic or bicyclic aryl, carbocyclyl, heterocyclyl or heteroaryl, wherein when Z is other than a bond, Z is optionally substituted; $R^4$ is any one of the Formulae (ii-0)-(ii-19):

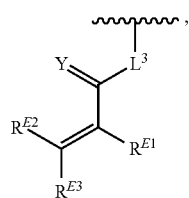
(ii-1)

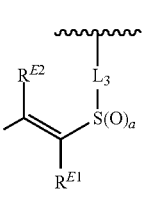
(ii-2)

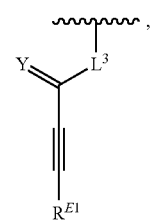
(ii-3)

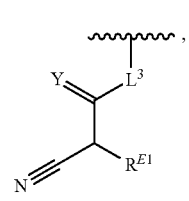
(ii-4)

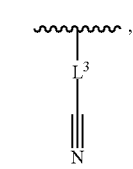
(ii-5)

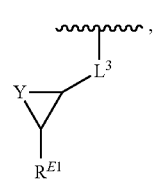
(ii-6)

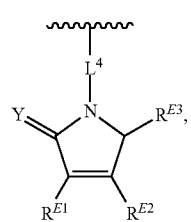
(ii-7)

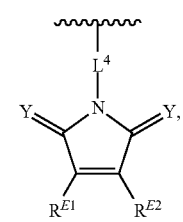
(ii-8)

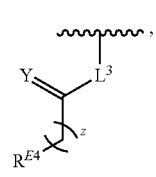
(ii-9)

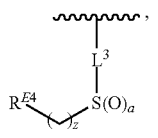 (ii-10)

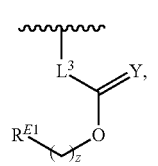 (ii-11)

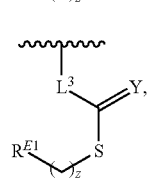 (ii-12)

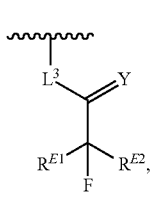 (ii-13)

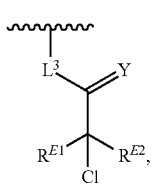 (ii-14)

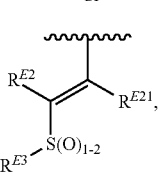 (ii-15)

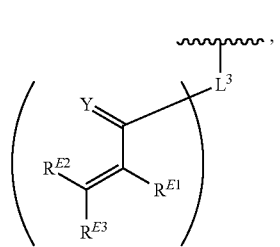 (ii-0)

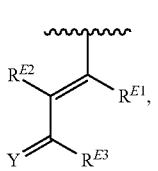 (ii-16)

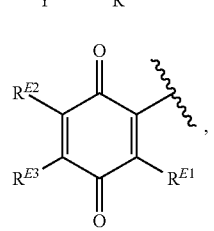 (ii-17)

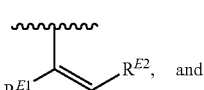 (ii-18), and

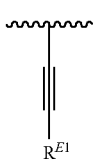 (ii-19)

wherein: $L^3$ is a bond, an optionally substituted $C_1$-$C_7$ alkylene, or an optionally substituted $C_2$-$C_7$ alkenylene or alkynylene, wherein one or more methylene units of the alkylene, alkenylene or alkynylene are optionally and independently replaced with —O—, —S—, —S(O)—, —S(O)$_2$, —N—, or —N(R$^6$)—; $L^4$ is a bond, an optionally substituted $C_1$-$C_4$ alkylene, or an optionally substituted $C_2$-$C_4$ alkenylene or alkynylene; each of $R^{E1}$, $R^{E2}$ and $R^{E3}$ is independently selected from hydrogen, deuterium, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^9$, —CH$_2$N(R$^9$)$_2$, —CH$_2$SR$^9$, —CN, —OR$^9$, —N(R$^9$)$_2$, and —SR$^9$, wherein each occurrence of $R^9$ is independently selected from hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or $R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring; $R^{E4}$ is a leaving group; Y is O, S, or N(R$^6$); and z is 0, 1, 2, 3, 4, 5, or 6; when Q is phenyl, Z is other than a bond; and except in the case wherein $R^4$ is (ii-0), no more than one of Q, $R^3$, and Z is a bond.

In some embodiments, the compound of formula (I) is a compound having the structural formula (IIb):

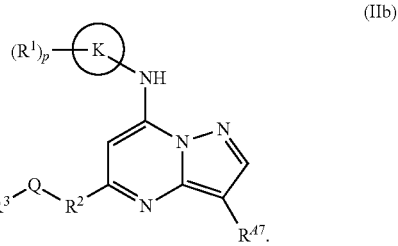 (IIb)

In some aspects of these embodiments, the compound of formula (IIb) is the compound:

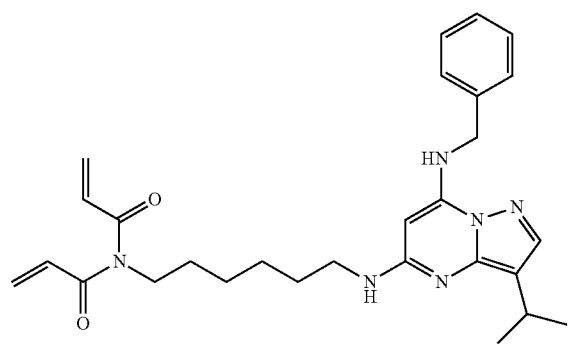

In some embodiments, the compound of formula (I) is a compound having the structural formula (IIc):

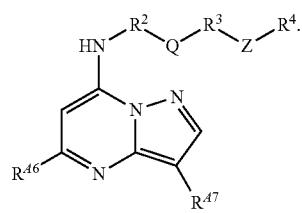

(IIc)

In some embodiments, the compound of formula (I) is a compound having the structural formula (IId):

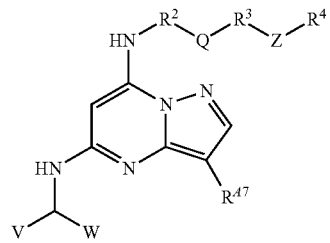

(IId)

wherein V is hydrogen, halogen, heterocyclyl, aryl, heteroaryl, $C_1$-$C_6$ alkyl, carbocyclyl, —$OR^a$, —$NR^bR^c$, —$S(O)_xR^a$, —$S(O)_xNR^bR^c$; and W is hydrogen, halogen, heterocyclyl, aryl, heteroaryl, $C_1$-$C_6$ alkyl, carbocyclyl, —$OR^a$, —$NR^bR^c$, —$S(O)_xR^a$, —$S(O)_xNR^bR^c$.

In some aspects of these embodiments, the compound of formula (IId) is a compound having the structural formula (IIe):

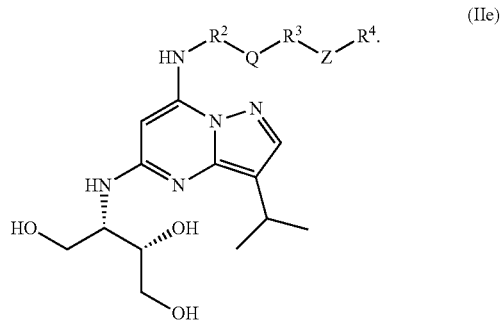

(IIe)

In some aspects of these embodiments, the compound of formula (IId) is a compound having the structural formula (IIf):

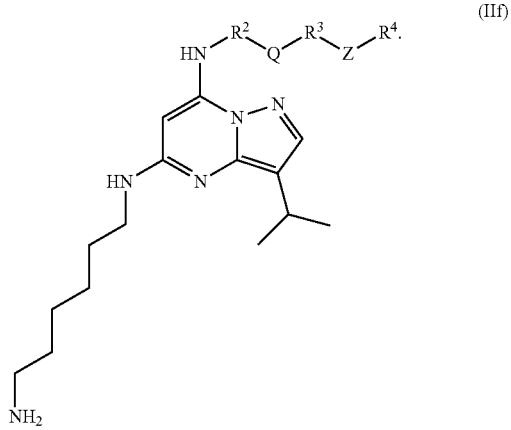

(IIf)

In some embodiments, the compound of formula (I) is a compound having the structural formula (IIg):

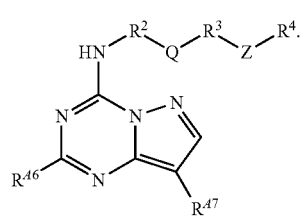

(IIg)

In some aspects of these embodiments, the compound of formula (IIg) is a compound having the structural formula (IIh):

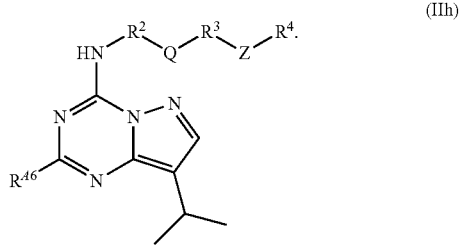

(IIh)

In some aspects of these embodiments, the compound of formula (IIh) is a compound having the structural formula (IIi):

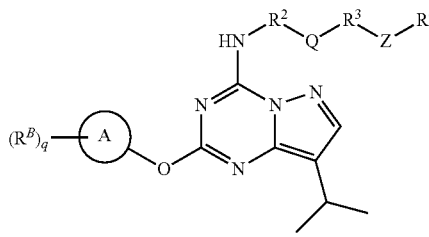

(IIi)

wherein A is optionally substituted aryl, optionally substituted heterocyclyl, or optionally substituted heteroaryl; $R^B$ is $C_1$-$C_6$ alkyl or halogen; and q is 0, 1, 2, or 3.

In some aspects of these embodiments, the compound of formula (IIi) is a compound having the structural formula (IIj):

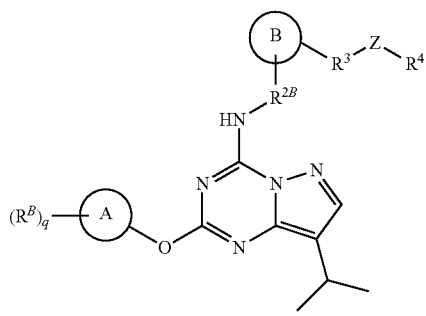

(IIj)

wherein $R^{2B}$ is a bond or optionally substituted —$CH_2$; and B is optionally substituted divalent aryl, optionally substituted divalent heteroaryl, or optionally substituted divalent heterocyclyl.

In some aspects of these embodiments, the compound of formula (IIj) is the compound

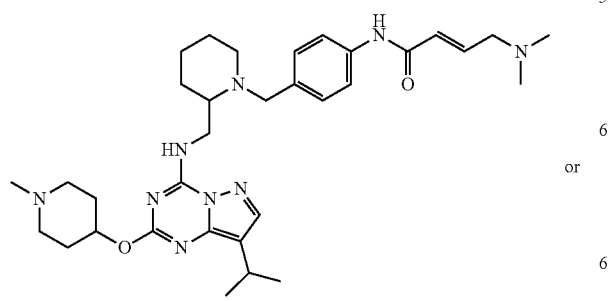

or

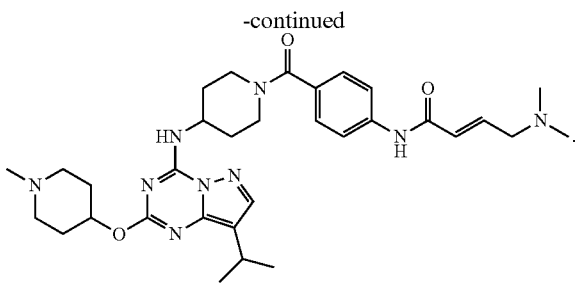

In some aspects of these embodiments, the compound of formula (IIj) is a compound having the structural formula (IIk):

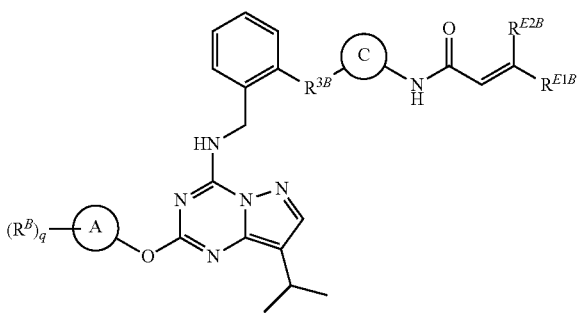

(IIk)

wherein A is optionally substituted aryl, optionally substituted heterocyclyl, or optionally substituted heteroaryl; C is optionally substituted monocyclic aryl, optionally substituted monocyclic heteroaryl, or optionally substituted monocyclic heterocyclyl; $R^B$ is $C_1$-$C_6$ alkyl or halogen; $R^{3B}$ is a bond, optionally substituted —NHC(O)—, optionally substituted —$CH_2$—, optionally substituted —NH—, optionally substituted —$NHCH_2$—, or optionally substituted —$CH_2NH$—; each of $R^{E1B}$ and $R^{E2B}$ is independently selected from hydrogen or —$CH_2N(CH_3)_2$; and q is 0, 1, 2, or 3.

In some aspects of these embodiments, the compound of formula (IIk) is a compound having the structural formula (IIm):

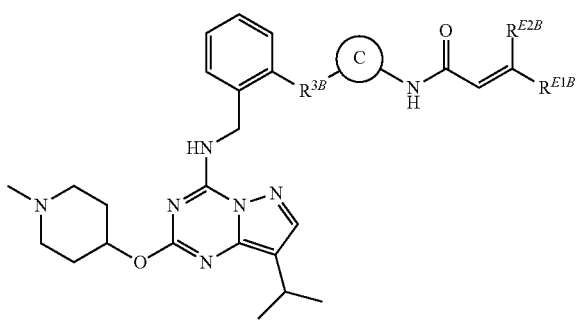

(IIm)

wherein C is optionally substituted monocyclic aryl, optionally substituted monocyclic heteroaryl, or optionally substituted monocyclic heterocyclyl; $R^{3B}$ is a bond, optionally substituted —NHC(O)—, optionally substituted —CH$_2$—, optionally substituted —NH—, optionally substituted —NHCH$_2$—, or optionally substituted —CH$_2$NH—; and each of R$^{E1B}$ and R$^{E2B}$ is independently selected from hydrogen or —CH$_2$N(CH$_3$)$_2$.

In some aspects of these embodiments, the compound of formula (IIm) is the compound:

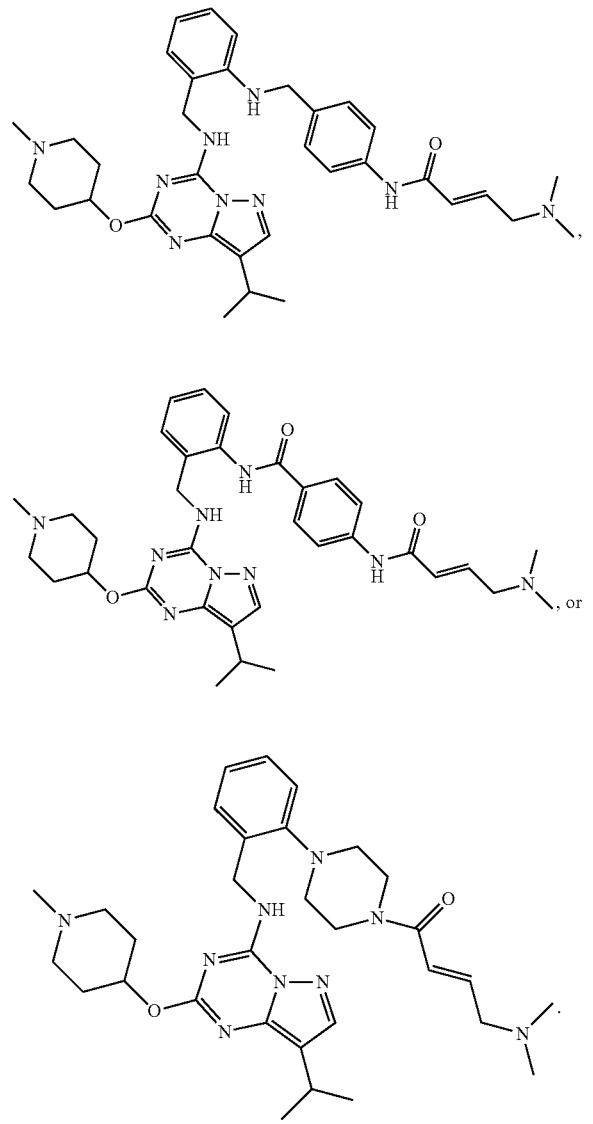

In some embodiments, the compound of formula (I) is a compound having the structural formula (IIIa):

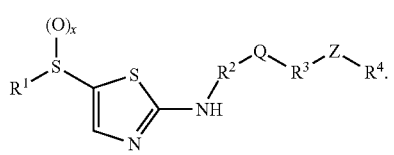

(IIIa)

In some aspects of these embodiments, the compound of formula (IIIa) is a compound having the structural formula (IIIb):

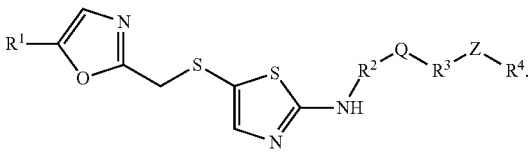

(IIIb)

In some aspects of these embodiments, the compound of formula (IIIb) is a compound having the structural formula (IIIc):

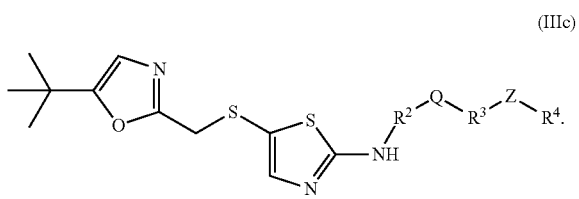

(IIIc)

In some aspects of these embodiments, the compound of formula (IIIc) is the compound:

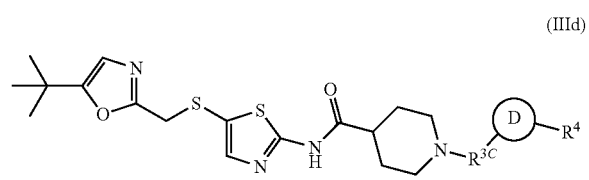

In some aspects of these embodiments, the compound of formula (IIIc) is a compound having the structural formula (IIId):

(IIId)

wherein R$^{3C}$ is a bond, optionally substituted —CH$_2$—, optionally substituted —NH—, —C(O), —N(CH$_3$)—, or optionally substituted —CH(CH$_3$)—; and D is optionally substituted monocyclic or bicyclic aryl or heteroaryl.

In some aspects of these embodiments, the compound of formula (IIId) is the compound:

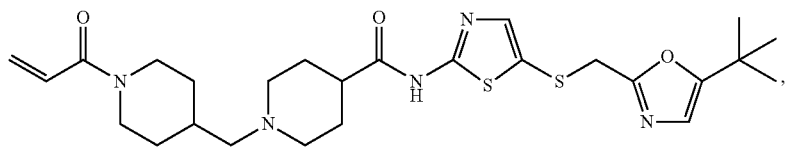
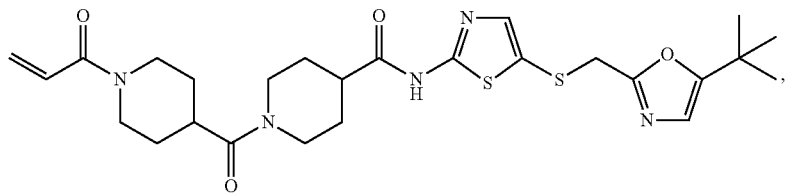
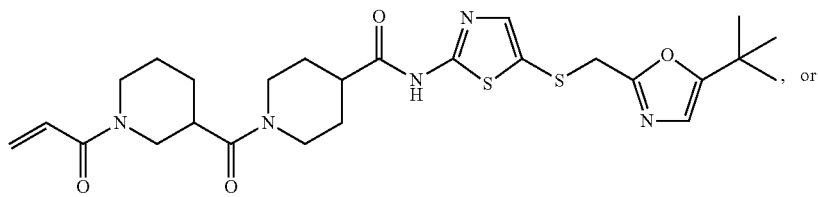
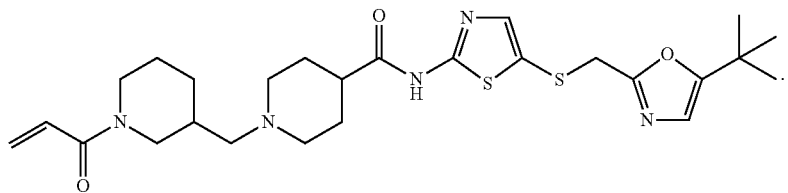
In some aspects of these embodiments, the compound of formula (IIId) is a compound having the structural formula (IIIe):
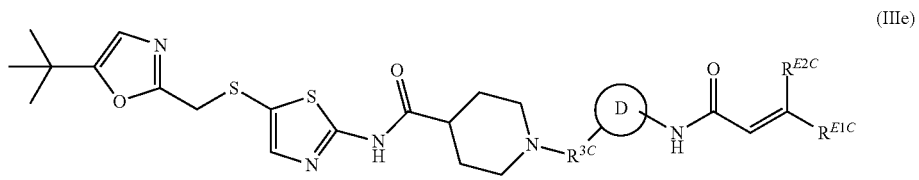
wherein each of $R^{E1C}$ and $R^{E2C}$ is independently selected from hydrogen or —CH$_2$N(CH$_3$)$_2$.
In some aspects of these embodiments, the compound of formula (IIIe) is the compound:
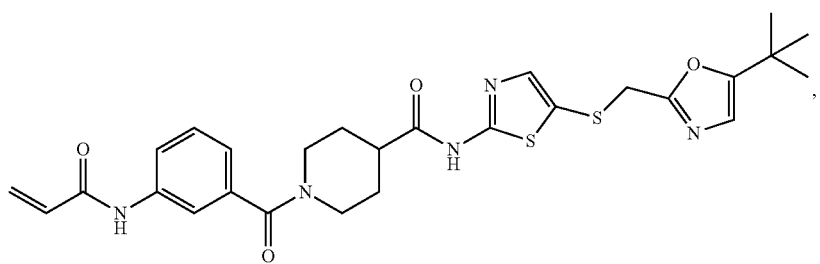

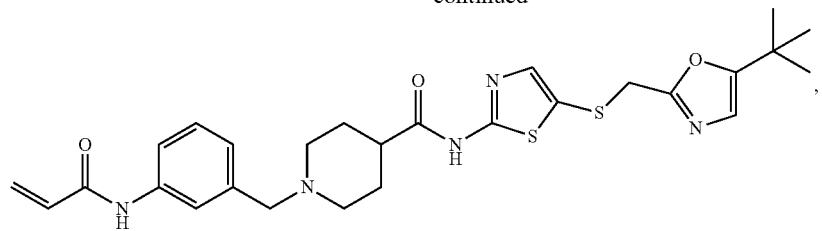
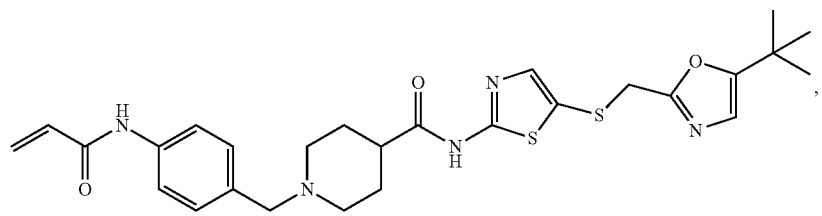
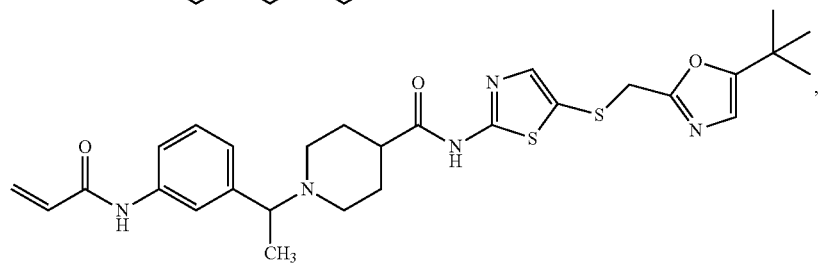
, or
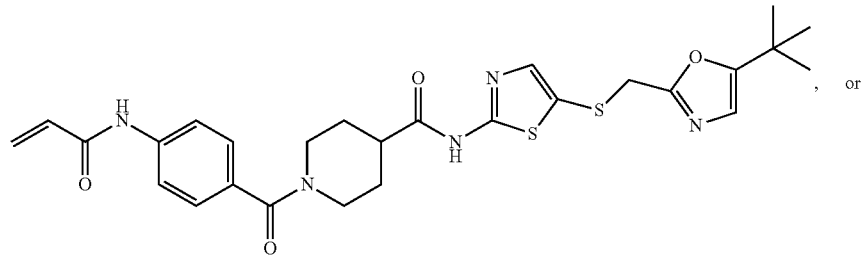
.
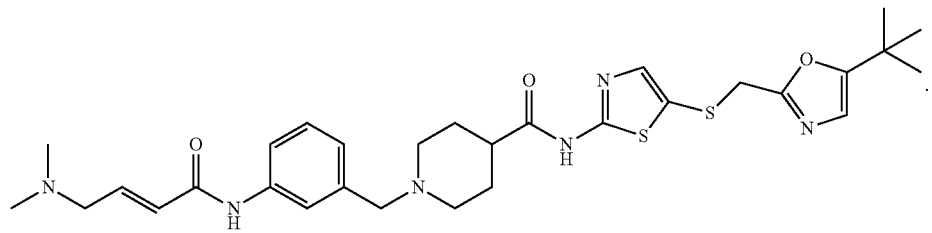
In some embodiments, the compound of formula (I) is a compound having the structural formula (IVa):
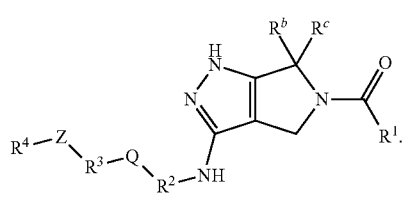
(IVa)
In some aspects of these embodiments, the compound of formula (IVa) is a compound having the structural formula (IVb):
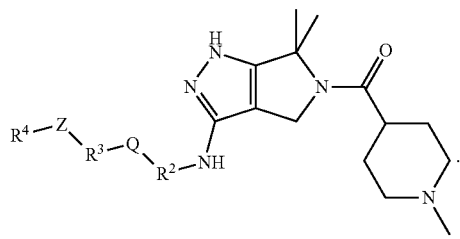
(IVb)
In some embodiments, the compound of formula (I) is a compound having the structural formula (Va):

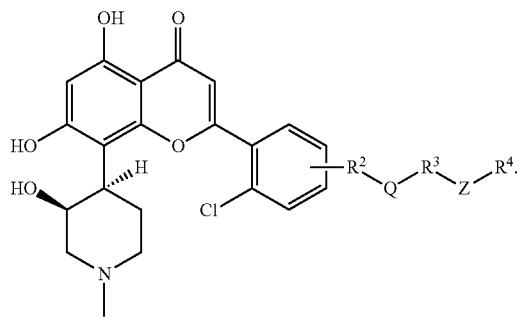

(Va)

In some aspects of these embodiments, the compound of formula (Va) is a compound having the structural formula (VIa):

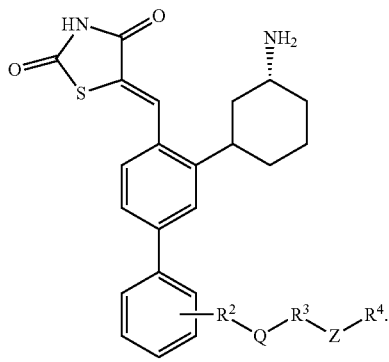

(VIa)

In some embodiments, the compound of formula (I) is a compound having the structural formula (VIIa):

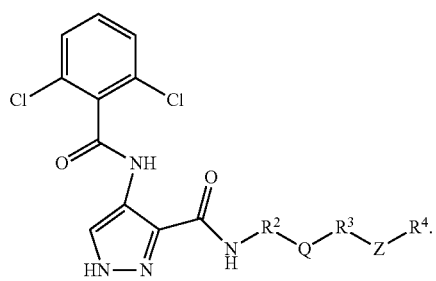

(VIIa)

In some embodiments, the compound of formula (I) is a compound having the structural formula (VIIIa):

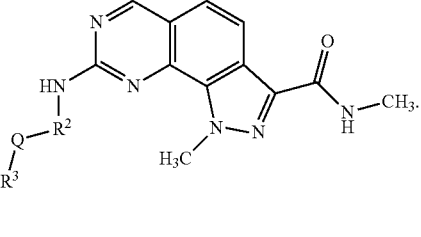

(VIIIa)

In some embodiments, the compound of formula (I) is a compound having the structural formula (IXa):

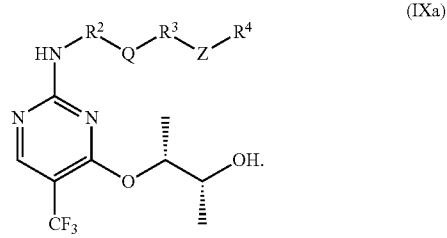

(IXa)

In some embodiments, $R^2$ is a bond, an optionally substituted $C_1$-$C_4$ alkylene or an optionally substituted $C_2$-$C_4$ alkenylene or alkynylene, wherein one or more methylene units of the alkylene, alkenylene or alkynylene are optionally and independently replaced with —O—, —S—, —C(O)—, or —N($R^6$)—, wherein $R^6$ is hydrogen or a $C_1$-$C_6$ alkyl chain. In some embodiments, $R^6$ does not comprise $Alk^1$.

In some embodiments, $R^2$ is selected from a bond, †-NH—, †-C(O), †-CH$_2$—, and †-NHC(O)—, wherein "†" represents a portion of $R^2$ bound to G. In some embodiments, In some embodiments, Q is selected from a bond, divalent 1,3,4-oxadiazole; divalent 1-oxa-3-azaspiro[4.5]dec-2-ene; divalent cyclohexyl; divalent 4-thia-1,2-diazaspiro[4.5]dec-2-ene; divalent oxazole; divalent phenyl; divalent piperidine and divalent pyrrolidine, wherein Q is optionally substituted with up to three independently selected substituents.

In some aspects of these embodiments, Q is selected from 1,3,4-oxadiazol-2,5-diyl; 1-oxa-3-azaspiro[4.5]dec-2-en-7,2-diyl; 4-fluorocyclohex-1,4-diyl; 4-hydroxycyclohex-1,4-diyl; 4-thia-1,2-diazaspiro[4.5]dec-2-en-7,3-diyl; cyclohex-1,3-diyl; cyclohex-1,4-diyl; oxazol-2,5-diyl; benzene-1,2-diyl; benzene-1,3-diyl; benzene-1,2,3-triyl; piperidin-1,3-diyl; piperidin-1,3-diyl; piperidin-4,1-diyl; piperidin-1,4-diyl; and pyrrolidin-3,1-diyl.

In some embodiments, $R^3$ is selected from a bond, †-C(O)—(CH$_2$)$_3$—, †-CH$_2$CH$_2$CH$_2$CH$_2$CH$_2$CH$_2$—, †-C(O)—, †-C(O)—NH—, †-NH—C(O)—, †-NH—C(O)—CF$_2$—CH$_2$—, †-CH$_2$—, †-NH—, †-NH—CH$_2$—, †-CH$_2$—NH—, †-NH—C(O)—CH(CF$_3$)—, †-N(CH$_3$)—CH$_2$—, †-NH—C(O)—CH$_2$—CH$_2$—, †-CH(CH$_3$)—, †-N(CH$_3$)—, and †-NH—CH$_2$—CH(CF$_3$)—, wherein "†" represents a portion of $R^3$ bound to Q.

In some embodiments, Z is selected from a bond,
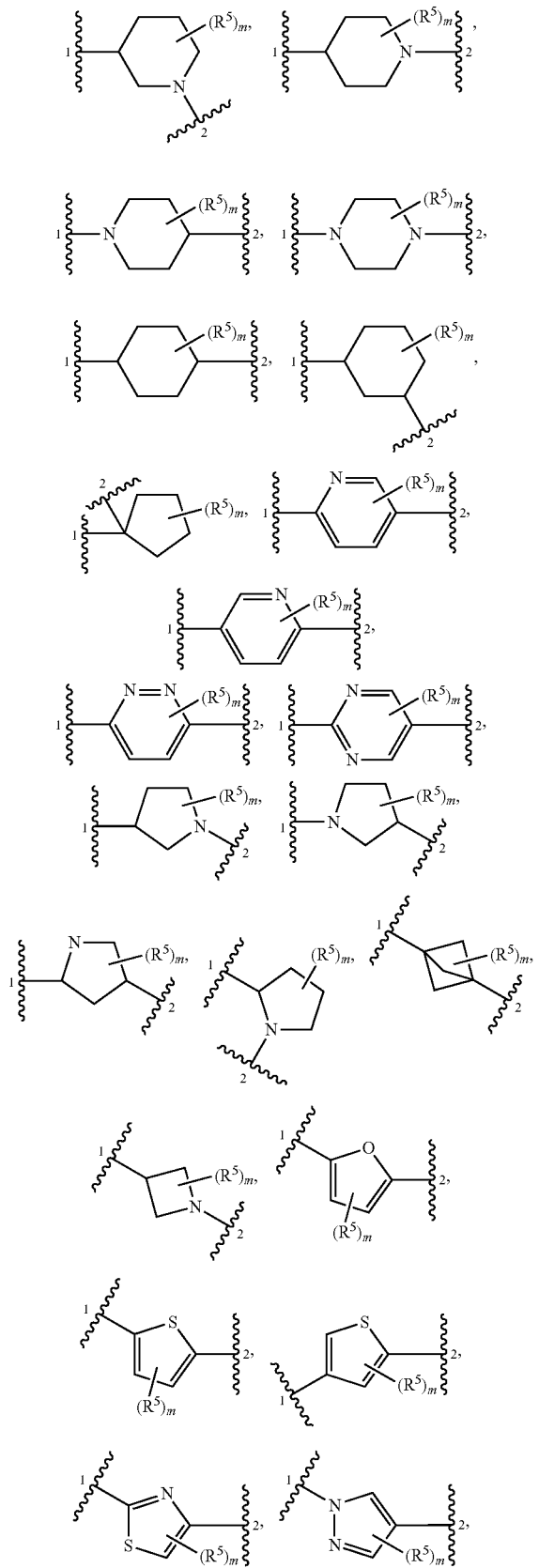
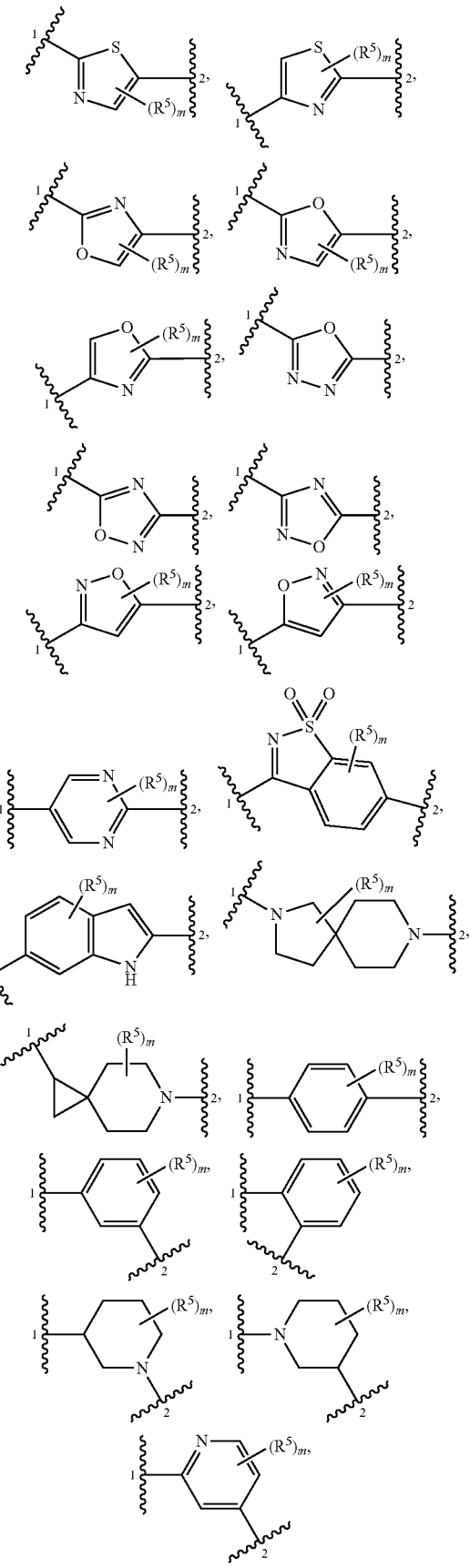
-continued -continued

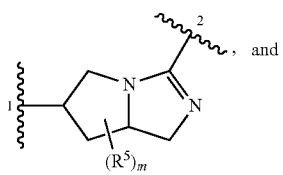
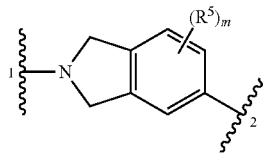
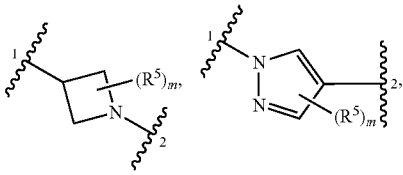
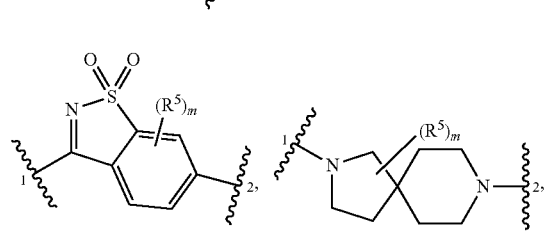

wherein: "1" represents a portion of Z bound to $R^3$; "2" represents a portion of Z bound to $R^4$; each instance of $R^5$, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1})_2$, and $-SR^{D1}$, wherein each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, and optionally substituted aryl, optionally substituted heteroaryl; and m is 0, 1, 2, 3 or 4.

In some aspects of these embodiments, Z is selected from a bond,

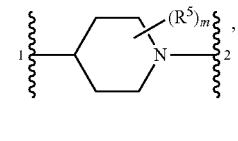
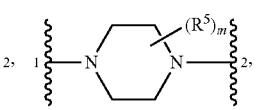
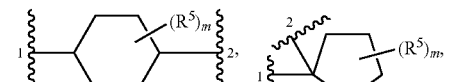
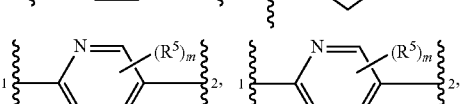
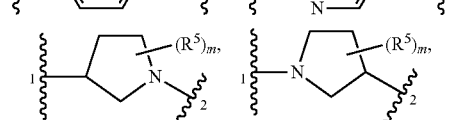
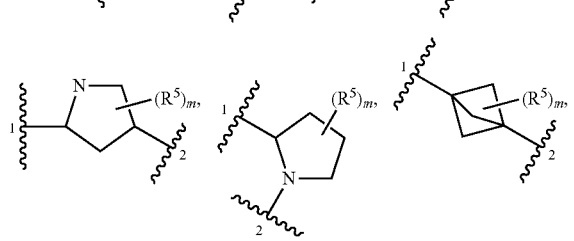

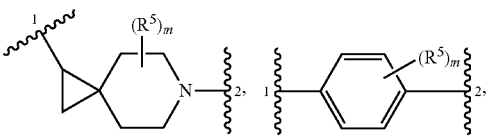
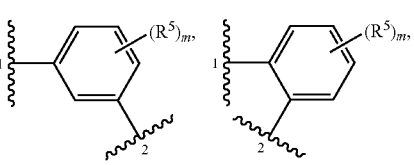
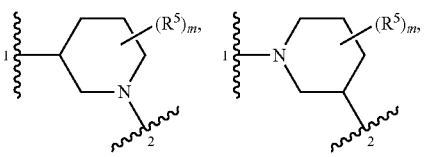
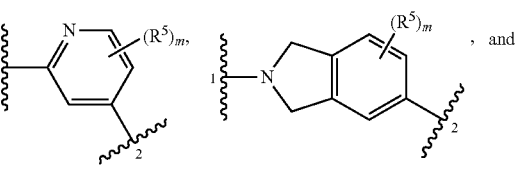
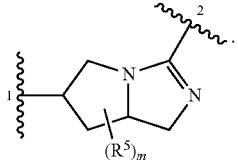

In some aspects of these embodiments, Z is selected from a bond, cyclohex-1,4-diyl, piperidin-3,1-diyl, piperidin-4,1-diyl, piperidin-1,2-diyl, piperidin-2,1-diyl, pyridin-2,5-diyl, pyridin-2,4-diyl, bicyclo[1.1.1]pent-1,3-diyl, pyrimidin-2,5-diyl, pyrazol-1,4-diyl, pyrrolidin-2,1-diyl, 4,4-difluoropyrrolidin-2,1-diyl, isoindolin-2,5-diyl, 6-azaspiro[2.5]octan-6,1-diyl, 2,8-diazaspiro[4.5]decan-2,8-diyl, pyrrolidin-3,1-diyl, 5,6,7,7a-tetrahydro-1H-pyrrolo[1,2-c]imidazol-3,6-diyl, 1,1-dioxobenzo[d]isothiazol-3,6-diyl, piperazin-1,4-diyl, pyrrolidin-1,3-diyl, piperidin-1,4-diyl, pyrrolidin-2,4-diyl, 2,2-difluorocyclopent-1,1-diyl, 3-fluoroazetidin-3,1-diyl, 3,3-difluoropiperidin-4,1-diyl, benzene-1,2-diyl, benzene-1,3-diyl, benzene-1,4-diyl, and 4-hydroxypyrrolidin-3,1-diyl.

In some embodiments, $R^4$ is

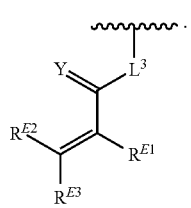

(ii-1)

In some aspects of these embodiments, $L^3$ is selected from a bond, —NH—, —CH$_2$—NH—, —S(O)$_2$—NH—, and —NH—S(O)$_2$—NH—, wherein "" represents a portion of $L^3$ bound to —C(=Y)—. In some embodiments, Y is O. In some aspects of these embodiments, $R^4$ is selected from: —CH$_2$—NH—C(O)—CH=CH—CH$_2$—N(CH$_3$)$_2$, —NH—C(O)—CH=CH—CH$_2$—N(CH$_3$)$_2$, —C(O)—CH=CH—CH$_2$—N(CH$_3$)$_2$, —NH—C(O)—CH=CH$_2$, —C(O)—CH=CH$_2$, —C(O)—CH=CH—N(CH$_3$)$_2$, —S(O)$_2$—NH—C(O)—CH=CH$_2$, and —NH—S(O)$_2$—NH—C(O)—CH=CH$_2$—NH—C(O)—CH=CH$_2$.

In some embodiments, $R^4$ is

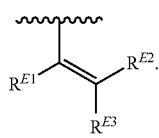

(ii-18)

In some aspects of these embodiments, $R^4$ is —CH=CH$_2$.
In some embodiments, $R^4$ is

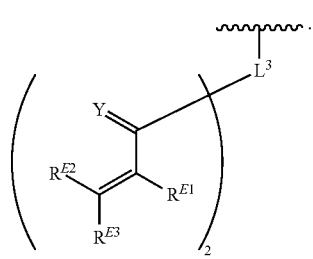

(ii-O)

In some aspects of these embodiments, $L^3$ is —N—. In some aspects of these embodiments, $R^4$ is —N(C(O)—CH=CH$_2$)$_2$.

Figure 1B:
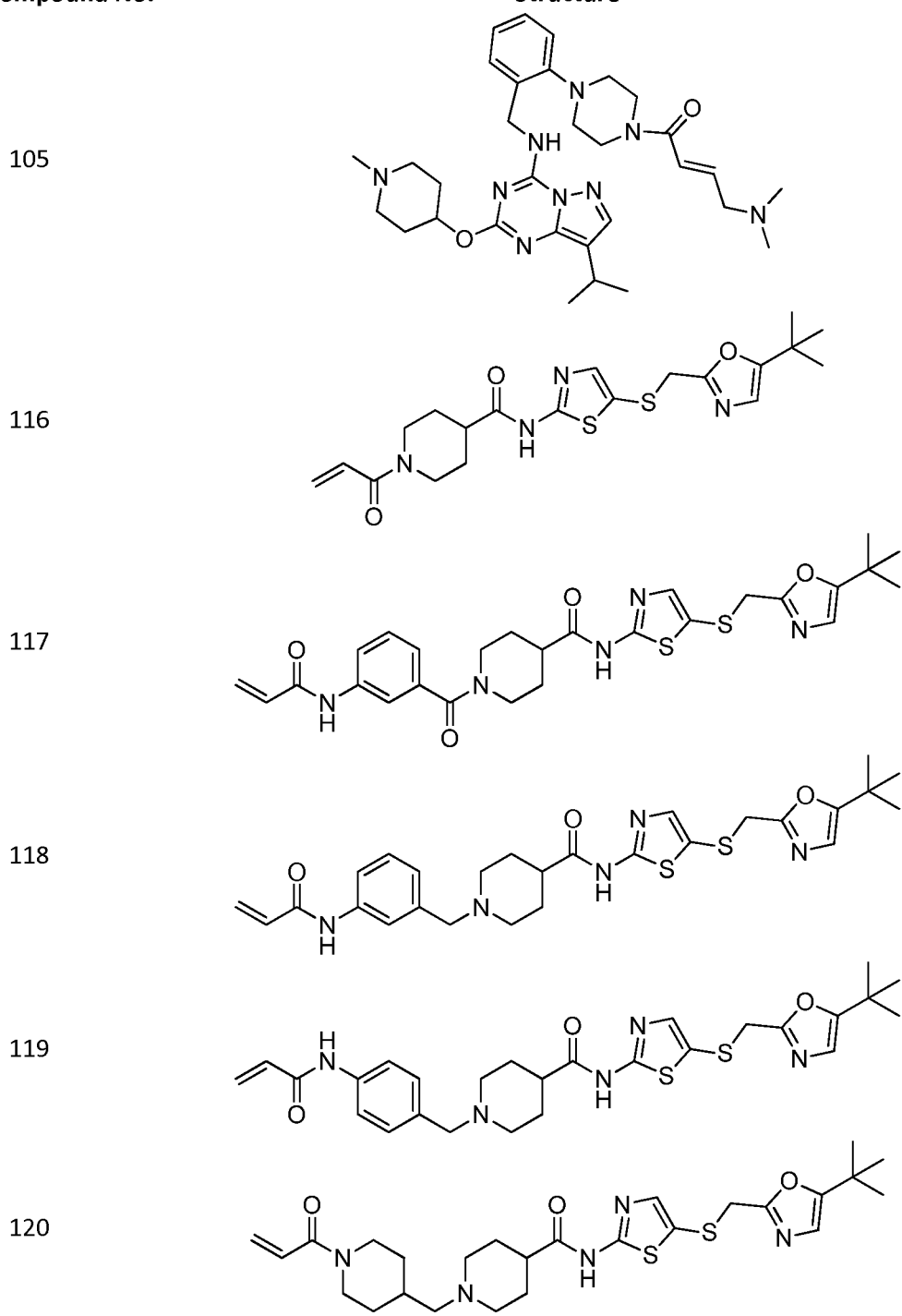
Figure 1C:
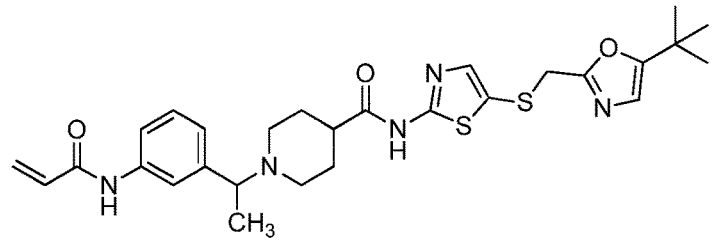
Figure 1C:
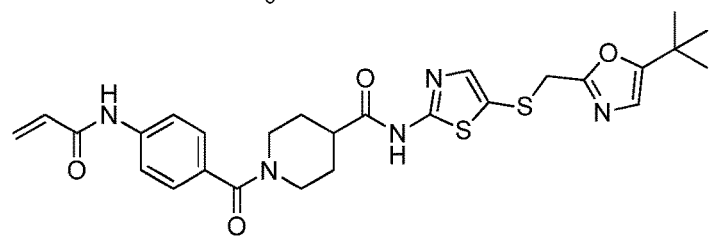
Figure 1C:
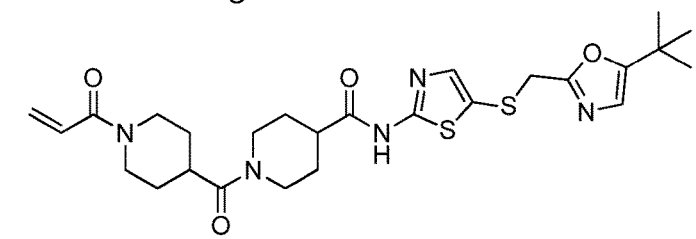
Figure 1C:
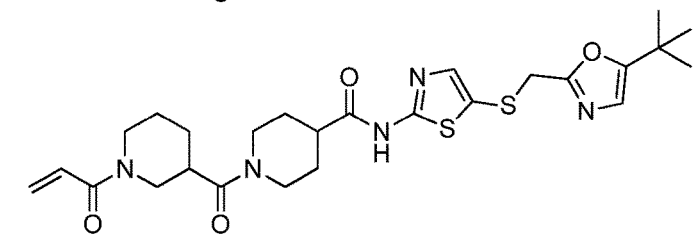
Figure 1C:
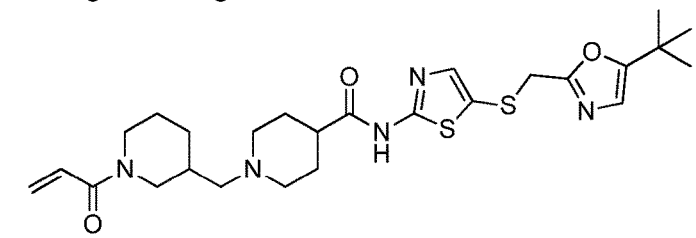
Figure 1C:
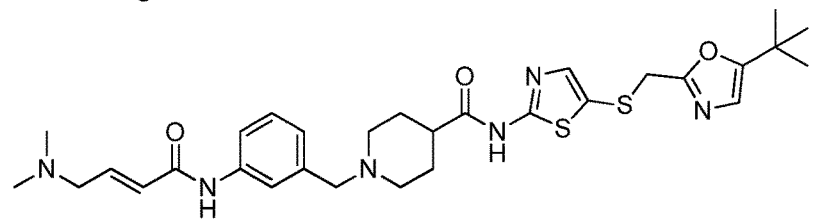

In some embodiments, the compound of Formula (I) is selected from the group consisting of any one of the compounds in the table of FIGS. 1A-1C and any pharmaceutically acceptable salts, solvates, hydrates, tautomers, stereoisomers, and isotopically labeled derivatives thereof.

Although, as indicated above, various embodiments and aspects thereof for a variable in Formula (I) may be selected from a group of chemical moieties, the invention also encompasses as further embodiments and aspects thereof situations where such variable is: a) selected from any subset of chemical moieties in such a group; and b) any single member of such group.

Although various embodiments and aspects thereof are set forth (or implied, as discussed in the preceding paragraph) individually for each variable in Formula (I) above, the invention encompasses all possible combinations of the different embodiments and aspects for each of the variables in Formula (I).

Pharmaceutical Compositions, Kits, and Administration

The present invention provides pharmaceutical compositions comprising a compound described herein, such as of Formula (I), or a pharmaceutically acceptable salt, solvate, hydrate, tautomer, stereoisomer, or isotopically labeled derivative thereof, as described herein, and optionally a pharmaceutically acceptable excipient. In certain embodiments, the pharmaceutical composition of the invention comprises a compound described herein, such as of Formula (I), or a pharmaceutically acceptable salt thereof, and optionally a pharmaceutically acceptable excipient. In certain embodiments, the compound described herein, such as of Formula (I), or a pharmaceutically acceptable salt, solvate, hydrate, tautomer, stereoisomer, or isotopically labeled derivative thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound described herein, such as of Formula (I) (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

The term "pharmaceutically acceptable excipient" refers to a non-toxic carrier, adjuvant, diluent, or vehicle that does not destroy the pharmacological activity of the compound with which it is formulated. Pharmaceutically acceptable excipients useful in the manufacture of the pharmaceutical compositions of the invention are any of those that are well known in the art of pharmaceutical formulation and include inert diluents, dispersing and/or granulating agents, surface active agents and/or emulsifiers, disintegrating agents, binding agents, preservatives, buffering agents, lubricating agents, and/or oils. Pharmaceutically acceptable excipients useful in the manufacture of the pharmaceutical compositions of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or orally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the compositions are administered orally, subcutaneously, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Alternatively, pharmaceutically acceptable compositions of this invention may be administered in the form of suppositories for rectal administration. Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For ophthalmic use, provided pharmaceutically acceptable compositions may be formulated as micronized suspensions or in an ointment such as petrolatum.

Pharmaceutically acceptable compositions of this invention may also be administered by nasal aerosol or inhalation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form, e.g., single unit dosage form, for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein, such as of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, tautomer, stereoisomer, and isotopically labeled derivative, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating a proliferative disease in a subject. In certain embodiments, the kits further include instructions for administering the compound, or a pharmaceutically acceptable salt, solvate, hydrate, tautomer, stereoisomer, isotopically and labeled derivative thereof, or a pharmaceutical composition thereof, to a subject to prevent and/or treat a proliferative disease.

Methods of Treatment and Uses

The present invention also provides methods for the treatment or prevention of a proliferative disease (e.g., cancer, benign neoplasm, angiogenesis, inflammatory disease, autoinflammatory disease, or autoimmune disease) or an infectious disease (e.g., a viral disease) in a subject. Such methods comprise the step of administering to the subject in need thereof an effective amount of a compound described herein, such as of Formula (I), or a pharmaceutically acceptable salt, solvate, hydrate, tautomer, stereoisomer, or isotopically labeled derivative thereof, or a pharmaceutical composition thereof. In certain embodiments, the methods described herein include administering to a subject an effective amount of a compound described herein, such as of Formula (I), or a pharmaceutically acceptable salt thereof, or a pharmaceutical composition thereof.

In one aspect of the present invention, provided is a method of treating a subject suffering from a disease or condition associated with aberrant activity of CDK7 comprising the step of administering to the subject in need thereof with a composition described herein, e.g., a composition comprising a compound as described herein, e.g., a compound of formula (I). In some embodiments, the disease or condition is selected from cancer, benign neoplasm, angiogenesis, inflammatory disease, autoinflammatory disease, autoimmune disease, or an infectious disease. In some embodiments, the subject is a mammal. In some embodiments, the disease is cancer. In some embodiments, the cancer is selected from a blood cancer, melanoma, a bone cancer, a breast cancer, a brain cancer, or a lung cancer. In some embodiments, the cancer is a blood cancer selected from chronic lymphocytic leukemia (CLL), acute lymphoblastic leukemia (ALL), T-cell acute lymphoblastic leukemia (T-ALL), chronic myelogenous leukemia (CML), acute myelogenous leukemia (AML), lymphoma, and multiple myeloma. In some embodiments, the disease is a bone cancer selected from osteosarcoma and Ewing's sarcoma. In some embodiments, the disease is triple-negative breast cancer (TNBC). In some embodiments, the disease is neuroblastoma. In some embodiments, the disease is small cell lung cancer (SCLC). In some embodiments, the method comprises the additional step of administering to the subject in need thereof one or more additional agents independently selected from anti-proliferative agents, anti-cancer agents, immunosuppressant agents, and pain-relieving agents.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

The proliferative disease to be treated or prevented using the compounds described herein, such as of Formula (I) will typically be associated with aberrant activity of CDK7. Aberrant activity of CDK7 may be an elevated and/or an inappropriate (e.g., abnormal) activity of CDK7. In certain embodiments, CDK7 is not overexpressed, and the activity of CDK7 is elevated and/or inappropriate. In certain other embodiments, CDK7 is overexpressed, and the activity of CDK7 is elevated and/or inappropriate. The compounds described herein, such as of Formula (I), and pharmaceutically acceptable salts, solvates, hydrates, tautomers, stereoisomers, isotopically labeled derivatives, and compositions thereof, may inhibit the activity of CDK7 and be useful in treating and/or preventing proliferative diseases.

In other embodiments, the proliferative disease to be treated or prevented using the compounds described herein, such as of Formula (I), will typically be associated with aberrant activity of CDK12 and/or CDK13. Aberrant activity of CDK12 and/or CDK13 may be an elevated and/or an inappropriate (e.g., abnormal) activity of CDK12 and/or CDK13. In certain embodiments, CDK12 and/or CDK13 is not overexpressed, and the activity of CDK12 and/or CDK13 is elevated and/or inappropriate. In certain other embodiments, CDK12 and/or CDK13 is overexpressed, and the activity of CDK12 and/or CDK13 is elevated and/or inappropriate. The compounds described herein, such as of Formula (I), and pharmaceutically acceptable salts, solvates, hydrates, tautomers, stereoisomers, isotopically labeled derivatives, and compositions thereof, may inhibit the activity of CDK12 and/or CDK13 and be useful in treating and/or preventing proliferative diseases.

A proliferative disease may also be associated with inhibition of apoptosis of a cell in a biological sample or subject. All types of biological samples described herein or known in the art are contemplated as being within the scope of the invention. Inhibition of the activity of CDK7 is expected to cause cytotoxicity via induction of apoptosis. The compounds described herein, such as of Formula (I), and pharmaceutically acceptable salts, solvates, hydrates, tautomers, stereoisomers, isotopically labeled derivatives, and compositions thereof, may induce apoptosis, and therefore, be useful in treating and/or preventing proliferative diseases.

In certain embodiments, the proliferative disease to be treated or prevented using the compounds described herein, such as of Formula (I), is cancer. All types of cancers disclosed herein or known in the art are contemplated as being within the scope of the invention. In certain embodiments, the proliferative disease is a cancer associated with dependence on BCL-2 anti-apoptotic proteins (e.g., MCL-1 and/or XIAP). In certain embodiments, the proliferative disease is a cancer associated with overexpression of MYC (a gene that codes for a transcription factor). In certain embodiments, the proliferative disease is a hematological malignancy. In certain embodiments, the proliferative disease is a blood cancer. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is lymphoma. In certain embodiments, the proliferative disease is melanoma. In certain embodiments, the proliferative disease is multiple myeloma. In certain embodiments, the proliferative disease is a bone cancer. In certain embodiments, the proliferative disease is osteosarcoma. In some embodiments, the proliferative disease is Ewing's sarcoma. In some embodiments, the proliferative disease is triple-negative breast cancer (TNBC). In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is large cell lung cancer. In some embodiments, the proliferative disease is a benign neoplasm. All types of benign neoplasms disclosed herein or known in the art are contemplated as being within the scope of the invention.

In some embodiments, the proliferative disease is associated with angiogenesis. All types of angiogenesis disclosed herein or known in the art are contemplated as being within the scope of the invention.

In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

The cell described herein may be an abnormal cell. The cell may be in vitro or in vivo. In certain embodiments, the cell is a proliferative cell. In certain embodiments, the cell is a blood cell. In certain embodiments, the cell is a lymphocyte. In certain embodiments, the cell is a cancer cell. In certain embodiments, the cell is a leukemia cell. In certain embodiments, the cell is a CLL cell. In certain embodiments, the cell is a melanoma cell. In certain embodiments, the cell is a multiple myeloma cell. In certain embodiments, the cell is a benign neoplastic cell. In certain embodiments, the cell is an endothelial cell. In certain embodiments, the cell is an immune cell.

In another aspect, the present invention provides methods of down-regulating the expression of CDK7 in a biological sample or subject.

In certain embodiments, the methods described herein comprise the additional step of administering one or more additional pharmaceutical agents in combination with the compound described herein, such as of Formula (I), a pharmaceutically acceptable salt thereof, or compositions comprising such compound or pharmaceutically acceptable salt thereof. Such additional pharmaceutical agents include, but are not limited to, anti-proliferative agents, anti-cancer agents, anti-diabetic agents, anti-inflammatory agents, immunosuppressant agents, and a pain-relieving agent. The additional pharmaceutical agent(s) may synergistically augment inhibition of CDK7 induced by the inventive compounds or compositions of this invention in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In yet another aspect, the present invention provides the compounds described herein, such as of Formula (I), and pharmaceutically acceptable salts, solvates, hydrates, tautomers, stereoisomers, isotopically labeled derivatives, and compositions thereof, for use in the treatment of a proliferative disease in a subject. In certain embodiments, provided by the invention are the compounds described herein, and pharmaceutically acceptable salts and compositions thereof, for use in the treatment of a proliferative disease in a subject. In certain embodiments, provided by the invention are the compounds described herein, and pharmaceutically acceptable salts and compositions thereof, for use in inhibiting cell growth. In certain embodiments, provided by the invention are the compounds described herein, and pharmaceutically acceptable salts and compositions thereof, for use in inducing apoptosis in a cell. In certain embodiments, provided by the invention are the compounds described herein, and pharmaceutically acceptable salts and compositions thereof, for use in inhibiting transcription.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using modifications to the specific synthesis protocols set forth below that would be well known to those of skill in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, Second Edition, Wiley, New York, 1991, and references cited therein.

Abbreviations

| Abbreviation | Name |
| --- | --- |
| Ac | acetyl |
| ACN | acetonitrile |
| aq. | aqueous |
| atm | atmospheres |
| Boc | tert-butoxy carbonyl |
| Boc$_2$O | Di-t-butyl dicarbonate |
| CDI | 1,1'-Carbonyldiimidazole |
| DCC | N,N'-Dicyclohexylcarbodiimide |
| DCM | Dichloromethane |
| DIPEA | N,N-Diisopropyl ethylamine |
| DMF | Dimethylformamide |
| DMSO | Dimethylsulfoxide |
| EDTA | Ethylenediamine tetraacetic acid |
| eq(s). | equivalent(s) |
| EtOAc | Ethyl acetate |
| Et | Ethyl |
| EtOH | Ethanol |
| Et$_3$N | Triethylamine |
| g | gram(s) |
| h | hour(s) |
| HATU | (Dimethylamino)-N,N-dimethyl(3H-[1,2,3]triazolo[4,5-b]pyridin-3-yloxy)methaniminium hexafluorophosphate |
| HBTU | O-Benzotriazole-N,N,N',N'-tetramethyl-uronium-hexafluoro-phosphate |
| Hex | Hexanes |
| HOBt | 1-Hydroxybenzotriazole |
| HPLC | High pressure liquid chromatography |
| IPA | Isopropanol |
| LCMS; LC-MS | liquid chromatography mass spectrometry |
| MeOH | Methanol |
| mg | milligram(s) |
| min | Minute(s) |
| mL; ml | milliliter(s) |
| MS | mass spectrometry |
| mW | megawatt |
| NMe | N-methyl |
| NMP | N-Methyl-2-pyrrolidone |
| NMR | Nuclear magnetic resonance |
| Ph | phenyl |
| POCl$_3$ | Phosphoryl Chloride |
| Py | Pyridine |
| r.t; rt; RT | Room temperature |
| S., sat. | saturated |
| TEA | Triethylamine |
| TFA | Trifluoroacetic acid |
| THF | Tetrahydrofuran |
| TLC | Thin layer chromatography |

Example 1: Synthesis of (E)-4-(Dimethylamino)-N-(4-(4-((8-isopropyl-2-((1-methylpiperidin-4-yl)oxy)pyrazolo[1,5-a][1,3,5]triazin-4-yl)amino)piperidine-1-carbonyl)phenyl)but-2-enamide (Compound 102)
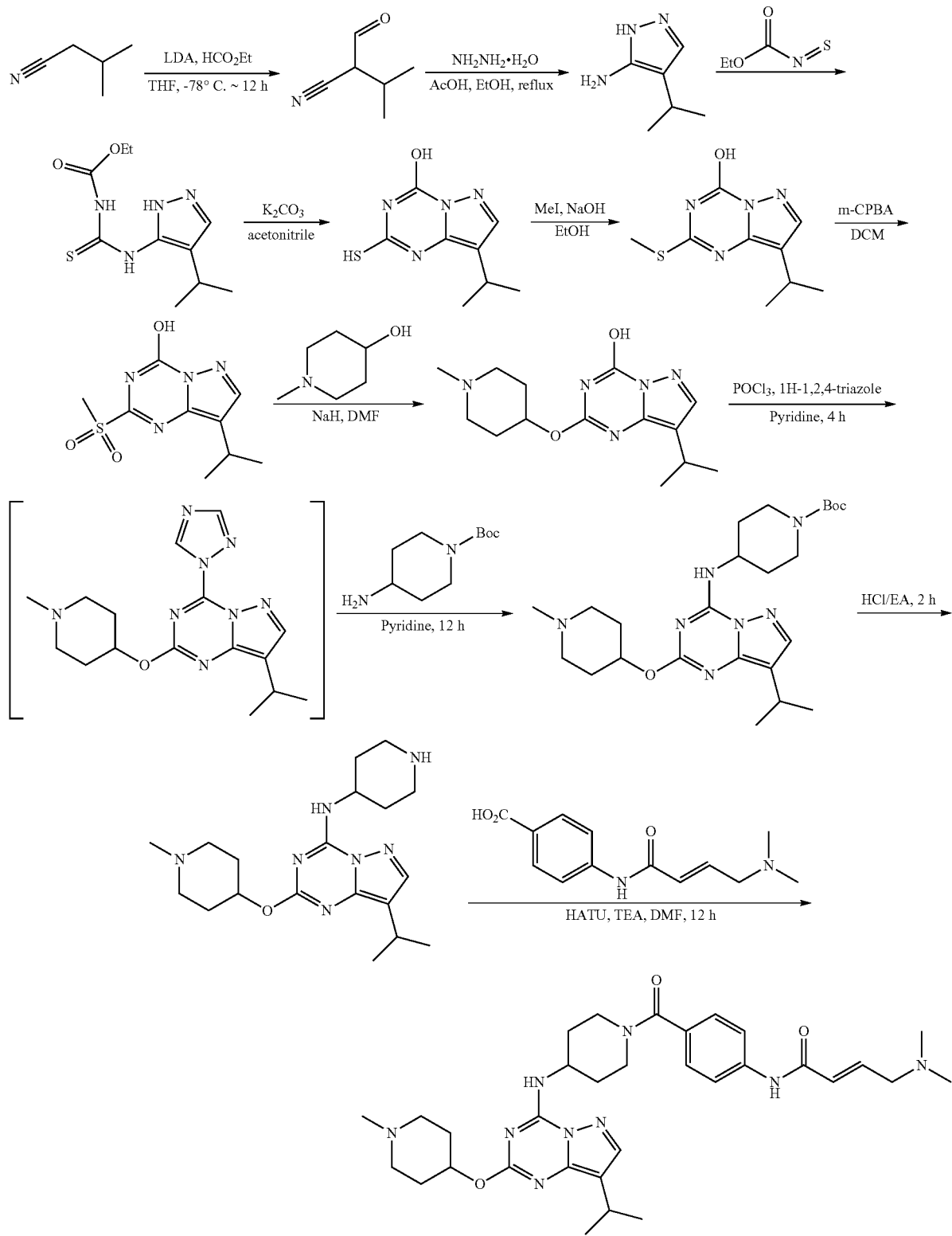

8-isopropyl-2-((1-methylpiperidin-4-yl)oxy)-4-(1H-1,2,4-triazol-1-yl)pyrazolo[1,5-a][1,3,5]triazine

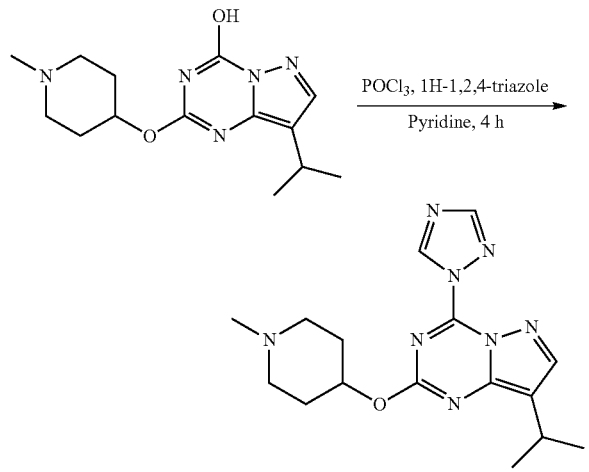

To a solution of 1H-1,2,4-triazole (1.07 g, 15.48 mmol) in Py (10 mL) was added POCl₃ (791 mg, 5.16 mmol). The mixture was stirred at room temperature for 2 h, followed by addition of 8-isopropyl-2-((1-methylpiperidin-4-yl)oxy)pyrazolo[1,5-a][1,3,5]triazin-4-ol (500 mg, 1.72 mmol). After stirring at room temperature for 4 h, LC-MS showed complete conversion to the desired product. The solution was used directly in the next step. The mixture was stirred at room temperature for 4 h. LCMS: (M+H⁺): 343.

tert-butyl 4-((8-isopropyl-2-((1-methylpiperidin-4-yl)oxy)pyrazolo[1,5-a][1,3,5]triazin-4-yl)amino)piperidine-1-carboxylate

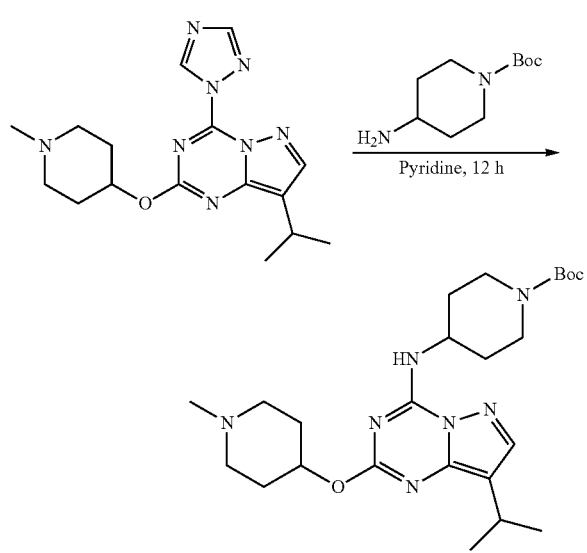

To a solution of 8-isopropyl-2-((1-methylpiperidin-4-yl)oxy)pyrazolo[1,5-a][1,3,5]triazin-4-ol (587.6 mg, 1.72 mmol) in Py (10 mL) was added tert-butyl 4-aminopiperidine-1-carboxylate (1.03 g, 5.16 mmol), and the mixture was stirred at room temperature for 12 h, after which LCMS showed the reaction was completed. The mixture was concentrated under vacuum, and the residue was purified by preparative HPLC to afford tert-butyl 4-((8-isopropyl-2-((1-methylpiperidin-4-yl)oxy)pyrazolo[1,5-a][1,3,5]triazin-4-yl)amino)piperidine-1-carboxylate (200 mg, 24% yield). ¹H NMR: (CDCl₃; 400 MHz) δ 12.48 (s, 1H), 7.77 (s, 1H), 5.39 (s, 2H), 4.48 (s, 1H), 3.80 (s, 1H), 3.37-3.30 (m, 6H), 3.14-3.11 (m, 1H), 2.81 (d, J=4.80 Hz, 3H), 2.73-2.66 (m, 2H), 2.28 (d, J=14.80 Hz, 2H), 2.14 (d, J=10.40 Hz, 2H), 1.52 (d, J=11.20 Hz, 2H), 1.46 (s, 9H), 1.29-1.27 (m, 6H). LCMS: (M+H⁺): 474.

8-isopropyl-2-((1-methylpiperidin-4-yl)oxy)-N-(piperidin-4-yl)pyrazolo[1,5-a][1,3,5]triazin-4-amine

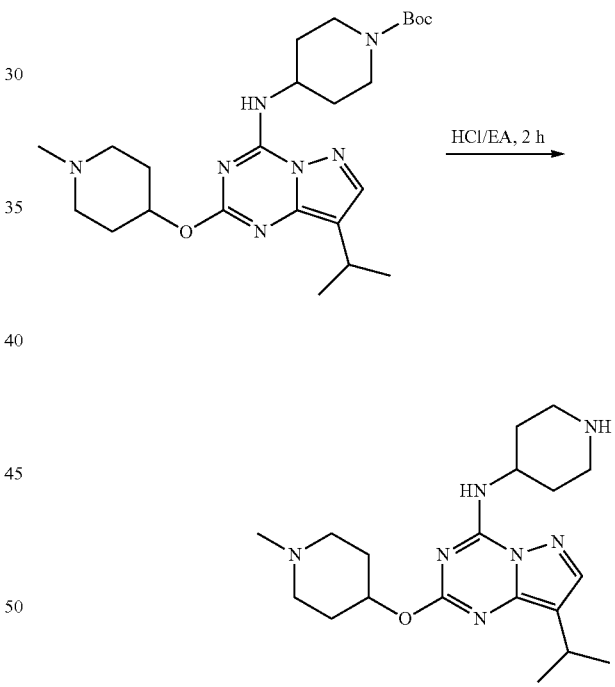

To a solution of tert-butyl 4-((8-isopropyl-2-((1-methylpiperidin-4-yl)oxy)pyrazolo[1,5-a][1,3,5]triazin-4-yl)amino)piperidine-1-carboxylate (170 mg, 0.36 mmol) in EtOAc (1 mL) was added HCl/EtOAc (10 mL). The mixture was stirred at room temperature for 2 h, after which LCMS showed the reaction was completed. The mixture was concentrated in vacuo to afford 8-isopropyl-2-((1-methylpiperidin-4-yl)oxy)-N-(piperidin-4-yl)pyrazolo[1,5-a][1,3,5]triazin-4-amine (135 mg, 100% yield). LCMS: (M+H⁺): 374

(E)-4-(Dimethylamino)-N-(4-(4-((8-isopropyl-2-((1-methylpiperidin-4-yl)oxy)pyrazolo[1,5-a][1,3,5]triazin-4-yl)amino)piperidine-1-carbonyl)phenyl)but-2-enamide (Compound 102)

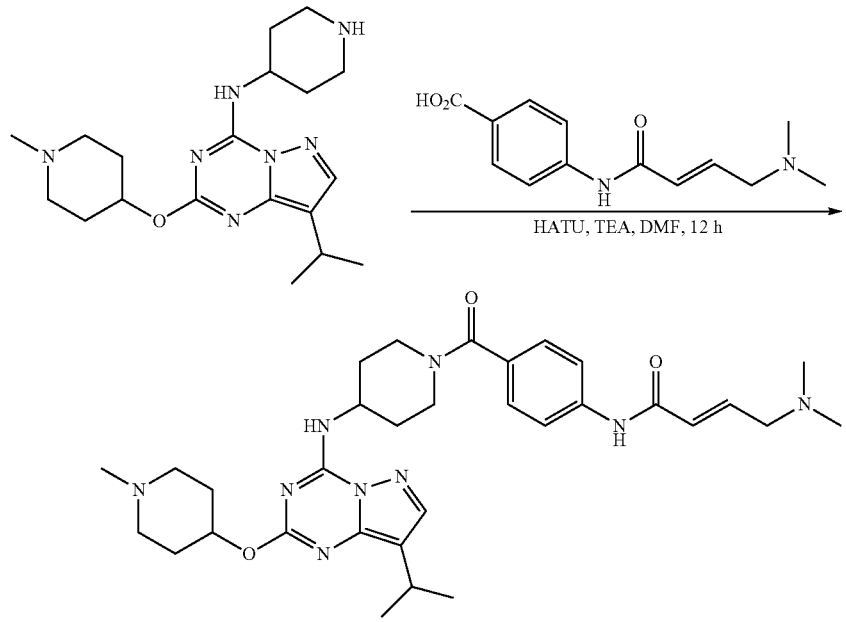

To a solution of 8-isopropyl-2-((1-methylpiperidin-4-yl)oxy)-N-(piperidin-4-yl)pyrazolo[1,5-a][1,3,5]triazin-4-amine (135 mg, 0.36 mmol) in DMF (2 mL) was added (E)-4-(4-(dimethylamino)but-2-enamido)benzoic acid (99 mg, 0.39 mmol), TEA (110 mg, 1.08 mmol), and HATU (151 mg, 0.39 mmol). The mixture was stirred at room temperature for 12 h, after which LCMS showed the reaction was completed. The mixture was then concentrated in vacuo, and the residue was purified by preparative HPLC to afford (E)-4-(dimethylamino)-N-(4-(4-((8-isopropyl-2-((1-methylpiperidin-4-yl)oxy)pyrazolo[1,5-a][1,3,5]triazin-4-yl)amino)piperidine-1-carbonyl)phenyl)but-2-enamide (30 mg, 14% yield). $^1$H NMR: (DMSO; 400 MHz) δ 10.28 (s, 1H), 8.18 (d, J=7.60 Hz, 1H), 7.93 (s, 1H), 7.81 (d, J=8.80 Hz, 2H), 7.71 (d, J=8.80 Hz, 2H), 6.78-6.72 (m, 1H), 6.29 (d, J=15.60 Hz, 1H), 5.25 (s, 1H), 4.95 (s, 1H), 4.16 (s, 1H), 3.42-3.36 (m, 4H), 3.11 (d, J=5.60 Hz, 2H), 2.99-2.98 (m, 1H), 2.83 (s, 2H), 2.54 (s, 1H), 2.36 (s, 3H), 2.21 (s, 6H), 2.04-1.95 (m, 4H), 1.79 (s, 2H), 1.65 (d, J=11.20 Hz, 2H), 1.25 (d, J=6.80 Hz, 6H). LCMS: (M+H$^+$): 604

Example 2: Synthesis of (E)-4-(4-(dimethylamino)but-2-enamido)-N-(2-(((8-isopropyl-2-((1-methylpiperidin-4-yl)oxy)pyrazolo[1,5-a][1,3,5]triazin-4-yl)amino)methyl)phenyl)benzamide (Compound 103)

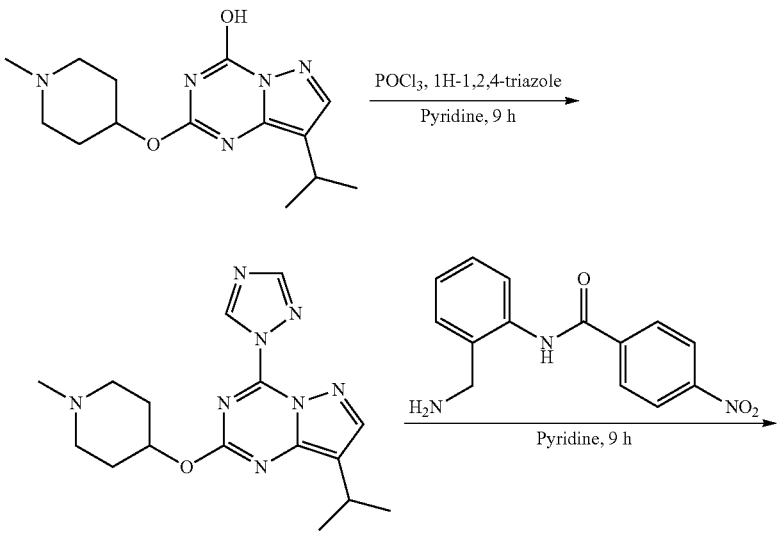

-continued
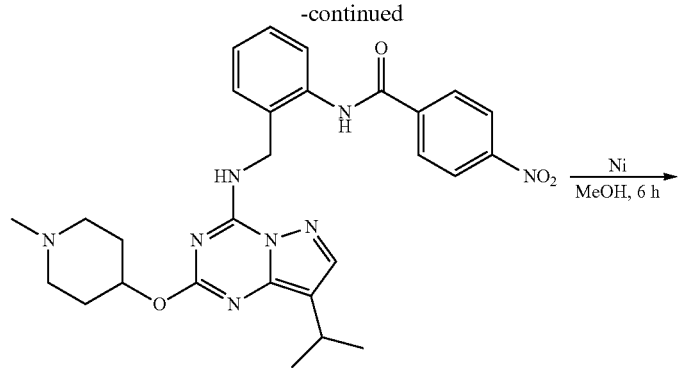
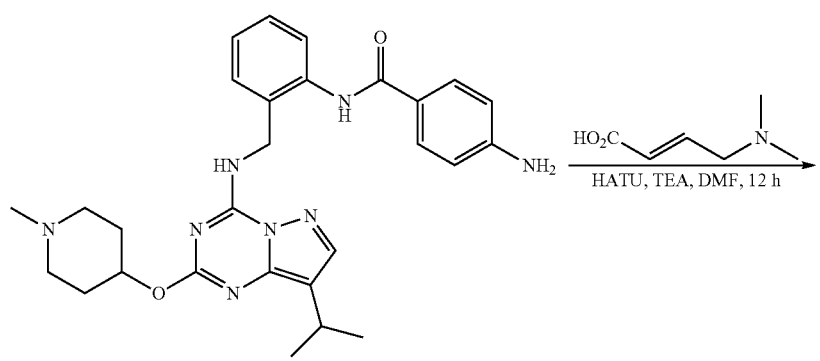
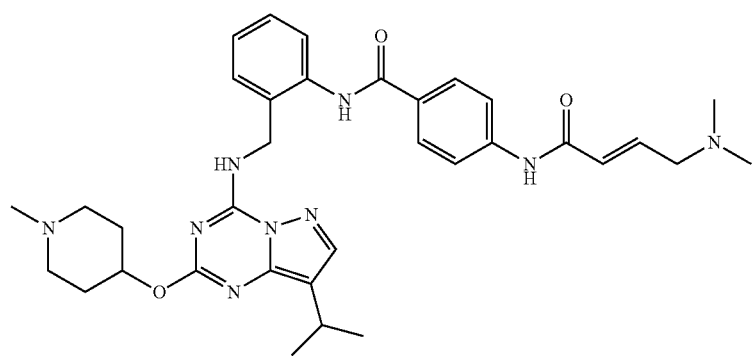
8-isopropyl-2-((1-methylpiperidin-4-yl)oxy)-4-(1H-1,2,4-triazol-1-yl)pyrazolo[1,5-a][1,3,5]triazine
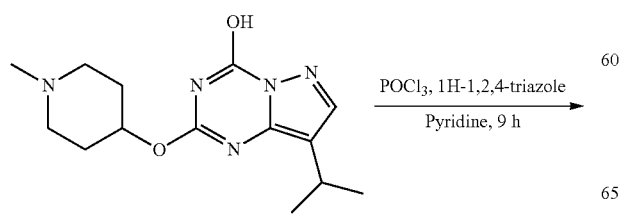
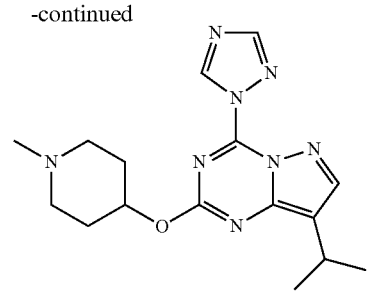
To a solution of 1H-1,2,4-triazole (1.07 g, 15.45 mmol) in Py (15 mL) was added POCl₃ (789 mg, 5.15 mmol). After stirring at room temperature for 1.5 h, 8-isopropyl-2-((1-methylpiperidin-4-yl)oxy)pyrazolo[1,5-a][1,3,5]triazin-4-ol (500 mg, 1.72 mmol) was then added and the mixture was stirred at room temperature for an additional 7.5 h. LCMS analysis indicated the reaction was complete, and the solution was used directly in next step. LCMS: (M+H$^+$): 343

N-(2-(((8-isopropyl-2-((1-methylpiperidin-4-yl)oxy)pyrazolo[1,5-a][ ][1,3,5]triazin-4-yl)amino)methyl)phenyl)-4-nitrobenzamide

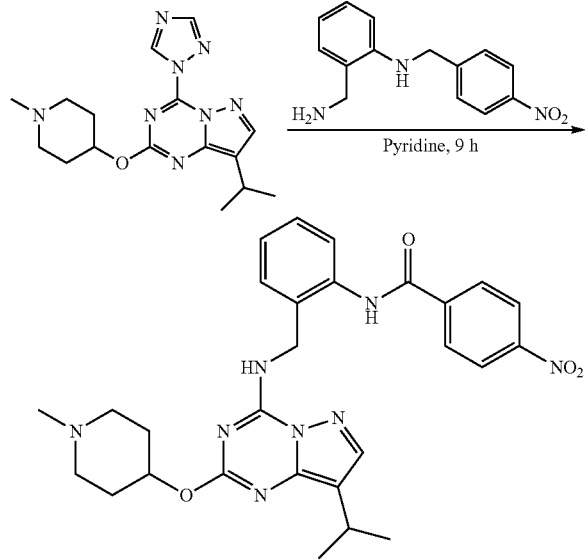

To a solution of 8-isopropyl-2-((1-methylpiperidin-4-yl)oxy)-4-(1H-1,2,4-triazol-1-yl)pyrazolo[1,5-a][1,3,5]triazine (587.6 mg, 1.72 mmol) in Py (10 mL) was added 2-(aminomethyl)-N-(4-nitrobenzyl)aniline (1.40 g, 5.15 mmol). The mixture was stirred at room temperature for 9 h, after which LCMS analysis indicated the reaction was complete. The mixture was concentrated in vacuo, and the residue was purified by preparative HPLC to afford N-(2-(((8-isopropyl-2-((1-methylpiperidin-4-yl)oxy)pyrazolo[1,5-a][1,3,5]triazin-4-yl)amino)methyl)phenyl)-4-nitrobenzamide (330 mg, 35% yield) as light yellow solid. $^1$H NMR: (MeOD; 400 MHz) δ 8.35-8.30 (m, 2H), 8.18 (d, J=7.60 Hz, 1H), 8.10 (d, J=8.00 Hz, 1H), 7.86 (s, 1H), 7.53-7.35 (m, 5H), 4.85 (s, 2H), 4.82 (s, 1H), 3.49 (s, 1H), 3.19-3.13 (m, 2H), 3.04-3.01 (m, 1H), 2.88-2.86 (m, 3H), 2.23-2.05 (m, 3H), 1.73 (s, 1H), 1.30 (d, J=6.80 Hz, 6H). LCMS: (M+H$^+$): 545.

4-amino-N-(2-(((8-isopropyl-2-((1-methylpiperidin-4-yl)oxy)pyrazolo[1,5-a][1,3,5]triazin-4-yl)amino)methyl)phenyl)benzamide

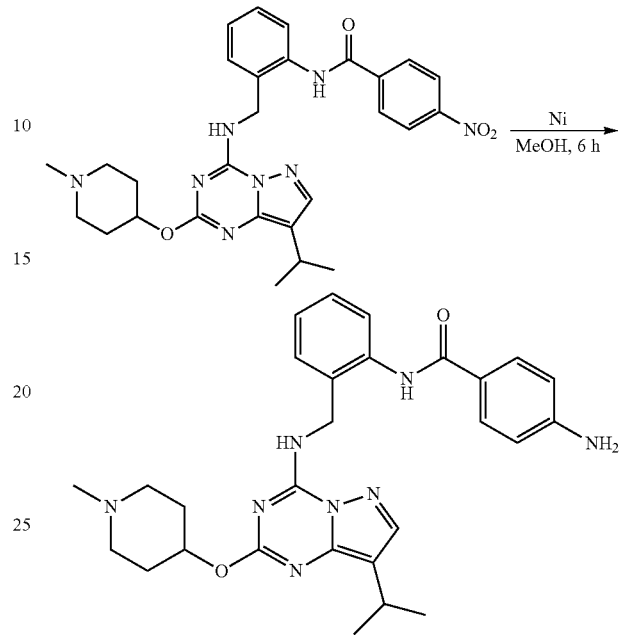

To a solution of N-(2-(((8-isopropyl-2-((1-methylpiperidin-4-yl)oxy)pyrazolo[1,5-a][1,3,5]triazin-4-yl)amino)methyl)phenyl)-4-nitrobenzamide (230 mg, 0.42 mmol) in MeOH (3 mL) was added Raney Ni (500 mg) under H$_2$ at 15 psi. The mixture was stirred at room temperature for 6 h, after which LCMS showed the reaction was complete. The mixture was then concentrated in vacuo to afford 4-amino-N-(2-(((8-isopropyl-2-((1-methylpiperidin-4-yl)oxy)pyrazolo[1,5-a][1,3,5]triazin-4-yl)amino)methyl)phenyl)benzamide (215 mg, 100% yield) as light yellow solid. $^1$H NMR: (MeOD; 400 MHz) δ 7.79 (s, 1H), 7.75 (d, J=8.40 Hz, 2H), 7.45-7.44 (m, 2H), 7.32-7.22 (m, 2H), 6.65 (d, J=8.40 Hz, 2H), 4.72 (s, 2H), 3.27 (s, 3H), 3.21-3.01 (m, 2H), 3.00-2.95 (m, 1H), 2.82-2.74 (m, 4H), 2.11-1.96 (m, 3H), 1.25 (d, J=6.80 Hz, 6H). LCMS: (M+H$^+$): 515

(E)-4-(4-(dimethylamino)but-2-enamido)-N-(2-(((8-isopropyl-2-((1-methylpiperidin-4-yl)oxy)pyrazolo[1,5-a][1,3,5]triazin-4-yl)amino)methyl)phenyl)benzamide (Compound 103)

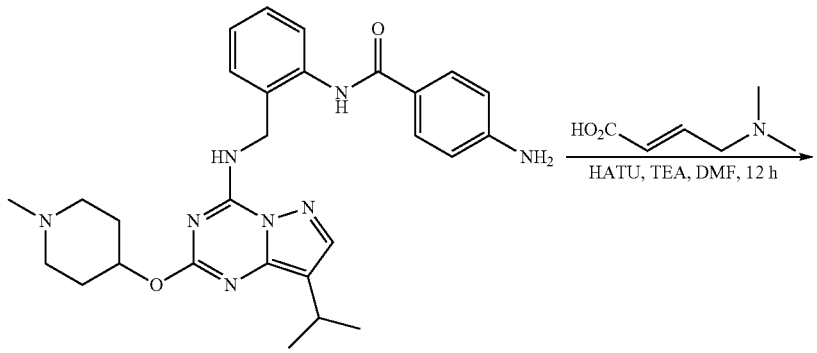

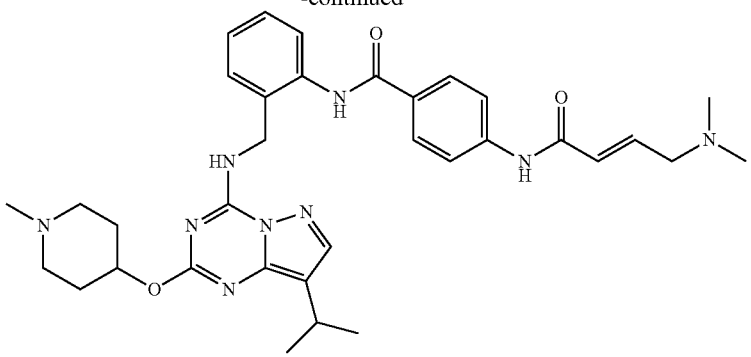

To a solution of 4-amino-N-(2-(((8-isopropyl-2-((1-methylpiperidin-4-yl)oxy)pyrazolo[1,5-a][1,3,5]triazin-4-yl)amino)methyl)phenyl)benzamide (140 mg, 0.27 mmol) in DMF (8 mL) was added (E)-4-(dimethylamino)but-2-enoic acid (53 mg, 0.41 mmol), TEA (110 mg, 1.09 mmol), and HATU (155 mg, 0.41 mmol). The mixture was stirred at room temperature for 12 h, after which LCMS showed the reaction was completed. The mixture was then concentrated in vacuo, and the residue was purified by preparative HPLC to afford Compound 103 (30 mg, 16% yield) as a brown solid. $^1$H NMR: (MeOD; 400 MHz) δ 8.19 (d, J=6.40 Hz, 2H), 8.12 (s, 1H), 7.85 (d, J=8.40 Hz, 2H), 7.61 (d, J=6.80 Hz, 1H), 7.38-7.33 (m, 2H), 7.24-7.22 (m, 1H), 6.78-6.71 (m, 1H), 6.38 (d, J=15.20 Hz, 1H), 5.43 (s, 1H), 4.45 (d, J=10.80 Hz, 2H), 3.90 (s, 2H), 3.61-3.45 (m, 2H), 3.14-3.09 (m, 2H), 2.90 (s, 3H), 2.86 (s, 1H), 2.83 (s, 6H), 2.47-2.11 (m, 4H), 1.25 (d, J=6.80 Hz, 6H). LCMS: (M+H$^+$)/2: 313, (M+H$^+$): 626

N-(2-(aminomethyl)phenyl)-4-nitrobenzamide

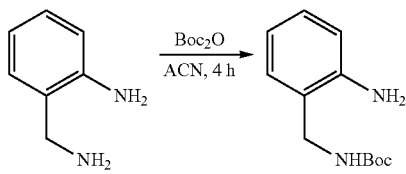 [SMILES: "Boc2O" ; NCc1ccccc1N ; CC(C)(C)OC(=O)NCc1ccccc1N]

To a solution of 2-(aminomethyl)aniline (10.00 g, 81.85 mmol) in ACN (100 mL) was added Boc$_2$O (17.86 g, 81.85 mmol) in portions. The mixture was stirred at room temperature for 4 h, after which TLC showed the reaction was complete. The mixture was concentrated in vacuo, and the residue was washed with PE/MTBE (50/1), filtered, and filter cake was concentrated in vacuo to afford tert-butyl 2-aminobenzylcarbamate (14.50 g, 79.7%) as a white solid. $^1$H NMR: (DMSO; 400 MHz) δ 7.27-7.24 (m, 1H), 6.97-6.94 (m, 2H), 6.63 (d, J=8.00 Hz, 1H), 6.53-6.49 (m, 1H), 5.01 (s, 2H), 3.99 (d, J=6.00 Hz, 2H), 1.41 (s, 9H). LCMS: (M+H$^+$): 223.

N-(2-(aminomethyl)phenyl)-4-nitrobenzamide

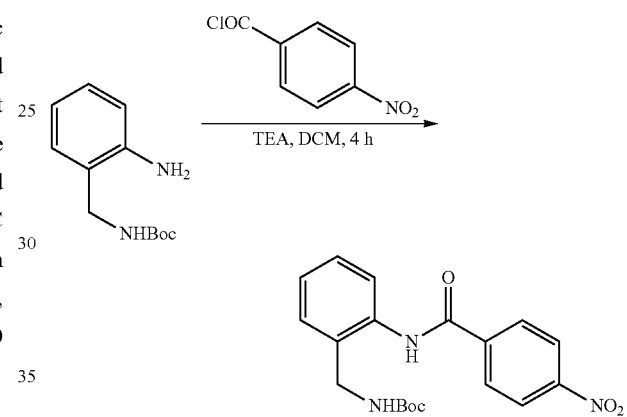

To a mixture of tert-butyl 2-aminobenzylcarbamate (2.00 g, 9.00 mmol) and TEA (1.82 g, 18.00 mmol) in DCM (50 mL) under N$_2$ was added a solution of 4-nitrobenzoyl chloride (1.84 g, 9.90 mmol) in DCM (10 mL) dropwise. The mixture was stirred at room temperature for 4 h, after which LCMS showed the reaction was completed. The mixture was concentrated in vacuo, and the residue was washed with PE/DCM (50/1), filtered, and filter cake was concentrated in vacuo to afford tert-butyl 2-(4-nitrobenzamido)benzylcarbamate (4.6 g, crude) as pale white solid. $^1$H NMR: (DMSO; 400 MHz) δ 10.51 (s, 1H), 8.37 (d, J=8.40 Hz, 2H), 8.25 (d, J=8.80 Hz, 2H), 7.47-7.46 (m, 2H), 7.36-7.26 (m, 3H), 4.17 (d, J=6.00 Hz, 2H), 1.36 (s, 9H). LCMS: (M+Na$^+$): 394.

N-(2-(aminomethyl)phenyl)-4-nitrobenzamide

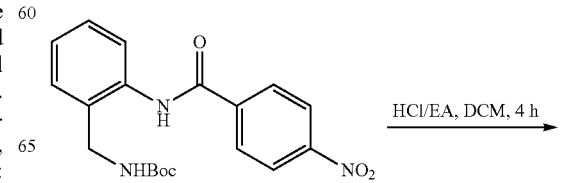

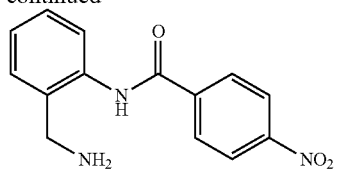

To a solution of tert-butyl 2-(4-nitrobenzamido)benzylcarbamate (crude 3.60 g, 9.69 mmol) in DCM (10 mL) was added HCl/EA (50 mL), and the mixture was stirred at room temperature for 4 h. Once LCMS showed the reaction was complete, the mixture was concentrated in vacuo to afford N-(2-(aminomethyl)phenyl)-4-nitrobenzamide (1.65 g, 63% yield) as pale white solid. $^1$H NMR: (MeOH; 400 MHz) δ 8.41 (d, J=8.80 Hz, 2H), 8.26 (d, J=8.40 Hz, 2H), 7.62 (d, J=7.20 Hz, 1H), 7.54-7.46 (m, 2H), 7.40 (d, J=7.60 Hz, 1H), 4.12 (s, 2H). LCMS: (M+H$^+$): 272.

Example 3: Synthesis of (E)-4-(dimethylamino)-N-(4-(((2-(((8-isopropyl-2-((1-methylpiperidin-4-yl)oxy)pyrazolo[1,5-a][1,3,5]triazin-4-yl)amino)methyl)phenyl)amino)methyl)phenyl)but-2-enamide (Compound 104)

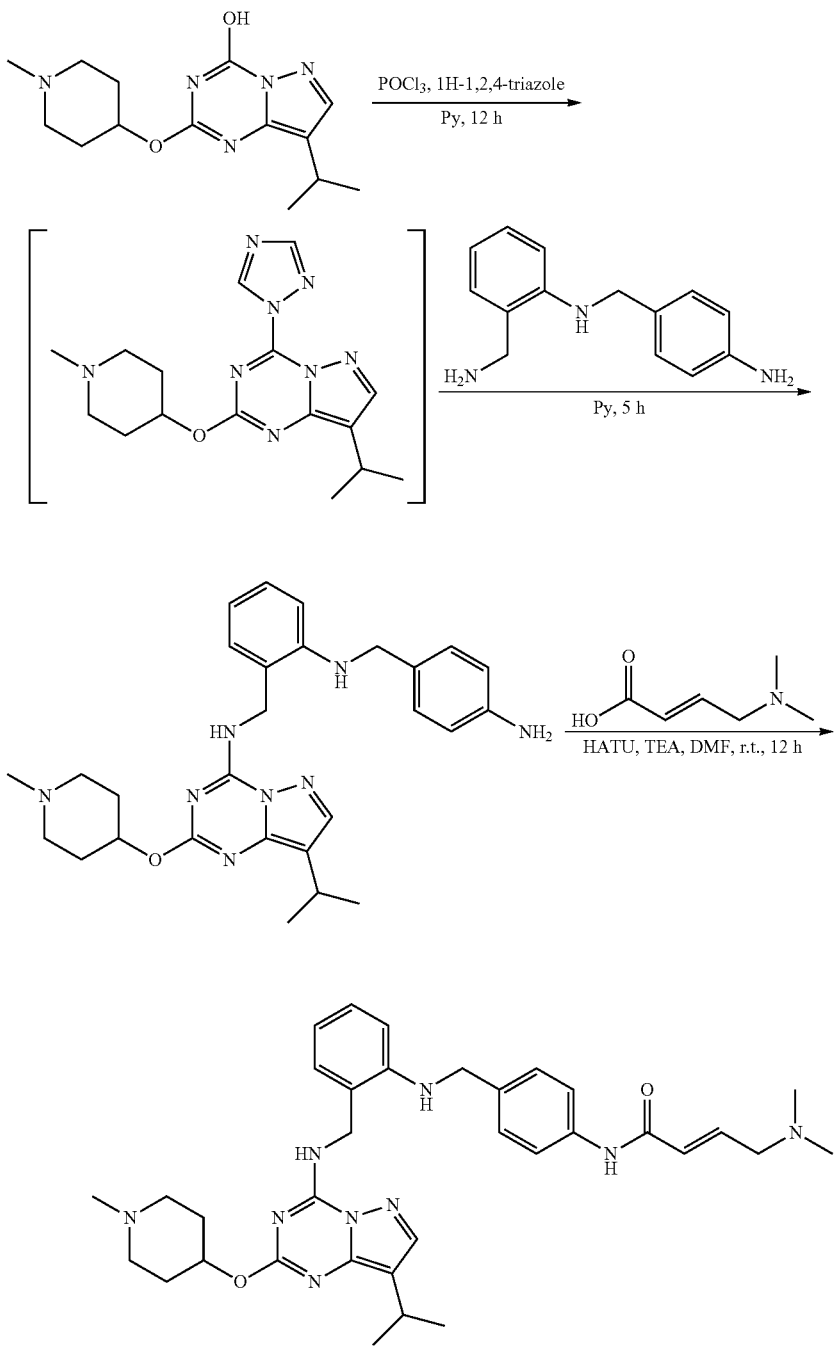

61

N-(4-aminobenzyl)-2-(aminomethyl)aniline

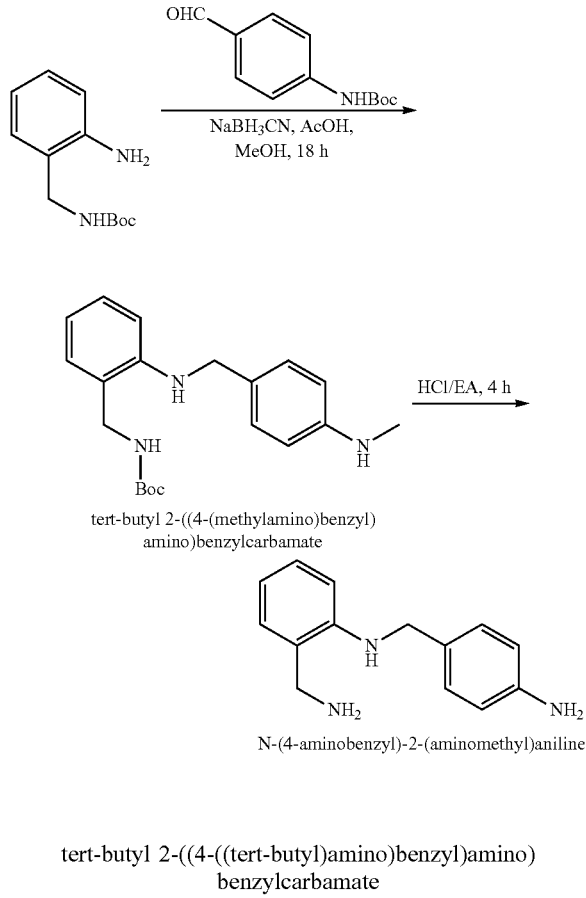

tert-butyl 2-((4-(methylamino)benzyl)amino)benzylcarbamate

N-(4-aminobenzyl)-2-(aminomethyl)aniline tert-butyl 2-((4-((tert-butyl)amino)benzyl)amino)benzylcarbamate To a solution of tert-butyl 2-aminobenzylcarbamate (2.00 g, 9.00 mmol) in MeOH (20 mL) was added tert-butyl (4-formylphenyl)carbamate (2.09 g, 9.45 mmol) and AcOH (351 mg, 5.85 mmol). After stirring at room temperature for 1 h, NaBH₃CN (1.13 g, 18.00 mmol) was added in portions. The mixture was stirred at room temperature for 12 h until TLC showed the reaction was complete. The mixture was concentrated in vacuo, and the residue was purified by column chromatography on silica gel to afford N-(4-aminobenzyl)-2-(aminomethyl)aniline (2.15 g, 56%) as a white solid. $^1$H NMR: (DMSO; 400 MHz) δ 9.23 (s, 1H), 7.37-7.35 (m, 3H), 7.21 (d, J=8.80 Hz, 2H), 6.98-6.93 (m, 2H), 6.52-6.50 (m, 1H), 6.42 (d, J=8.00 Hz, 1H), 5.77 (s, 1H), 4.25 (d, J=5.60 Hz, 2H), 4.05 (d, J=6.00 Hz, 2H), 1.46 (s, 9H), 1.38 (s, 9H). LCMS: (M+H$^+$): 428.

N-(4-aminobenzyl)-2-(aminomethyl)aniline

To a solution of tert-butyl 2-((4-((tert-butyl)amino)benzyl)amino)benzylcarbamate (2.15 g, 5.03 mmol) in EA (10 mL) was added HCl/EA (50 mL). The mixture was stirred at room temperature for 4 h until TLC showed the reaction was complete. The mixture was concentrated in vacuo to afford N-(4-aminobenzyl)-2-(aminomethyl)aniline (1.90 g, crude) as red brown solid. $^1$H NMR: (MeOH; 400 MHz) δ 7.69 (d, J=9.20 Hz, 1H), 7.61-7.58 (m, 2H), 7.53-7.51 (m, 3H), 7.40 (d, J=8.40 Hz, 2H), 4.50 (s, 2H), 4.33 (s, 2H).

62

8-isopropyl-2-((1-methylpiperidin-4-yl)oxy)-4-(1H-1,2,4-triazol-1-yl)pyrazolo[1,5-a][1,3,5]triazine

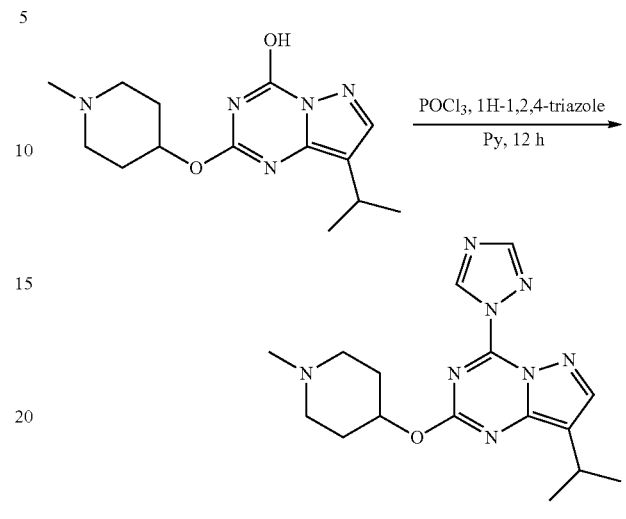

To a solution of 1H-1,2,4-triazole (1.07 g, 15.45 mmol) in Py (10 mL) was added POCl₃ (789 mg, 5.15 mmol). After stirring at room temperature for 1 h, 8-isopropyl-2-((1-methylpiperidin-4-yl)oxy)pyrazolo[1,5-a][1,3,5]triazin-4-ol (500 mg, 1.72 mmol) was added, and the mixture was stirred at room temperature for 11 h. LCMS showed the reaction was complete and only the desired product was formed. The solution was used directly in next step without further purification. LCMS: (M+H$^+$): 343.

N-(2-((4-aminobenzyl)amino)benzyl)-8-isopropyl-2-((1-methylpiperidin-4-yl)oxy)pyrazolo[1,5-a][1,3,5]triazin-4-amine

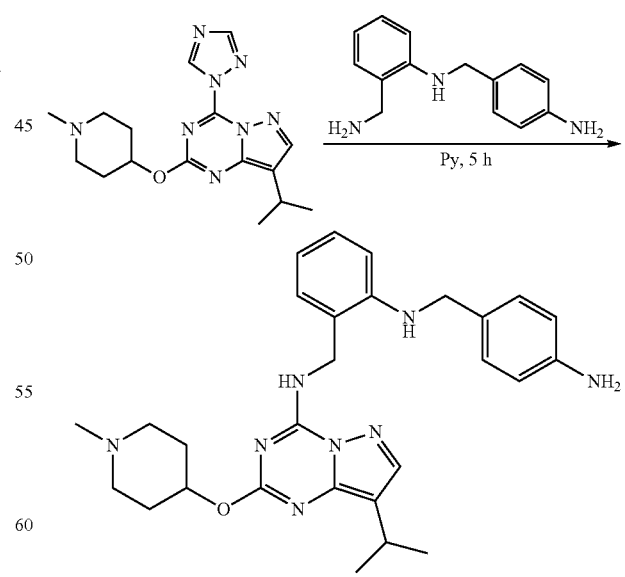

To a solution of 8-isopropyl-2-((1-methylpiperidin-4-yl)oxy)-4-(1H-1,2,4-triazol-1-yl)pyrazolo[1,5-a][1,3,5]triazine (587.6 mg, 1.72 mmol) in Py (10 mL) was added N-(4-aminobenzyl)-2-(aminomethyl)aniline (1.17 g, 5.16 mmol).

The mixture was stirred at room temperature for 5 h, after which LCMS showed the reaction was complete. The mixture was concentrated in vacuo to afford N-(2-((4-aminobenzyl)amino)benzyl)-8-isopropyl-2-((1-methylpiperidin-4-yl)oxy)pyrazolo[1,5-a][1,3,5]triazin-4-amine (2.00 g, Crude) as a brown oil. LCMS: (M+H⁺): 501.

(E)-4-(dimethylamino)-N-(4-(((2-(((8-isopropyl-2-((1-methylpiperidin-4-yl)oxy)pyrazolo[1,5-a][1,3,5]triazin-4-yl)amino)methyl)phenyl)amino)methyl)phenyl)but-2-enamide

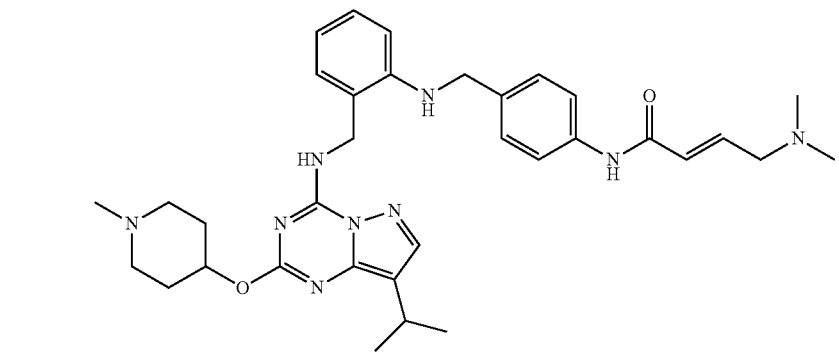

To a solution of N-(2-((4-aminobenzyl)amino)benzyl)-8-isopropyl-2-((1-methylpiperidin-4-yl)oxy)pyrazolo[1,5-a][1,3,5]triazin-4-amine (2.00 g, 3.99 mmol) in DMF (15 mL) was added (E)-4-(dimethylamino)but-2-enoic acid (774 mg, 5.99 mmol), TEA (1.21 g, 11.98 mmol) and HATU (2.28 g, 5.99 mmol). The mixture was stirred at room temperature for 12 h, after which LCMS showed the reaction was complete. The mixture was concentrated in vacuo. The residue was purified by preparative HPLC to afford Compound 104 (25 mg, 1% yield) as a yellow solid. ¹H NMR: (DMSO; 400 MHz) δ 8.29 (s, 1H), 7.96 (s, 1H), 7.70 (d, J=8.40 Hz, 2H), 7.37 (d, J=8.40 Hz, 2H), 7.08-7.00 (m, 2H), 6.67-6.63 (m, 1H), 6.57-6.53 (m, 2H), 6.12 (d, J=14.80 Hz, 1H), 5.91 (s, 1H), 5.68 (s, 1H), 4.96 (s, 1H), 4.36-4.32 (m, 4H), 3.07 (d, J=6.40 Hz, 2H), 2.81 (s, 2H), 2.39 (s, 2H), 2.33 (s, 3H), 2.21 (s, 6H), 2.05 (s, 3H), 1.82 (s, 2H), 1.32 (d, J=7.20 Hz, 6H). LCMS: (M+H⁺): 612.

Example 4: (E)-4-(Dimethylamino)-1-(4-(2-(((8-isopropyl-2-((1-methylpiperidin-4-yl)oxy)pyrazolo[1,5-a][1,3,5]triazin-4-yl)amino)methyl)phenyl)piperazin-1-yl)but-2-en-1-one (Compound 105)

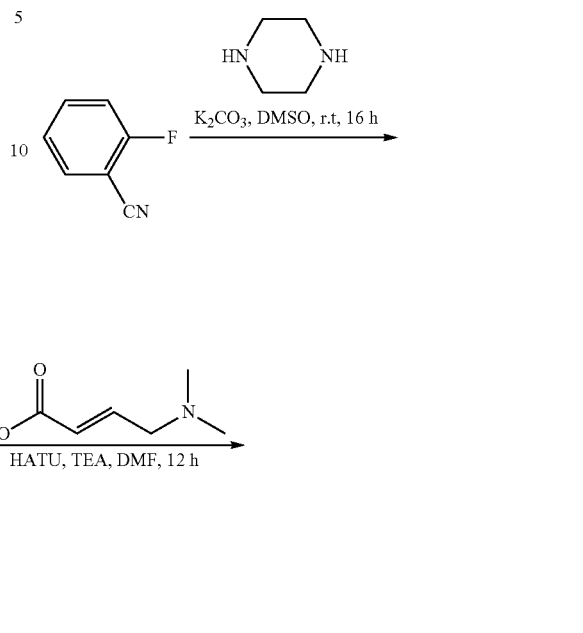

-continued

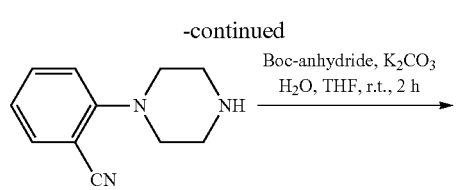

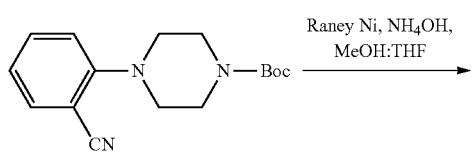

-continued

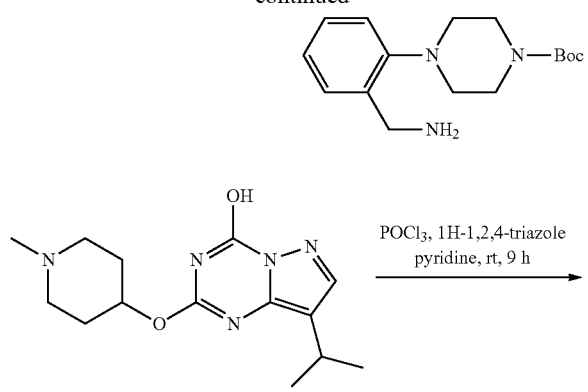

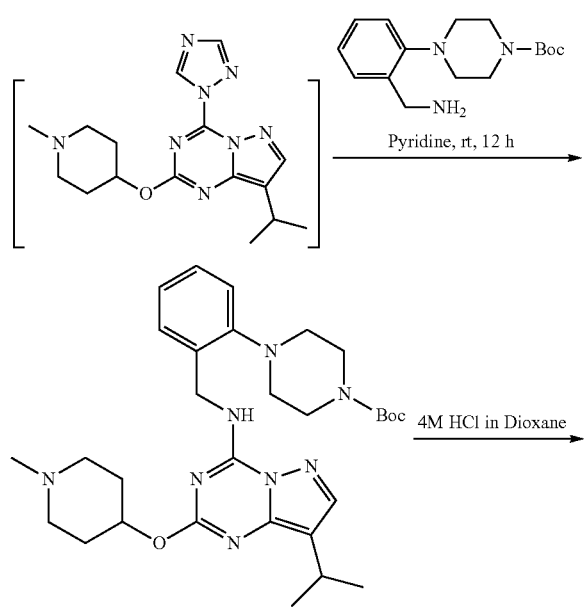

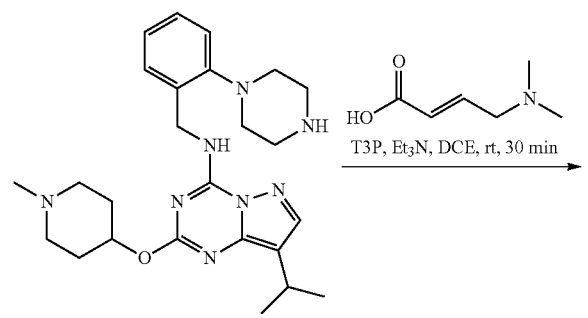

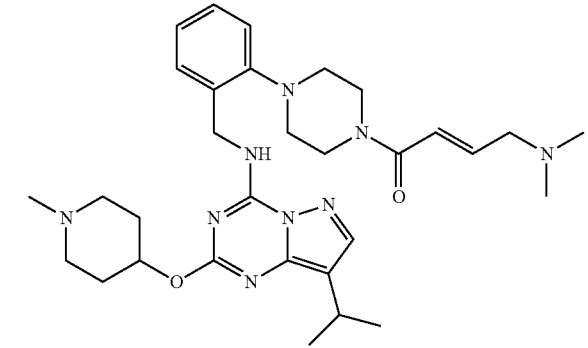

2-(Piperazin-1-yl)benzonitrile

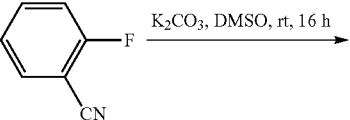

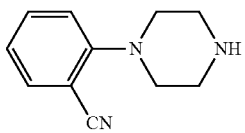

To the solution of 2-fluorobenzonitrile (5 g, 41.28 mmol) in DMSO (250 mL) was added piperazine (27.02 g, 313.76 mmol) followed by potassium carbonate (10.2 g, 73.9 mmol), and reaction was stirred at room temperature for 16 h. The reaction progress was monitored by TLC. The reaction mixture was diluted with water and toluene, and the separated organic layer was washed with 1N NaOH, dried over Na$_2$SO$_4$, and concentrated under vacuum to afford the title compound (5.2 g, yield 67%) as a colorless sticky solid which was used directly in the next step without further purification. $^1$H NMR (CDCl$_3$, 400 MHz): δ 7.57 (dd, J=1.40, 7.91 Hz, 1H), 7.44-7.52 (m, 1H), 6.96-7.05 (m, 2H), 3.16-3.23 (m, 4H), 3.04-3.13 (m, 4H), 1.75 (br. s, 1H).

tert-Butyl 4-(2-cyanophenyl)piperazine-1-carboxylate

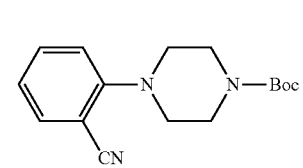

To a solution of 2-(piperazin-1-yl)benzonitrile (5 g, 26.69 mmol) in THF:H$_2$O (1:1, 100 mL) was added potassium carbonate (9.2 g, 66.7 mmol) and di-tert-butyl dicarbonate (6.4 g, 29.36 mmol) and the mixture was stirred at room temperature for 2 h. The reaction progress was monitored by TLC. Upon completion, the reaction mixture was diluted with ethyl acetate and separated. The separated organic layer was washed with saturated NaHCO$_3$ solution. The crude compound was dried over Na$_2$SO$_4$ and concentrated under vacuum to afford the title compound (6.5 g, yield 85%) as a colorless sticky solid. $^1$H NMR (CDCl$_3$, 400 MHz): δ 7.59 (d, J=7.34 Hz, 1H), 7.50 (t, J=7.83 Hz, 1H), 6.98-7.08 (m, 2H), 3.62-3.69 (m, 4H), 3.13-3.19 (m, 4H), 1.49 (s, 9H).

tert-Butyl 4-(2-(aminomethyl)phenyl)piperazine-1-carboxylate

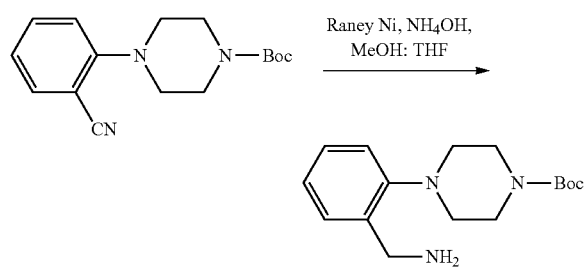

To a solution of tert-butyl 4-(2-cyanophenyl)piperazine-1-carboxylate (1.5 g, 5.22 mmol) in methanol:THF (1:1, 25 mL) was added Raney nickel (~300 mg, 20% wt) and ammonium hydroxide (5 mL, 25% aq. solution). The reaction mixture was stirred at room temperature at 100 psi under hydrogen atmosphere in an autoclave for 2 weeks. The reaction mixture was then filtered through a pad of celite and the filtrate was concentrated in vacuo to afford 700 mg of the title compound as light brown solid. $^1$H NMR (DMSO-d$_6$, 400 MHz): δ 7.72 (d, J=7.45 Hz, 1H), 7.61 (t, J=7.89 Hz, 1H), 7.48 (br. s, 1H), 7.34 (br. s, 1H), 7.18 (d, J=8.33 Hz, 1H), 7.13 (t, J=7.45 Hz, 1H), 4.08 (br. s, 2H), 3.42-3.54 (m, 4H), 3.05-3.13 (m, 2H), 2.77-2.83 (m, 2H), 1.43 (s, 9H). LCMS-Condition-01: [M+H]$^+$=292.10; R$_t$=2.09 min

8-Isopropyl-2-((1-methylpiperidin-4-yl)oxy)-4-(1H-1,2,4-triazol-1-yl)pyrazolo[1,5-a][1,3,5]triazine

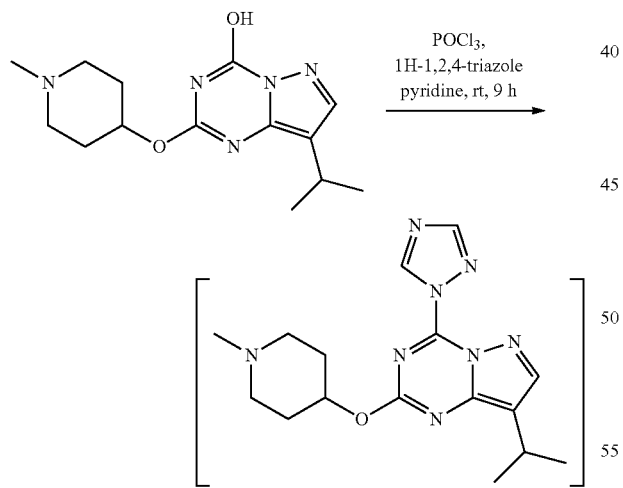

To a solution of 1H-1,2,4-triazole (427 mg, 6.18 mmol) in pyridine (1 mL) was added POCl$_3$ (0.19 mL, 2.06 mmol) and the mixture was stirred at room temperature for 1.5 h. 8-isopropyl-2-((1-methylpiperidin-4-yl)oxy)pyrazolo[1,5-a][1,3,5]triazin-4-ol (200 mg, 0.68 mmol) was then added and the reaction was stirred at room temperature for 7.5 h. The reaction progress was monitored by LCMS. The reaction mixture containing the title was used directly in the next step without work-up. LCMS: [M+H]$^+$=343.10; R$_t$=1.85 min tert-Butyl 4-(2-(((8-isopropyl-2-((1-methylpiperidin-4-yl)oxy)pyrazolo[1,5-a][1,3,5]triazin-4-yl)amino)methyl)phenyl)piperazine-1-carboxylate

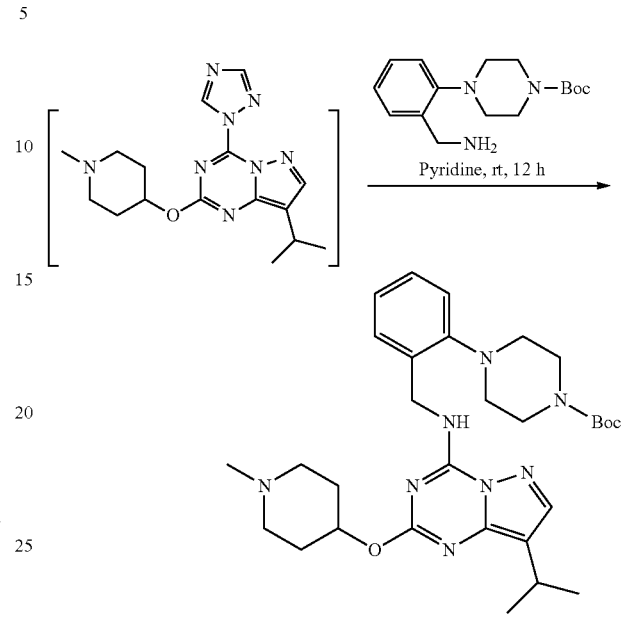

To a solution of 8-isopropyl-2-((1-methylpiperidin-4-yl)oxy)-4-(1H-1,2,4-triazol-1-yl)pyrazolo[1,5-a][1,3,5]triazine (235 mg, 0.68 mmol) in pyridine (2 mL) was added tert-butyl 4-(2-(aminomethyl)phenyl)piperazine-1-carboxylate (599 mg, 2.06 mmol) and stirred at room temperature for 12 h. The reaction progress was monitored by TLC. The reaction mixture was concentrated under vacuum to give in the crude compound, which was purified by column chromatography on neutral silica gel using 5-10% methanol in DCM to afford the title compound (250 mg, yield 64%) as a light brown solid. $^1$H NMR (DMSO-d$_6$, 400 MHz): δ 9.15 (br. s, 1H), 7.95 (s, 1H), 7.25 (d, J=7.34 Hz, 2H), 7.19 (d, J=7.34 Hz, 1H), 7.07 (t, J=7.58 Hz, 1H), 5.00 (br. s, 1H), 4.78 (d, J=5.38 Hz, 2H), 3.45-3.56 (m, 4H), 3.39 (d, J=6.36 Hz, 1H), 2.93-3.07 (m, 2H), 2.80-2.89 (m, 6H), 1.69-2.14 (m, 5H), 1.43 (s, 9H), 1.27 (m, 7H), 1.09 (t, J=7.09 Hz, 1H). LCMS: [M+H]$^+$=565.25; R$_t$=2.86 min

8-Isopropyl-2-((1-methylpiperidin-4-yl)oxy)-N-(2-(piperazin-1-yl)benzyl)pyrazolo[1,5-a][1,3,5]triazin-4-amine

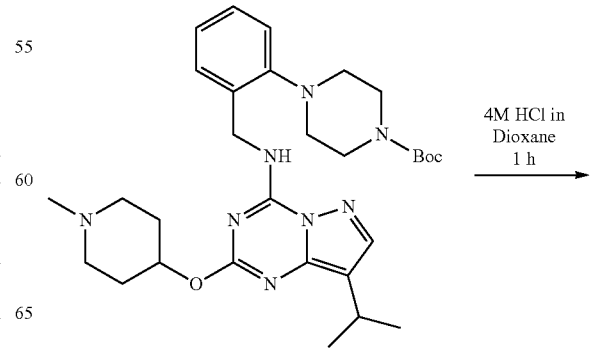

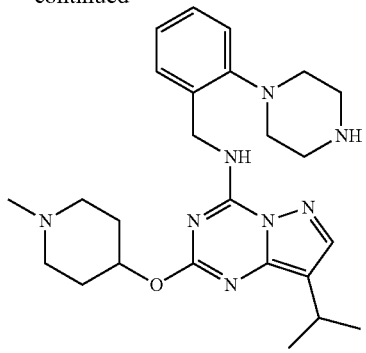

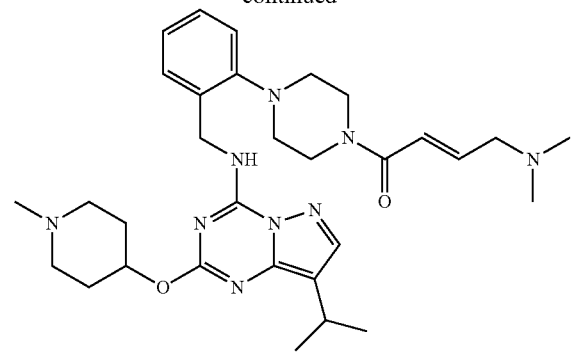

To the solution of tert-butyl 4-(2-(((8-isopropyl-2-((1-methylpiperidin-4-yl)oxy)pyrazolo[1,5-a][1,3,5]triazin-4-yl)amino)methyl)phenyl)piperazine-1-carboxylate (250 mg, 0.44 mmol) in dioxane (2 mL) was added 4M HCl in dioxane (1 mL) and the reaction was stirred at room temperature for 1 h. The reaction was monitored by TLC, and once completed, was concentrated under vacuum. The solid residue was triturated with ether and dried, then dissolved in ethyl acetate and washed with saturated aqueous NaHCO$_3$ solution. The crude compound was dried over Na$_2$SO$_4$ and concentrated under vacuum to afford the title compound (150 mg, yield 73%) as a light brown solid. The crude compound was used in the next step without further purification. LCMS: [M+H]$^+$=465.20; R$_t$=1.79

(E)-4-(Dimethylamino)-1-(4-(2-(((8-isopropyl-2-((1-methyl piperidin-4-yl)oxy)pyrazolo[1,5-a][1,3,5]triazin-4-yl)amino)methyl)phenyl)piperazin-1-yl)but-2-en-1-one (Compound 105)

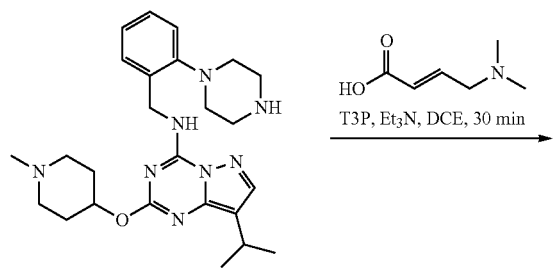

To a solution of 8-isopropyl-2-((1-methylpiperidin-4-yl)oxy)-N-(2-(piperazin-1-yl)benzyl)pyrazolo[1,5-a][1,3,5]triazin-4-amine (100 mg, 0.32 mmol) and (E)-4-(dimethylamino)but-2-enoic acid (53 mg, 0.32 mmol) in DCE (3 mL) was added triethylamine (0.13 mL, 0.96 mmol) followed by T$_3$P (0.75 mL, 1.17 mmol, 50% wt solution in ethyl acetate) at 0° C. and stirred at room temperature for 30 min. The reaction was monitored by TLC, and upon completion, was evaporated under vacuum to dryness. The residue was triturated with ether and dried to obtain crude material. The crude material was purified by reverse phase Combiflash column chromatography to afford the title compound (20 mg, yield 11%) as an off white solid. $^1$H NMR (CD$_3$OD, 400 MHz): δ 7.85 (s, 1H), 7.23-7.36 m, 3H), 7.14 (t, J=6.85 Hz, 1H), 6.72-6.84 (m, 2H), 5.21 (br. s, 1H), 4.93 (s, 2H), 3.81-3.87 (m, 3H), 2.86-3.17 (m, 10H), 2.63 (s, 3H), 2.40 (s, 6H), 2.26 (s, 1H), 1.98-2.20 (m, 4H), 1.46-1.67 (m, 1H), 1.31 (d, J=6.85 Hz, 6H). LCMS: [M+H]$^+$=576.25; R$_t$=1.84 min Example 5: 1-(3-Acrylamidobenzoyl)-N-(5-(((5-(tert-butyl)oxazol-2-yl)methyl)thio)thiazol-2-yl)piperidine-4-carboxamide (Compound 117)

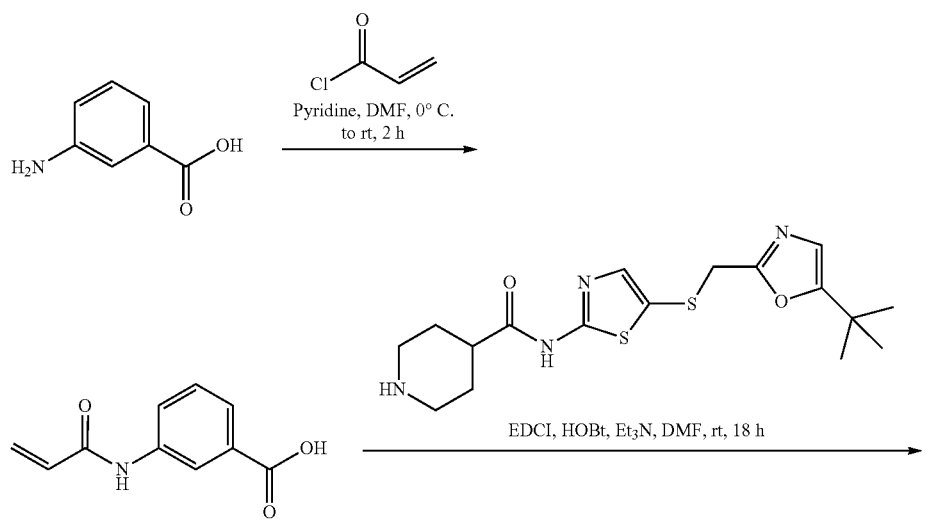

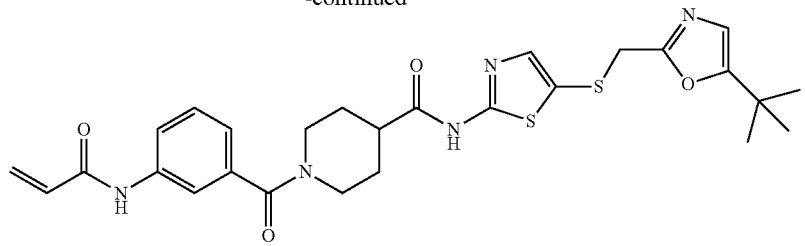

3-Acrylamidobenzoic Acid

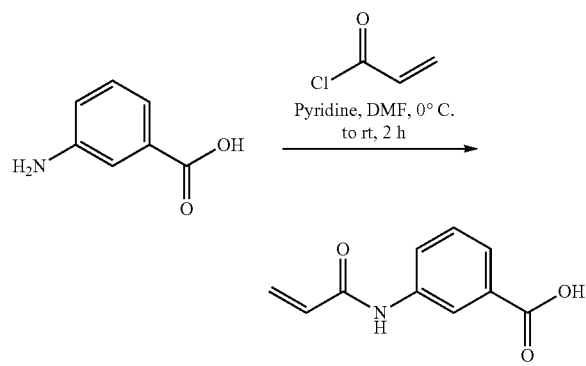

To the solution of 3-aminobenzoic acid (1 g, 7.29 mmol) and pyridine (0.4 mL) in DMF (7 mL) at 0° C. was added acryloyl chloride (0.59 mL, 7.29 mmol), and the reaction was stirred at room temperature for 2 h. The reaction progress was monitored by TLC. The reaction mixture was poured in water (20 mL) and extracted with ethyl acetate (3×20 mL). The combined organic solvents were washed with water (20 mL), dried over $Na_2SO_4$ and concentrated under vacuum to afford the title compound (821 mg, yield 59%) as an off white solid which was used directly in the next step without further purification. $^1$H NMR (DMSO-$d_6$, 400 MHz): δ 13.02 (br. s, 1H), 10.33 (s, 1H), 8.29 (s, 1H), 7.92 (d, J=8.31 Hz, 1H), 7.65 (d, J=7.83 Hz, 1H), 7.45 (t, J=7.83 Hz, 1H), 6.38-6.50 (m, 1H), 6.24-6.34 (m, 1H), 5.79 (dd, J=1.47, 10.27 Hz, 1H). LCMS: [M+H]$^+$=191.85; $R_t$=0.49 min

1-(3-Acrylamidobenzoyl)-N-(5-(((5-(tert-butyl)oxazol-2-yl)methyl)thio)thiazol-2-yl)piperidine-4-carboxamide

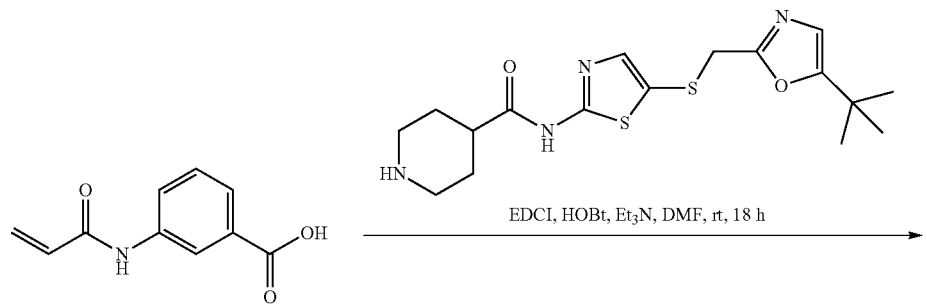

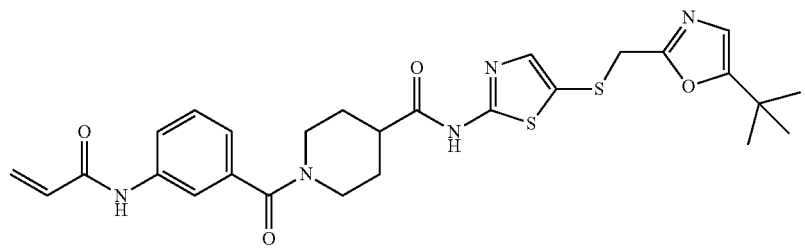

To a solution of 3-acrylamidobenzoic acid (70 mg, 0.36 mmol) in DMF (1 mL) was added triethyl amine (0.15 mL, 1.09 mmol), EDCI (105 mg, 0.54 mmol) and HOBt (74 mg, 0.54 mmol) and the reaction was stirred at room temperature for 15 min. To the resulting solution was added N-(5-(((5-(tert-butyl)oxazol-2-yl)methyl)thio)thiazol-2-yl)piperidine-4-carboxamide (139 mg, 0.36 mmol) and the reaction was further stirred at room temperature for 18 h. The reaction mixture was poured into ice water and extracted with ethyl acetate (3×20 mL). The combined organic solvents were dried over Na$_2$SO$_4$. After removal of the solvent, the residue was purified by preparative HPLC to afford the title compound (45 mg, yield 22%) as a white solid. $^1$H NMR (DMSO-d$_6$, 400 MHz): δ 12.32 (br. s, 1H), 10.28 (s, 1H), 7.76 (s, 1H), 7.69 (d, J=8.21 Hz, 1H), 7.37-7.43 (m, 2H), 7.09 (d, J=7.54 Hz, 1H), 6.72 (s, 1H), 6.41 (d, J=9.98 Hz, 1H), 6.30 (d, J=2.00 Hz, 1H), 5.76-5.81 (m, 1H), 4.46 (br. s, 1H), 4.06 (s, 2H), 3.67 (br. s, 1H), 3.06 (br. s, 1H), 2.74-2.86 (m, 2H), 1.71-1.97 (m, 2H), 1.53-1.62 (m, 2H), 1.18 (s, 9H). LCMS: [M+H]$^+$=554.15; R$_t$=2.68 min.

Example 6: Synthesis of 1-acryloyl-N-(5-(((5-(tert-butyl)oxazol-2-yl)methyl)thio)thiazol-2-yl)piperidine-4-carboxamide (Compound 116)

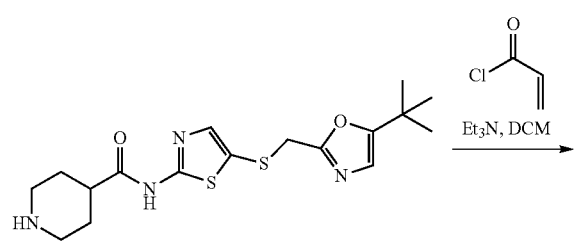

-continued

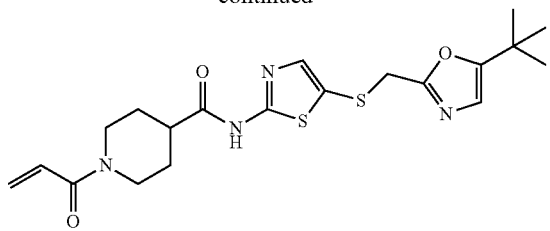

N-(5-(((5-(tert-butyl)oxazol-2-yl)methyl)thio)thiazol-2-yl)piperidine-4-carboxamide (13 mg, 0.0342 mmol) was dissolved in dichloromethane (0.7 mL), followed by the addition of triethylamine (0.01 mL, 0.0683 mmol) and by acryloyl chloride (6 µL, 0.0683 mmol). The reaction was stirred at room temperature for 16 h. At completion, the reaction mixture was poured into sat. NaHCO$_3$ (5 mL) and extracted with dichloromethane (5 mL×3). Combined organics were dried over Na$_2$SO$_4$, filtered and concentrated. The crude residue was purified by silica gel column chromatography (0-100% EtOAc/Hexanes) to afford the title compound (0.2 mg, yield 1.2%). LCMS: [M+H]$^+$=435.15; R$_t$=2.3 min.

Example 7: 1-(3-Acrylamidobenzyl)-N-(5-(((5-(tert-butyl)oxazol-2-yl)methyl)thio)thiazol-2-yl)piperidine-4-carboxamide (Compound 118)

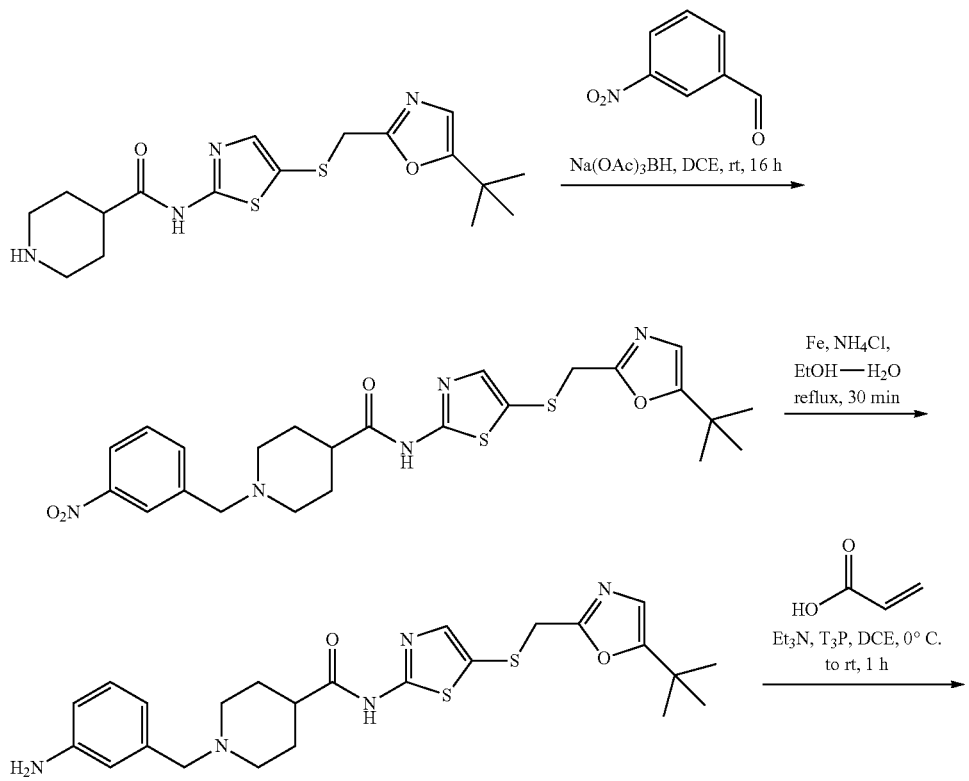

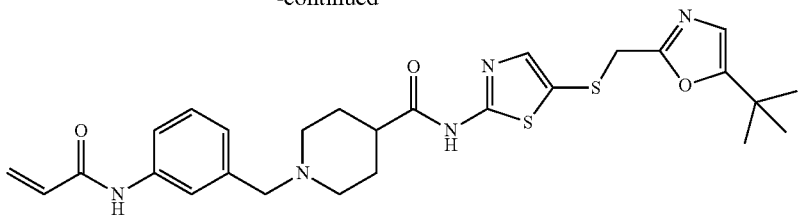

N-(5-(((5-(tert-butyl)oxazol-2-yl)methyl)thio)thiazol-2-yl)-1-(3-nitrobenzyl)piperidine-4-carboxamide

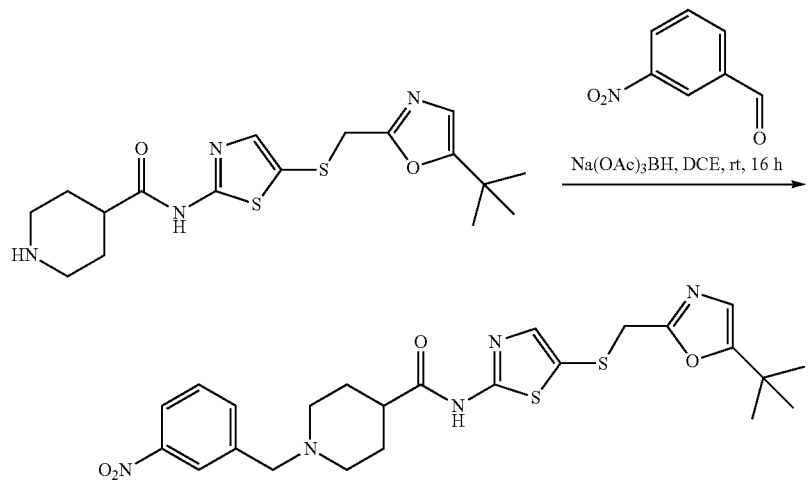

To a solution of 3-nitrobenzaldehyde (100 mg, 0.66 mmol) and N-(5-(((5-(tert-butyl)oxazol-2-yl)methyl)thio)thiazol-2-yl)piperidine-4-carboxamide, (252 mg, 0.66 mmol) in DCE (20 mL) was added sodium triacetoxyborohydride (420 mg, 1.98 mmol) portion wise and the reaction was stirred at room temperature for 16 h. After TLC indicated the reaction was complete, the mixture was diluted with DCM (30 mL) and washed with water (2×20 mL). The combined organic solvents were dried over $Na_2SO_4$ and concentrated under vacuum to afford the title compound (175 mg, yield 51%) as a yellow solid which was used directly in the next step without further purification. $^1$H NMR ($CDCl_3$, 400 MHz): δ 10.04 (br. s, 1H), 8.19 (d, J=8.48 Hz, 2H), 7.52 (d, J=8.48 Hz, 2H), 7.30-7.37 (m, 1H), 6.59 (s, 1H), 3.95 (s, 2H), 3.61 (s, 2H), 2.93 (d, J=11.47 Hz, 2H), 2.32-2.44 (m, 1H), 2.07-2.17 (m, 2H), 1.91 (d, J=3.49 Hz, 4H), 1.25 (s, 9H). LCMS-Condition 01: $[M+H]^+$ =516.10; $R_t$=2.29 min.

1-(3-Aminobenzyl)-N-(5-(((5-(tert-butyl)oxazol-2-yl)methyl)thio)thiazol-2-yl)piperidine-4-carboxamide

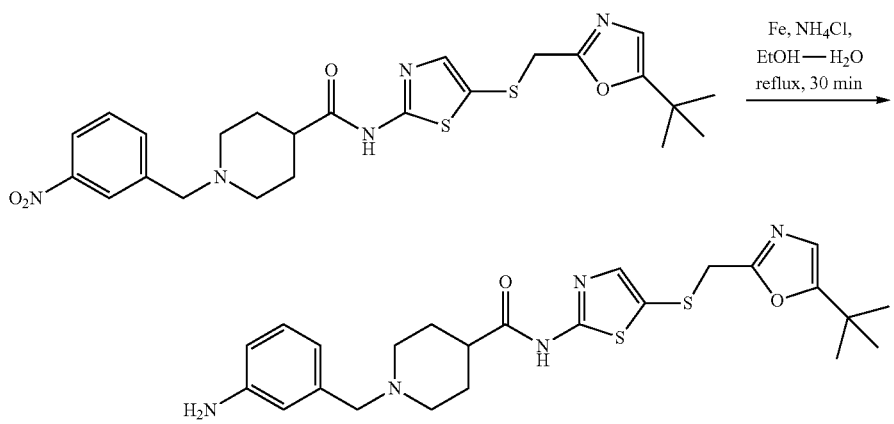

To a solution of N-(5-(((5-(tert-butyl)oxazol-2-yl)methyl)thio)thiazol-2-yl)-1-(3-nitrobenzyl)piperidine-4-carboxamide (170 mg, 0.33 mmol) in EtOH:H₂O (2:1, 7 mL) was added iron powder (147 mg, 2.64 mmol), and ammonium chloride (18 mg, 0.33 mmol) at room temperature, and the mixture was refluxed for 30 min. The reaction progress was monitored by TLC. Upon completion, the reaction mixture was filtered through a pad of celite, and the filtrate was concentrated under vacuum to obtain a crude residue. The residue was dissolved in ethyl acetate (20 mL) and washed with water (2×20 mL). The combined organic solvents were dried over Na₂SO₄ and concentrated under vacuum to afford the title compound (150 mg, yield 93%) as a yellow solid which was used directly in the next step without further purification. ¹H NMR (DMSO-d₆, 400 MHz): δ 12.23 (br. s, 1H), 7.38 (s, 1H), 6.94-6.97 (m, 3H), 6.71 (s, 1H), 6.47-6.55 (m, 3H), 4.28 (d, J=5.72 Hz, 1H), 4.05 (s, 2H), 2.59-2.72 (m, 2H), 1.52-1.84 (m, 6H), 1.22-1.34 (m, 2H), 1.17 (s, 9H). LCMS: [M+H]⁺=486.15; R$_t$=2.14 min 1-(3-Acrylamidobenzyl)-N-(5-(((5-(tert-butyl)oxazol-2-yl)methyl)thio)thiazol-2-yl)piperidine-4-carboxamide To a solution of 1-(3-aminobenzyl)-N-(5-(((5-(tert-butyl)oxazol-2-yl)methyl)thio)thiazol-2-yl)piperidine-4-carboxamide (130 mg, 0.26 mmol) and acrylic acid (19 mg, 0.26 mmol) in DCE (5 mL) was added triethylamine (0.11 mL, 0.80 mmol) and T₃P (170 mg, 0.53 mmol), and the reaction was stirred at room temperature for 1 h. The reaction progress was monitored by TLC. The mixture was diluted with DCM (20 mL) and washed with water (2×20 mL). The combined organic solvents were dried over Na₂SO₄. After removal of solvent, the residue was purified by preparative HPLC to afford title compound (18 mg, yield 12%) as a white solid. 1H NMR (CDCl₃, 400 MHz): δ 8.32 (br. s, 1H), 7.50-7.74 (m, 3H), 7.29-7.35 (m, 2H), 7.10 (d, J=6.85 Hz, 1H), 6.59 (s, 1H), 6.39-6.49 (m, 1H), 6.22-6.32 (m, 1H), 5.78 (d, J=9.78 Hz, 1H), 3.95 (s, 2H), 3.68 (br. s, 2H), 3.07 (d, J=11.25 Hz, 2H), 2.74-2.76 (m, 1H), 2.23-2.53 (m, 3H), 1.91-2.10 (m, 3H), 1.25 (s, 9H). LCMS: [M+H]⁺=540.30; R$_t$=2.72 min.

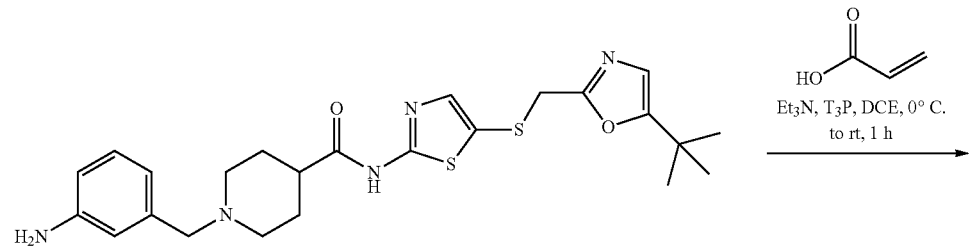

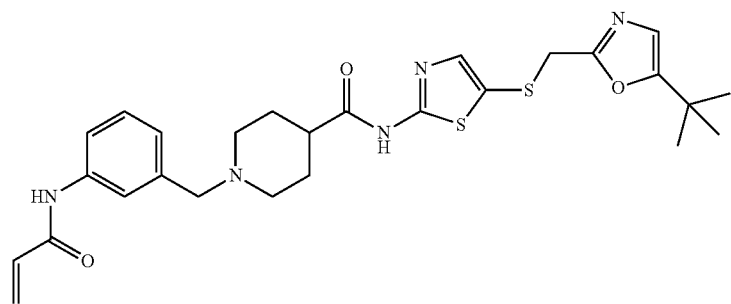

Example 8: 1-(4-Acrylamidobenzyl)-N-(5-(((5-(tert-butyl)oxazol-2-yl)methyl)thio)thiazol-2-yl)piperidine-4-carboxamide (Compound 119)

To a solution of 4-nitrobenzaldehyde (100 mg, 0.66 mmol) and N-(5-(((5-(tert-butyl)oxazol-2-yl)methyl)thio)thiazol-2-yl)piperidine-4-carboxamide (251 mg, 0.66 mmol)

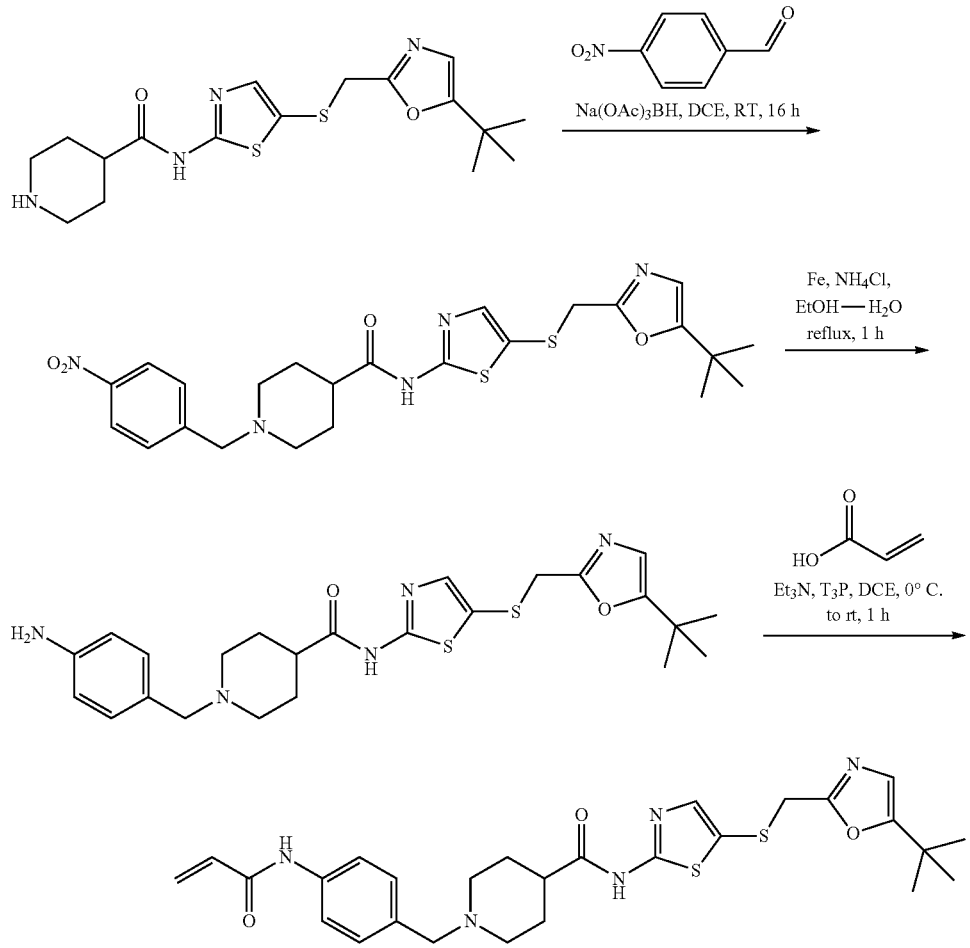

N-(5-(((5-(tert-butyl)oxazol-2-yl)methyl)thio)thiazol-2-yl)-1-(4-nitrobenzyl)piperidine-4-carboxamide in DCE (5 mL) was added sodium triacetoxyborohydride (420 mg, 1.98 mmol) portionwise and the reaction was stirred at room temperature for 16 h. The reaction progress

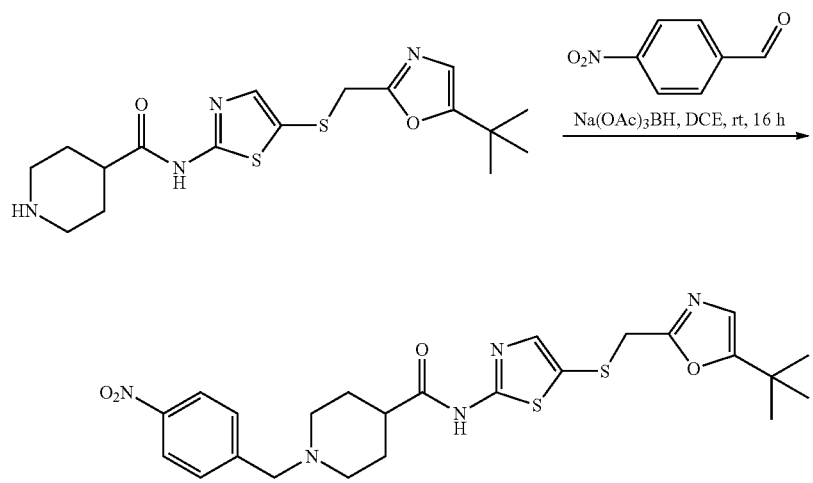 [SMILES: CC(C)(C)c1cnc(CSc2cnc(NC(=O)C3CCNCC3)s2)o1 ; O=Cc1ccc([N+](=O)[O-])cc1 ; CC(C)(C)c1cnc(CSc2cnc(NC(=O)C3CCN(Cc4ccc([N+](=O)[O-])cc4)CC3)s2)o1]

was monitored by TLC. Upon completion, the reaction mixture was diluted with DCM (30 mL) and washed with water (2×20 mL). The combined organic solvents were dried over Na$_2$SO$_4$ and concentrated under vacuum to afford the title compound (250 mg, yield 73%) as an off white solid which was used directly in the next step without further purification. LCMS: [M+H]$^+$=516.10; R$_f$=2.21 min 1-(4-Aminobenzyl)-N-(5-(((5-(tert-butyl)oxazol-2-yl)methyl)thio)thiazol-2-yl)piperidine-4-carboxamide

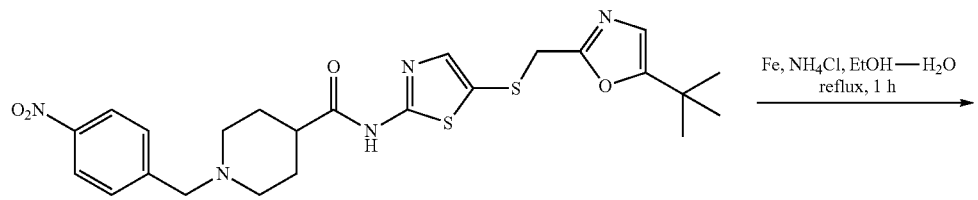

To a solution of N-(5-(((5-(tert-butyl)oxazol-2-yl)methyl)thio)thiazol-2-yl)-1-(4-nitrobenzyl)piperidine-4-carboxamide (250 mg, 0.48 mmol) in EtOH:H$_2$O (5:2, 7 mL) was added iron powder (217 mg, 3.88 mmol), ammonium chloride (26 mg, 0.48 mmol) at room temperature and further refluxed for 1 h. The reaction progress was monitored by TLC. The reaction mixture was filtered through a pad of celite, the filtrate obtained concentrated under vacuum to obtain crude residue. The residue was dissolved in ethyl acetate (20 mL) and washed with water (2×10 mL). The combined organic solvents were dried over Na$_2$SO$_4$ and concentrated under vacuum to afford the title compound (200 mg, yield 85%) as an off white solid which was used directly in the next step without further purification. $^1$H NMR (DMSO-d$_6$, 400 MHz): δ 12.23 (br. s, 1H), 7.38 (s, 1H), 6.88-7.05 (m, 3H), 6.71 (s, 1H), 6.45-6.57 (m, 3H), 4.91 (br. s, 2H), 4.28 (d, J=5.72 Hz, 1H), 4.01-4.06 (m, 3H), 3.34-3.42 (m, 2H), 2.81 (br. s, 1H), 1.54-1.86 (m, 4H), 1.17 (s, 9H). LCMS: [M+H]$^+$=486.15; R$_f$=2.18 min.

1-(4-Acrylamidobenzyl)-N-(5-(((5-(tert-butyl)oxazol-2-yl) methyl)thio)thiazol-2-yl)piperidine-4-carboxamide

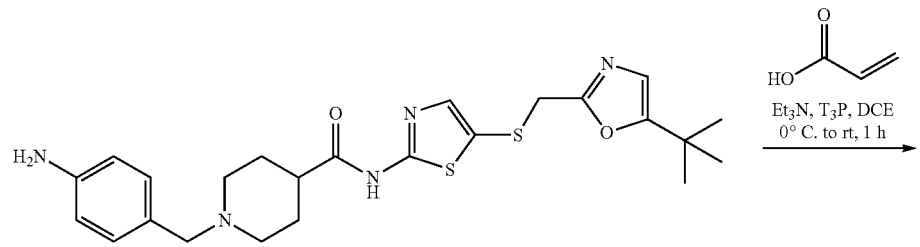

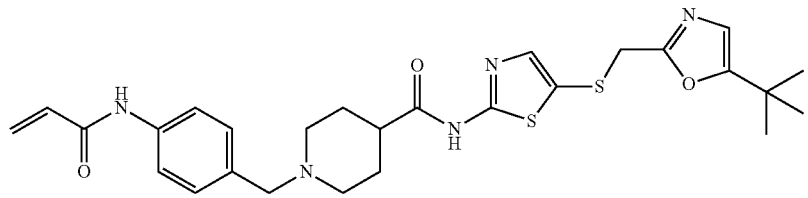

To the solution of 1-(4-aminobenzyl)-N-(5-(((5-(tert-butyl)oxazol-2-yl)methyl)thio)thiazol-2-yl)piperidine-4-carboxamide (150 mg, 0.30 mmol) and acrylic acid (22 mg, 0.30 mmol) in DCE (30 mL) was added triethylamine (0.12 mL, 0.92 mmol), 50% wt solution in ethyl acetate T$_3$P (0.25 mL, 0.39 mmol) at 0° C. and stirred at room temperature for 1 h. The reaction progress was monitored by TLC. The reaction mixture was diluted with DCM (20 mL) and washed with water (2×10 mL). The combined organic solvents were dried over Na$_2$SO$_4$. After removal of solvent, the residue was purified by preparative HPLC to afford the title compound (15 mg, yield 9%) as an off white solid. $^1$H NMR (DMSO-d$_6$, 400 MHz): δ 12.21 (br. s, 1H), 10.11 (br. s, 1H), 7.49-7.67 (m, 2H), 7.18-7.41 (m, 3H), 6.71 (s, 1H), 6.13-6.50 (m, 2H), 5.69-5.97 (m, 1H), 4.12-4.38 (m, 3H), 3.41 (br. s, 2H), 2.60-3.03 (m, 2H), 1.51-1.99 (m, 6H), 1.17 (s, 9H). LCMS: [M+H]$^+$=540.20; R$_t$=2.86 min.

Example 9: 1-((1-Acryloylpiperidin-4-yl)methyl)-N-(5-(((5-(tert-butyl)oxazol-2-yl)methyl)thio)thiazol-2-yl)piperidine-4-carboxamide (Compound 120)

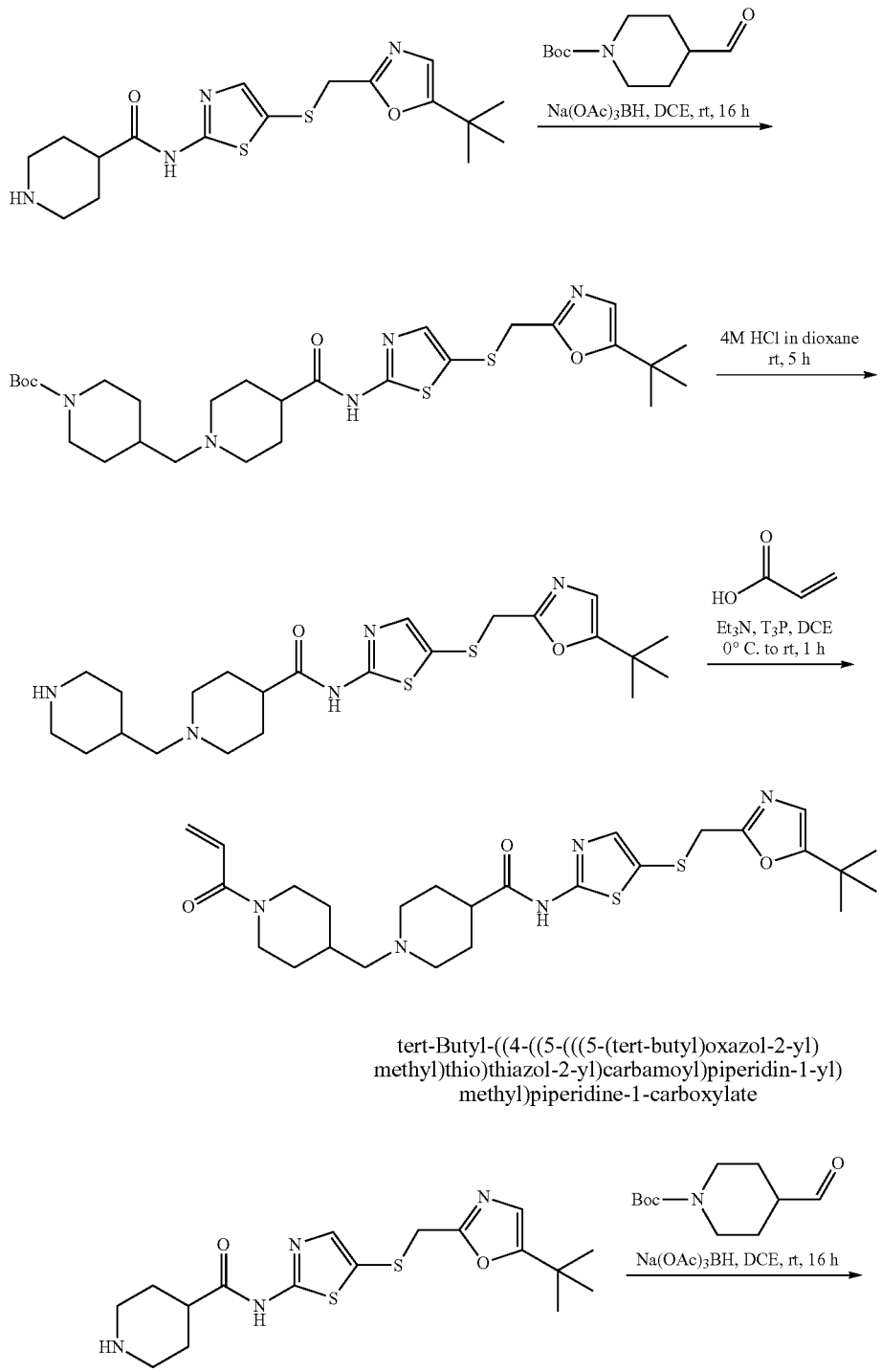

tert-Butyl-((4-((5-(((5-(tert-butyl)oxazol-2-yl)methyl)thio)thiazol-2-yl)carbamoyl)piperidin-1-yl)methyl)piperidine-1-carboxylate

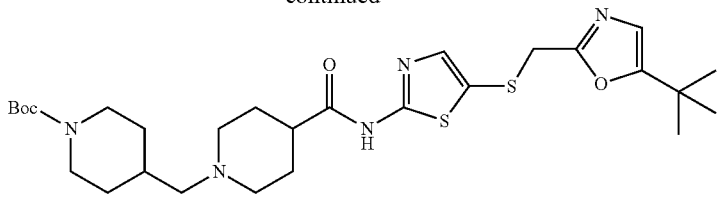

To a solution of tert-butyl 4-formylpiperidine-1-carboxylate (100 mg, 0.46 mmol) and N-(5-(((5-(tert-butyl)oxazol-2-yl)methyl)thio)thiazol-2-yl)piperidine-4-carboxamide (178 mg, 0.46 mmol) in DCE (10 mL) was added sodium triacetoxyborohydride (293 mg, 1.38 mmol) portion wise and the reaction was stirred at room temperature for 16 h. The reaction progress was monitored by TLC. The reaction mixture was diluted with DCM (30 mL) and washed with water (2×20 mL). The combined organic solvents were dried over $Na_2SO_4$ and concentrated under vacuum to afford the title compound (200 mg, yield 74%) as an off white solid which was used directly in the next step without further purification. LCMS: $[M+H]^+$=578.20; $R_t$=2.29 min N-(5-(((5-(tert-butyl)oxazol-2-yl)methyl)thio)thiazol-2-yl)-1-(piperidin-4-ylmethyl)piperidine-4-carboxamide

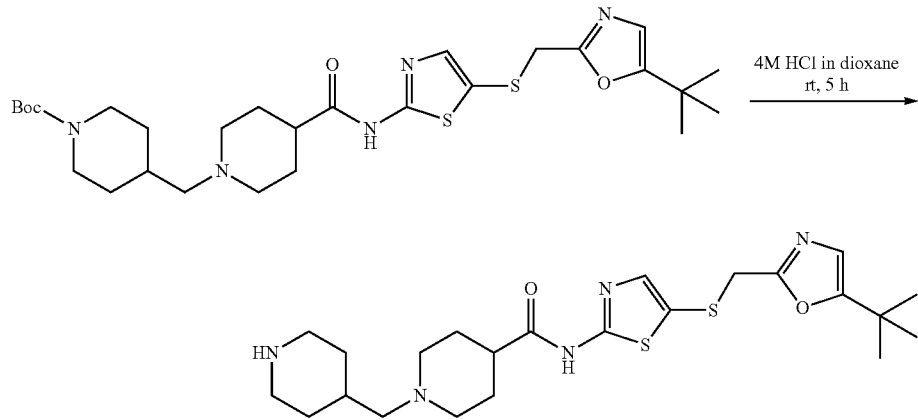

A solution of tert-butyl 4-((4-((5-(((5-(tert-butyl)oxazol-2-yl)methyl)thio)thiazol-2-yl)carbamoyl)piperidin-1-yl)methyl)piperidine-1-carboxylate (200 mg, 0.34 mmol) in 4M HCl in dioxane (2 mL) was stirred at room temperature for 5 h. The reaction progress was monitored by TLC. The reaction mixture was concentrated under vacuum to obtain crude residue which was triturated with ethyl acetate (10 mL) and dried to afford the title compound (160 mg, yield 96%) as off white solid which was used directly in the next step without further purification. LCMS: $[M+H]^+$=478.15; $R_t$=1.82 min 1-((1-Acryloylpiperidin-4-yl)methyl)-N-(5-(((5-(tert-butyl) oxazol-2-yl)methyl)thio)thiazol-2-yl)piperidine-4-carboxamide

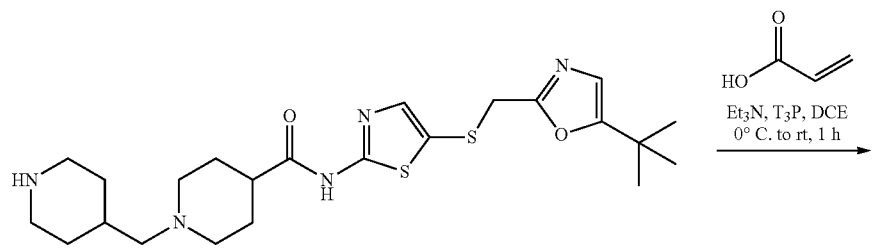

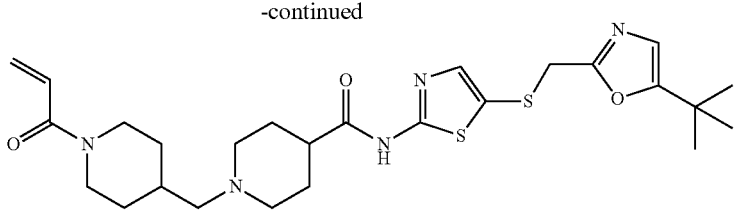

To a solution of N-(5-(((5-(tert-butyl)oxazol-2-yl)methyl)thio)thiazol-2-yl)-1-(piperidin-4-ylmethyl)piperidine-4-carboxamide (200 mg, 0.42 mmol) and acrylic acid (30 mg, 0.42 mmol) in DCE (30 mL) was added triethyl amine (0.17 mL, 1.26 mmol), T$_3$P (0.2 mL, 0.31 mmol) at 0° C. and stirred at room temperature for 1 h. The reaction progress was monitored by TLC. The reaction mixture was diluted with DCM (20 mL) and washed with water (2×10 mL). The combined organic solvents were dried over Na$_2$SO$_4$. After removal of solvent, the residue was purified by preparative HPLC to afford the title compound (15 mg, yield 7%) as off white solid. $^1$H NMR (CD$_3$OD, 400 MHz): δ 7.32 (s, 1H), 6.76 (dd, J=10.71, 16.95 Hz, 1H), 6.67 (s, 1H), 6.17 (dd, J=1.56, 16.73 Hz, 1H), 5.72 (dd, J=1.78, 10.71 Hz, 1H), 4.56 (d, J=12.49 Hz, 1H), 4.12 (d, J=13.38 Hz, 1H), 3.98 (s, 2H), 3.11-3.17 (m, 3H), 2.75 (t, J=11.82 Hz, 1H), 2.51-2.59 (m, 1H), 2.42 (d, J=6.25 Hz, 2H), 2.27-2.31 (m, 2H), 1.79-2.01 (m, 6H), 1.29-1.38 (m, 1H), 1.25 (s, 9H), 1.04-1.18 (m, 2H). LCMS: [M+H]$^+$=532.30; R$_t$=2.57 min.

Example 10: 1-(1-(3-Acrylamidophenyl)ethyl)-N-(5-(((5-(tert-butyl)oxazol-2-yl)methyl)thio)thiazol-2-yl)piperidine-4-carboxamide (Compound 121)

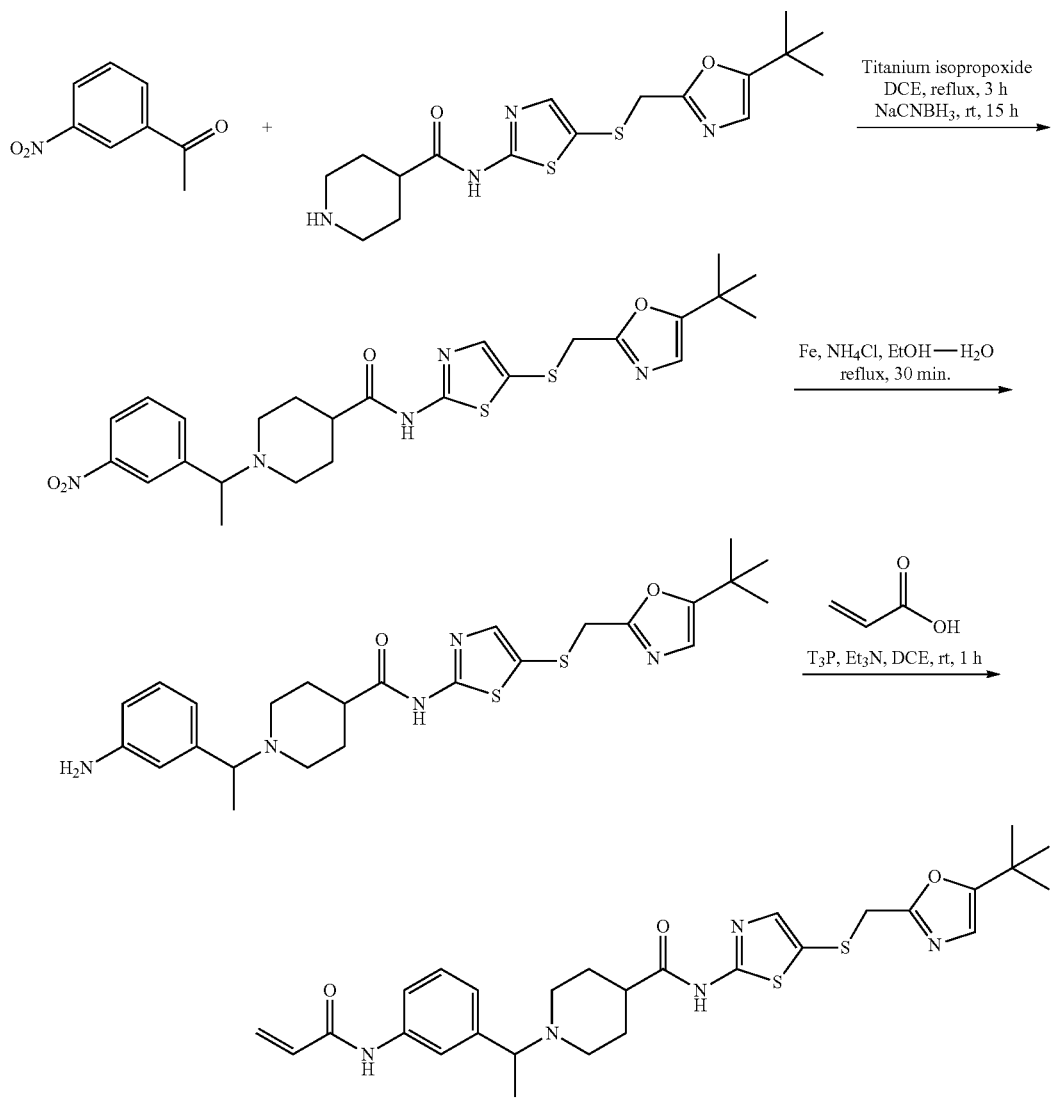

N-(5-(((5-(tert-butyl)oxazol-2-yl)methyl)thio)thiazol-2-yl)-1-(1-(3-nitrophenyl)ethyl)piperidine-4-carboxamide

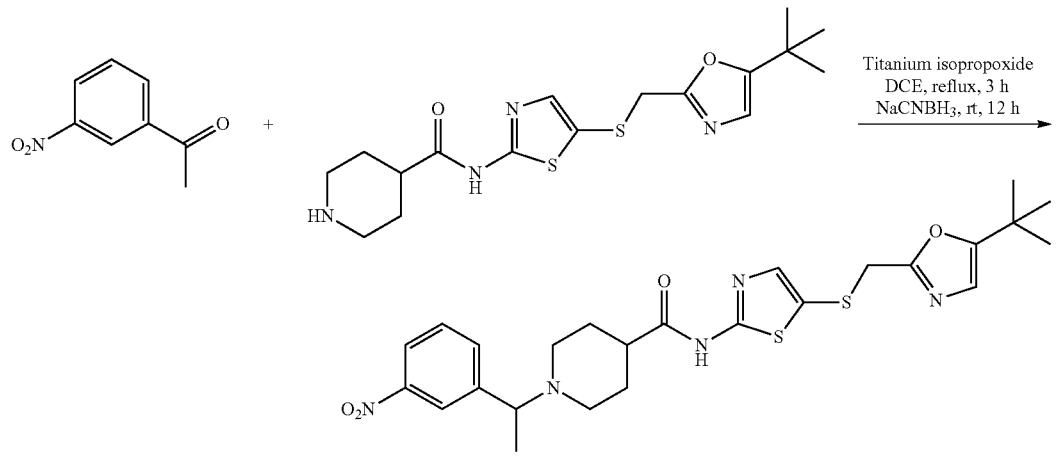

To a solution of 1-(3-nitrophenyl)ethan-1-one (150 mg, 0.91 mmol) and N-(5-(((5-(tert-butyl)oxazol-2-yl)methyl)thio)thiazol-2-yl)piperidine-4-carboxamide (345 mg, 0.91 mmol) in DCE (15 mL) was added titanium isopropoxide (294 mg, 1.03 mmol) and the reaction was refluxed for 3 h. The mixture was then allowed to cool to room temperature. To the resulting solution was added sodium cyanoborohydride (65 mg, 1.03 mmol) and the mixture was stirred at room temperature for 12 h. The reaction progress was monitored by TLC. The reaction mixture was quenched with saturated $NH_4Cl$ solution and extracted with ethyl acetate (2×20 mL). The combined organic solvents were dried over $Na_2SO_4$ and concentrated under vacuum. The crude compound was purified by silica gel column chromatography eluting with 0-50% ethyl acetate in n-hexane to afford the title compound (250 mg, yield 52%) as a brown sticky oil. LCMS: $[M+H]^+$=530.10; $R_f$=2.40 min

1-(1-(3-Aminophenyl)ethyl)-N-(5-(((5-(tert-butyl)oxazol-2-yl)methyl)thio)thiazol-2-yl)piperidine-4-carboxamide To a solution of N-(5-(((5-(tert-butyl)oxazol-2-yl)methyl)thio)thiazol-2-yl)-1-(1-(3-nitrophenyl)ethyl)piperidine-4-carboxamide (250 mg, 0.47 mmol) in EtOH:$H_2O$ (5:2, 7 mL) was added iron powder (210 mg, 3.78 mmol), and ammonium chloride (25 mg, 0.47 mmol) at room temperature, and the reaction was refluxed for 30 minutes. The reaction progress was monitored by TLC. The reaction mixture was filtered through a pad of celite and the filtrate was concentrated under vacuum to obtain crude residue. The residue was dissolved in ethyl acetate (20 mL) and washed with water (2×10 mL). The combined organic solvents were dried over $Na_2SO_4$ and concentrated under vacuum to afford the title compound (150 mg, yield 64%) as a light brown solid which was used directly in the next step without further purification. $^1H$ NMR (DMSO-$d_6$, 400 MHz): δ 7.30-7.43 (m, 2H), 7.21 (br. s, 1H), 7.08 (br. s, 2H), 6.71 (br. s, 1H), 6.56-6.67 (m, 2H), 4.20-4.40 (m, 1H), 4.05 (br. s, 2H), 3.66-3.77 (m, 1H), 3.13-3.25 (m, 2H), 2.68-2.81 (m, 3H), 2.01-2.08 (m, 2H), 1.62 (d, J=6.17 Hz, 2H), 1.21-1.24 (m, 2H), 1.17 (s, 9H). LCMS: $[M+H]^+$=500.07; $R_f$=2.27 min

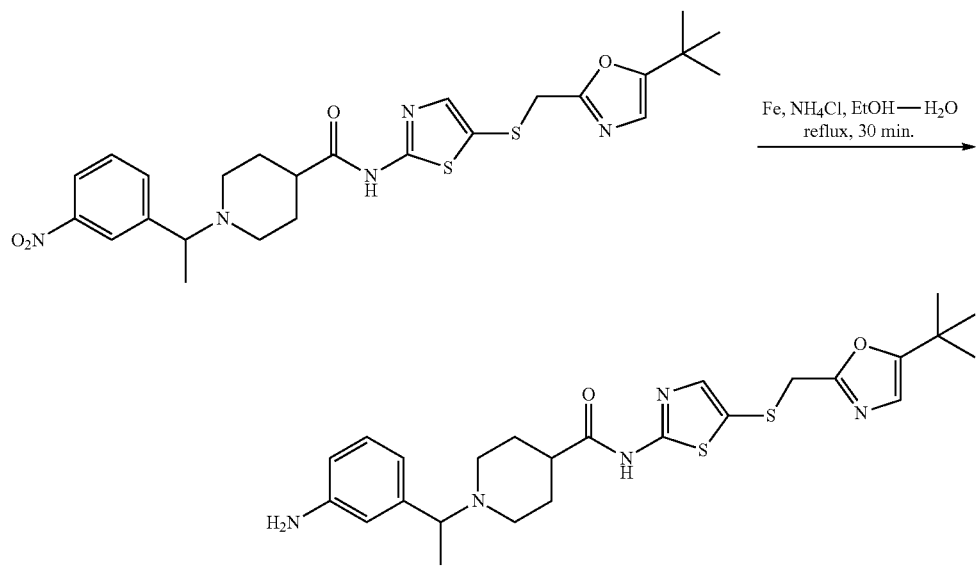

1-(1-(3-Acrylamidophenyl)ethyl)-N-(5-(((5-(tert-butyl)oxazol-2-yl)methyl)thio)thiazol-2-yl)piperidine-4-carboxamide

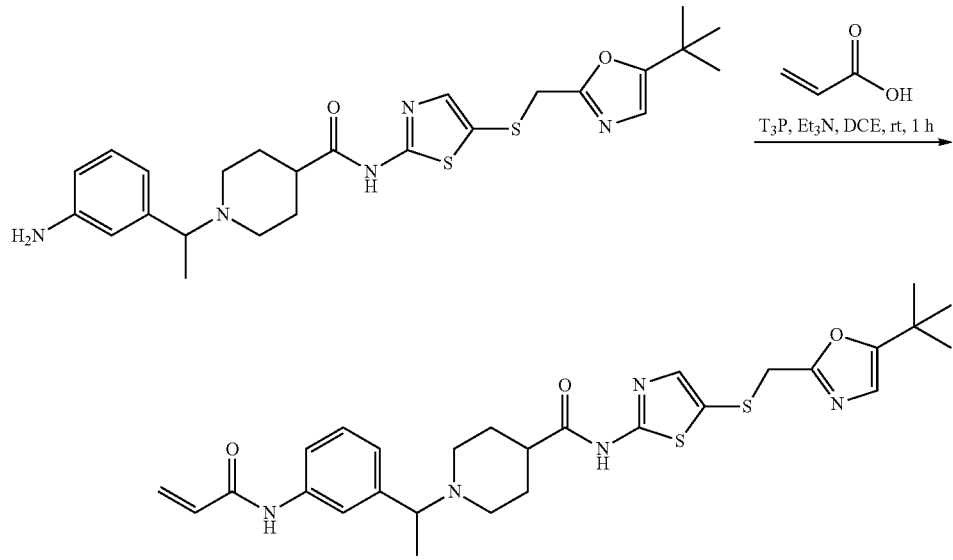

To a solution of 1-(1-(3-aminophenyl)ethyl)-N-(5-(((5-(tert-butyl)oxazol-2-yl)methyl)thio)thiazol-2-yl)piperidine-4-carboxamide (150 mg, 0.30 mmol) and acrylic acid (22 mg, 0.30 mmol) in DCE (3 mL) was added triethylamine (0.12 mL, 0.90 mmol) followed by 50% wt $T_3P$ solution in ethyl acetate (0.5 mL, 0.78 mmol) at 0° C. The reaction was stirred at room temperature for 1 h, and the reaction progress was monitored by TLC. Upon completion of the reaction, the mixture was diluted with DCM (20 mL) and washed with water (2×10 mL). The combined organic solvents were dried over $Na_2SO_4$ and concentrated. After removal of solvent, the residue was purified by preparative HPLC to afford the title compound (40 mg, yield 24%) as an off white solid. $^1$H NMR ($CD_3OD$, 400 MHz): δ 7.53-7.65 (m, 2H), 7.27-7.36 (m, 2H), 7.09-7.15 (m, 1H), 6.67 (s, 1H), 6.31-6.49 (m, 2H), 5.76-5.78 (m, 1H), 3.98 (s, 2H), 3.52 (d, J=5.87 Hz, 1H), 3.18 (d, J=10.76 Hz, 1H), 2.95 (d, J=10.27 Hz, 1H), 2.76 (t, J=5.87 Hz, 1H), 1.96-2.17 (m, 2H), 1.74-1.93 (m, 4H), 1.43 (d, J=6.36 Hz, 3H), 1.23 (s, 9H). LCMS: [M+H]$^+$=554.29; $R_t$=2.79 min Example 11: 1-(4-Acrylamidobenzoyl)-N-(5-(((5-(tert-butyl)oxazol-2-yl)methyl)thio)thiazol-2-yl)piperidine-4-carboxamide (Compound 122)

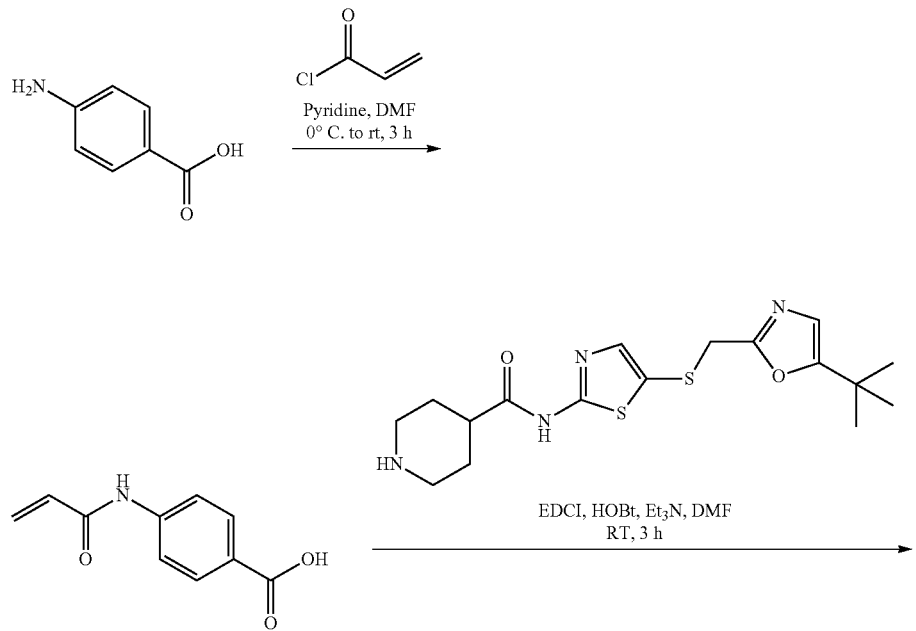

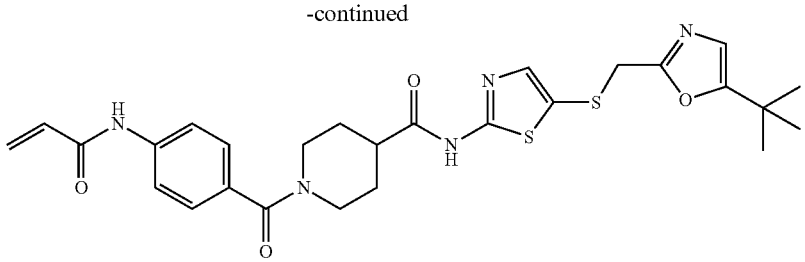

4-Acrylamidobenzoic Acid

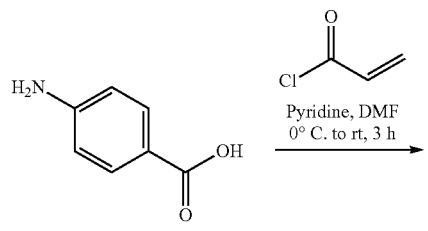

To a solution of 4-aminobenzoic acid (3 g, 21.8 mmol) in DMF (30 mL) was added pyridine (1.5 mL) followed by acryloyl chloride (1.78 mL, 21.8 mmol) drop wise and stirred at room temperature for 3 h. The reaction progress was monitored by TLC. The reaction mixture was diluted with ethyl acetate (30 mL) and washed with cold water (2×20 mL). The combined organic solvents were dried over $Na_2SO_4$ and concentrated under vacuum to afford the title compound (2.31 g, yield 56%) as off white solid which was used directly in the next step without further purification. $^1H$ NMR (DMSO-$d_6$, 400 MHz): δ 12.72 (br. s, 1H), 10.44 (s, 1H), 7.87-7.99 (m, 2H), 7.71-7.83 (m, 2H), 6.41-6.56 (m, 1H), 6.19-6.33 (m, 1H), 5.81 (dd, J=1.85, 10.17 Hz, 1H). LCMS: [M+H]$^+$=191.85; $R_f$=0.45 min.

1-(4-Acrylamidobenzoyl)-N-(5-(((5-(tert-butyl)oxazol-2-yl)methyl)thio)thiazol-2-yl)piperidine-4-carboxamide

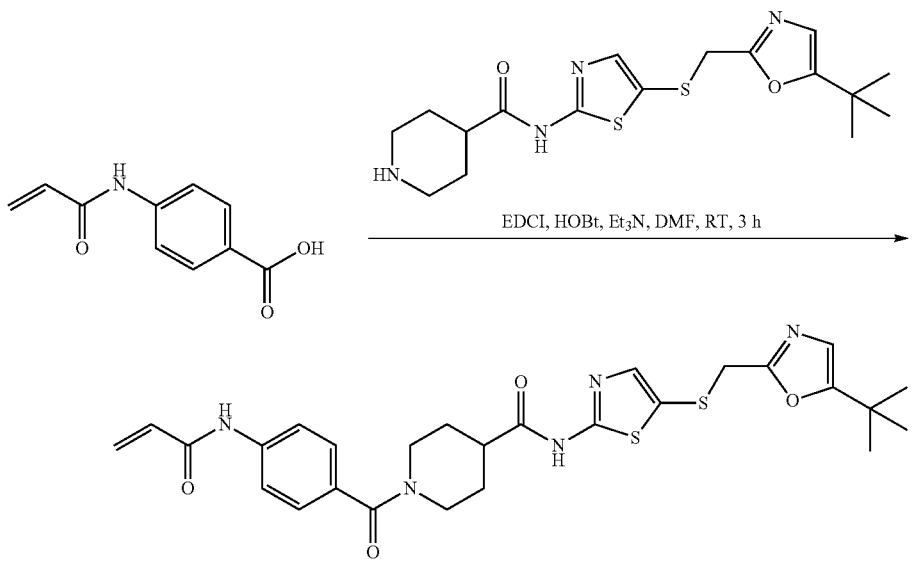

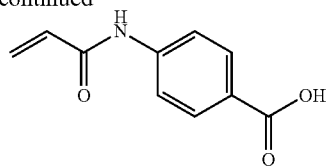

To a solution of 4-acrylamidobenzoic acid (50 mg, 0.26 mmol) in DMF (1 mL) was added triethylamine (0.1 mL, 0.78 mmol), EDCI (75 mg, 0.39 mmol) and HOBt (53 mg, 0.39 mmol). The reaction was stirred at 0° C. for 30 min, after which was added N-(5-(((5-(tert-butyl)oxazol-2-yl)methyl)thio)thiazol-2-yl)piperidine-4-carboxamide (99 mg, 0.26 mmol). After stirring at room temperature for 3 h, the mixture was diluted with water (10 mL) and extracted with ethyl acetate (3×10 mL). The combined organic solvents were dried over $Na_2SO_4$. After removal of the solvent, the residue was purified by silica gel column chromatography eluting with 0-4% methanol in DCM to afford the title compound (35 mg, yield 24%) as a white solid. $^1H$ NMR (CDCl$_3$, 400 MHz): δ 10.56 (br. s, 1H), 7.83 (br. s, 1H), 7.60 (d, J=8.31 Hz, 2H), 7.38 (d, J=7.34 Hz, 2H), 7.31 (s, 1H), 6.59 (s, 1H), 6.42-6.52 (m, 1H), 6.23-6.35 (m, 1H), 5.80 (d, J=10.27 Hz, 1H), 3.98 (s, 2H), 3.03-3.07 (m, 2H), 2.65-2.67 (m, 1H), 1.78-2.04 (m, 4H), 1.26-1.31 (m, 11H). LCMS: [M+H]+=554.05; R$_f$=2.67 min Example 12: 1-(1-Acryloylpiperidine-4-carbonyl)-N-(5-(((5-(tert-butyl)oxazol-2-yl)methyl)thio)thiazol-2-yl)piperidine-4-carboxamide (Compound 123)

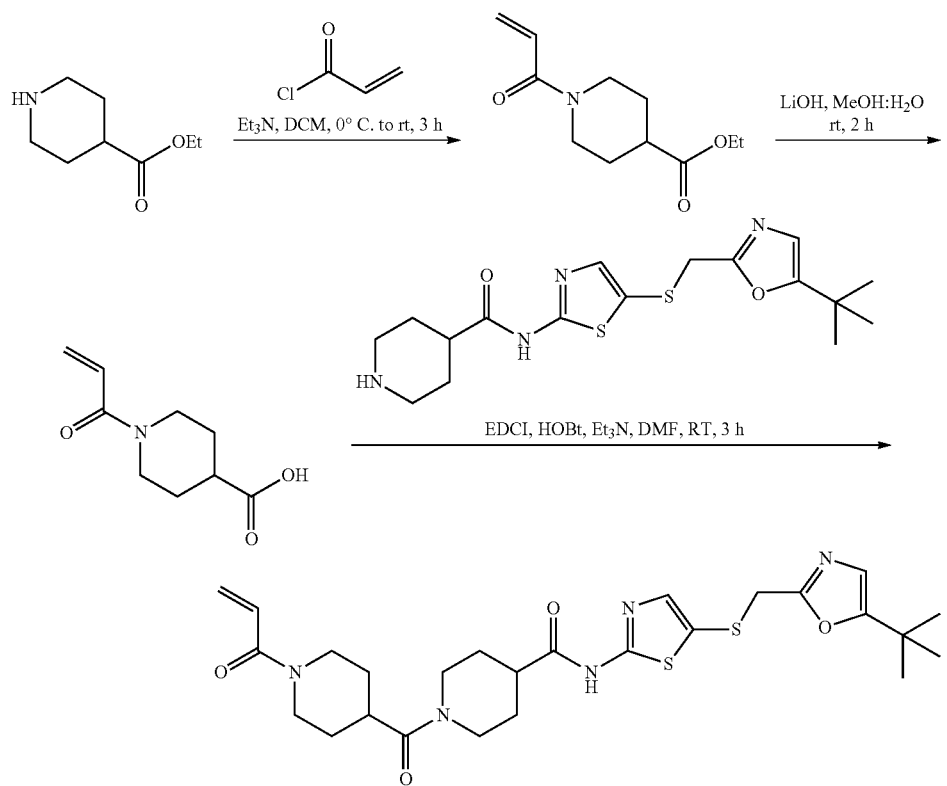

Ethyl 1-acryloylpiperidine-4-carboxylate

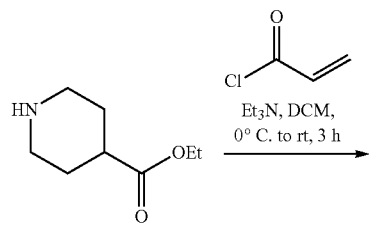

To a solution of ethyl piperidine-4-carboxylate (1 g, 6.36 mmol) in DCM (10 mL) at 0° C. was added triethylamine (1.5 mL, 10.8 mmol) followed by acryloyl chloride (0.62 mL, 7.63 mmol) and the reaction was stirred at room temperature for 3 h. The reaction progress was monitored by TLC. The reaction mixture was poured on ice and the solvent was concentrated under vacuum. The slurry obtained was extracted with ethyl acetate (2×20 mL). The combined organic solvents were washed with 1% HCl solution followed by brine, dried over Na$_2$SO$_4$ and concentrated under vacuum to afford the title compound (950 mg, yield 71%) as a straw colored solid which was used directly in the next step without further purification. $^1$H NMR (CDCl$_3$, 400 MHz): δ 6.50-6.62 (m, 1H), 6.20-6.32 (m, 1H), 5.68 (dd, J=1.96, 10.76 Hz, 1H), 4.15 (q, J=7.17 Hz, 2H), 3.84-4.04 (m, 1H), 2.87-3.31 (m, 2H), 2.56 (tt, J=3.97, 10.70 Hz, 2H), 1.96 (dd, J=2.93, 13.21 Hz, 2H), 1.62-1.81 (m, 2H), 1.18-1.33 (m, 3H). LCMS: [M+H]+=211.97; R$_f$=2.20 min.

1-Acryloylpiperidine-4-carboxylic Acid

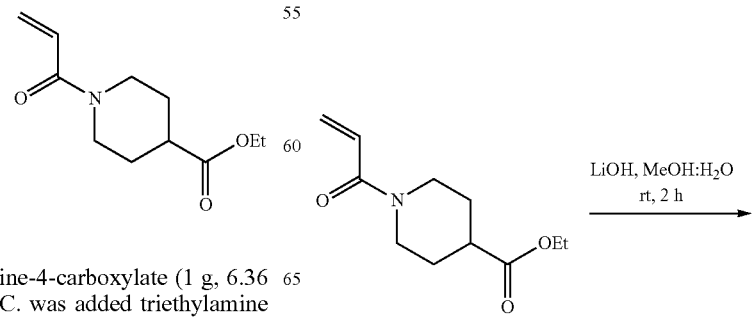

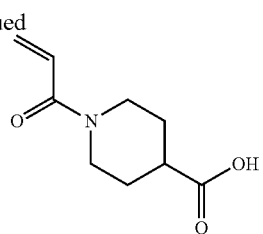

To a solution of ethyl 1-acryloylpiperidine-4-carboxylate (300 mg, 1.42 mmol) in MeOH:H$_2$O (3:3 mL) was added solution of lithium hydroxide (170 mg, 7.09 mmol) in water (2 mL) and stirred at room temperature for 2 h. The reaction mixture was acidified with 1N HCl and extracted with ethyl acetate (3×15 mL). The combined organic solvents were dried over Na$_2$SO$_4$ and concentrated under vacuum to afford the title compound (200 mg, yield 77%) as an off white solid which was used directly in the next step without further purification. $^1$H NMR (CDCl$_3$, 400 MHz): δ 6.57 (dd, J=10.52, 16.66 Hz, 1H), 6.27 (d, J=16.66 Hz, 1H), 5.70 (d, J=10.52 Hz, 1H), 4.43-4.46 (m, 1H), 3.93-3.97 (m, 1H), 2.90-3.26 (m, 2H), 2.53-2.70 (m, 1H), 1.96-2.00 (m, 2H), 1.61-1.79 (m, 2H). LCMS: [M+H]$^+$=183.85; R$_t$=2.32 min.

1-(1-Acryloylpiperidine-4-carbonyl)-N-(5-((((5-(tert-butyl) oxazol-2-yl)methyl)thio)thiazol-2-yl)piperidine-4-carboxamide To a solution of 1-acryloylpiperidine-4-carboxylic acid (50 mg, 0.27 mmol) in DMF (2.5 mL) was added triethylamine (0.11 mL, 0.81 mmol), EDCI (78 mg, 0.41 mmol) and HOBt (55 mg, 0.41 mmol) and the reaction was stirred at 0° C. for 30 min. To the resulting solution was added N-(5-((((5-(tert-butyl)oxazol-2-yl) methyl)thio)thiazol-2-yl)piperidine-4-carboxamide (104 mg, 0.27 mmol) and the solution was stirred at room temperature for 3 h. The reaction mixture was diluted with water (10 mL) and extracted with ethyl acetate (3×20 mL). The combined organic solvents were dried over Na$_2$SO$_4$. After removal of solvent, the residue was purified by silica gel column chromatography eluting with 0-4% methanol in DCM to afford the title compound (40 mg, yield 27%) as a white solid. $^1$H NMR (CDCl$_3$, 400 MHz): δ 10.82 (br. S, 1H), 7.31 (s, 1H), 6.54-6.63 (m, 2H), 6.26 (d, J=16.63 Hz, 1H), 5.69 (d, J=10.76 Hz, 1H), 4.54-4.61 (m, 2H), 3.85-4.16 (m, 4H), 3.14-3.20 (m, 2H), 2.62-2.82 (m, 4H), 1.96-2.01 (m, 2H), 1.72-1.85 (m, 6H), 1.26 (s, 9H). LCMS: [M+H]$^+$=546.15; R$_t$=2.48 min

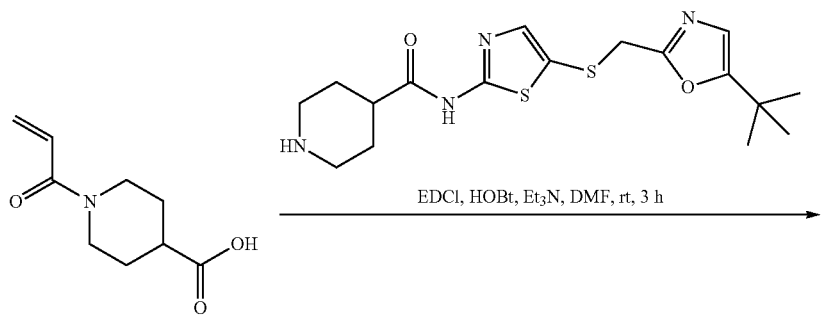

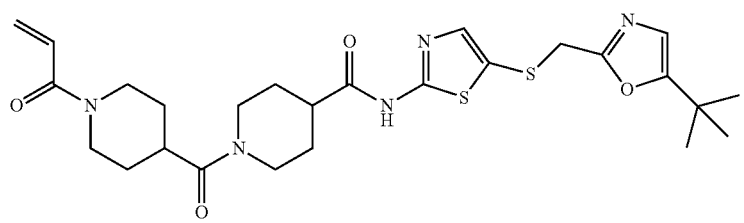

Example 13: 1-(3-Acrylamidobenzoyl)-N-(5-(((5-(tert-butyl)oxazol-2-yl)methyl)thio)thiazol-2-yl)piperidine-4-carboxamide (Compound 124)

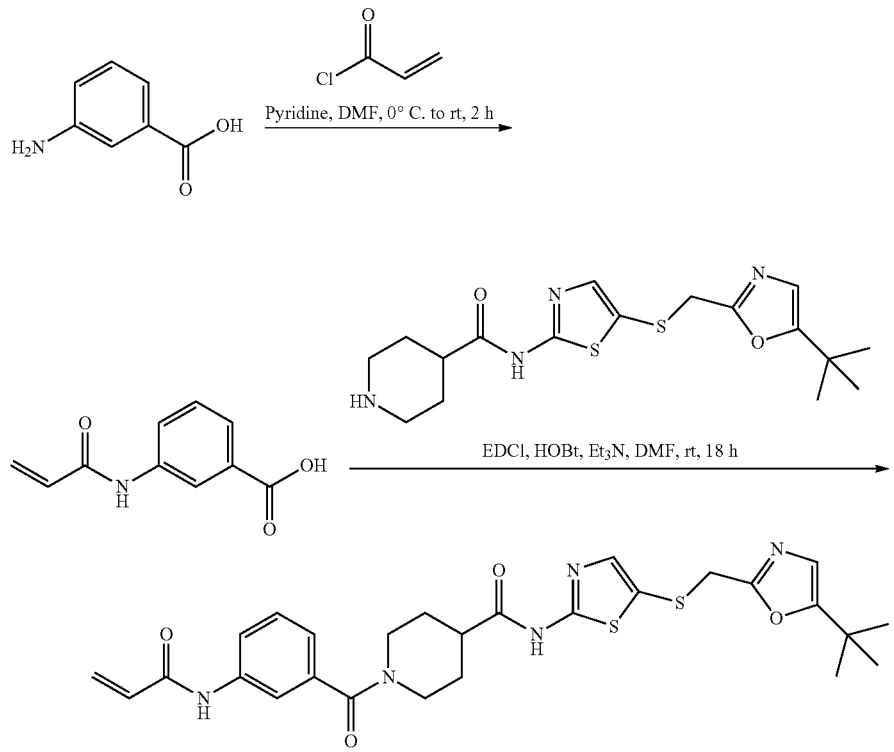

3-Acrylamidobenzoic Acid

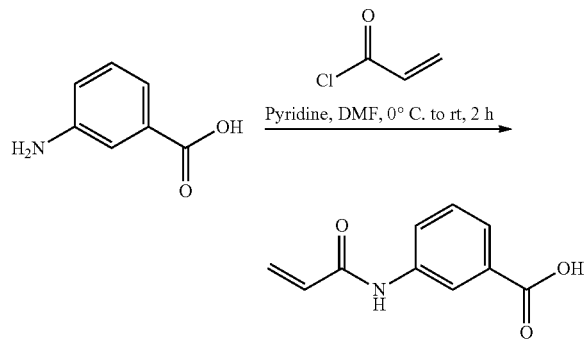

To a solution of 3-aminobenzoic acid (1 g, 7.29 mmol) and pyridine (0.4 mL) in DMF (7 mL) at 0° C. was added acryloyl chloride (0.59 mL, 7.29 mmol) and the reaction was stirred at room temperature for 2 h. The reaction progress was monitored by TLC. The reaction mixture was poured in water (20 mL) and extracted with ethyl acetate (3×20 mL). The combined organic solvents was washed with water (20 mL), dried over $Na_2SO_4$ and concentrated under vacuum to afford the title compound (821 mg, yield 59%) as an off white solid which was used directly in the next step without further purification. $^1$H NMR (DMSO-$d_6$, 400 MHz): δ 13.02 (br. s, 1H), 10.33 (s, 1H), 8.29 (s, 1H), 7.92 (d, J=8.31 Hz, 1H), 7.65 (d, J=7.83 Hz, 1H), 7.45 (t, J=7.83 Hz, 1H), 6.38-6.50 (m, 1H), 6.24-6.34 (m, 1H), 5.79 (dd, J=1.47, 10.27 Hz, 1H). LCMS: [M+H]$^+$=191.85; R$_f$=0.49 min.

1-(3-Acrylamidobenzoyl)-N-(5-(((5-(tert-butyl)oxazol-2-yl)methyl)thio)thiazol-2-yl)piperidine-4-carboxamide

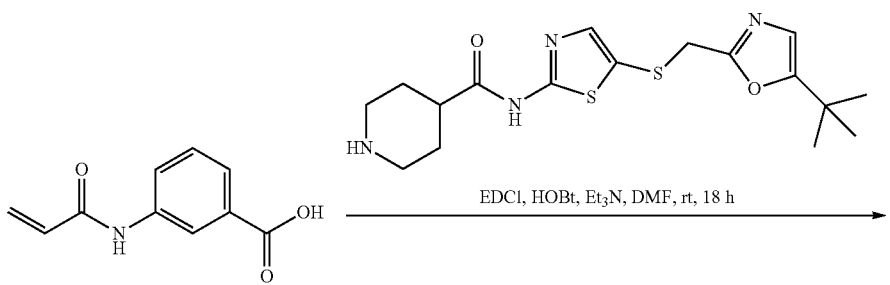

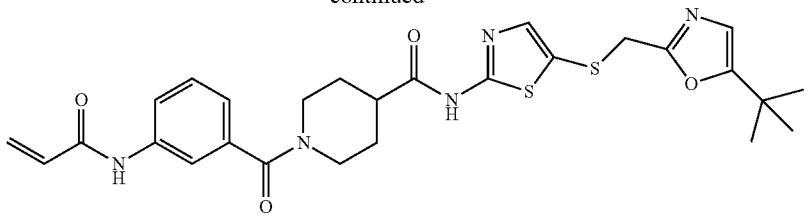

To a solution of 3-acrylamidobenzoic acid (70 mg, 0.36 mmol) in DMF (1 mL) was added triethyl amine (0.15 mL, 1.09 mmol), EDCI (105 mg, 0.54 mmol) and HOBt (74 mg, 0.54 mmol) and the reaction was stirred at room temperature for 15 min. To the resulting solution was added N-(5-(((5-(tert-butyl)oxazol-2-yl)methyl)thio)thiazol-2-yl)piperidine-4-carboxamide (139 mg, 0.36 mmol) and the mixture was stirred at room temperature for 18 h. The reaction mixture was poured into ice water and extracted with ethyl acetate (3×20 mL). The combined organic solvents were dried over Na$_2$SO$_4$. After removal of the solvent, the residue was purified by preparative HPLC to afford the title compound (45 mg, yield 22%) as a white solid. $^1$H NMR (DMSO-d$_6$, 400 MHz): δ 12.32 (br. s, 1H), 10.28 (s, 1H), 7.76 (s, 1H), 7.69 (d, J=8.21 Hz, 1H), 7.37-7.43 (m, 2H), 7.09 (d, J=7.54 Hz, 1H), 6.72 (s, 1H), 6.41 (d, J=9.98 Hz, 1H), 6.30 (d, J=2.00 Hz, 1H), 5.76-5.81 (m, 1H), 4.46 (br. s, 1H), 4.06 (s, 2H), 3.67 (br. s, 1H), 3.06 (br. s, 1H), 2.74-2.86 (m, 2H), 1.71-1.97 (m, 2H), 1.53-1.62 (m, 2H), 1.18 (s, 9H). LCMS: [M+H]$^+$=554.15; R$_t$=2.68 min Example 14: 1-((1-Acryloylpiperidin-3-yl)methyl) methyl)-N-(5-(((5-(tert-butyl)oxazol-2-yl)methyl) thio)thiazol-2-yl)piperidine-4-carboxamide (Compound 125)

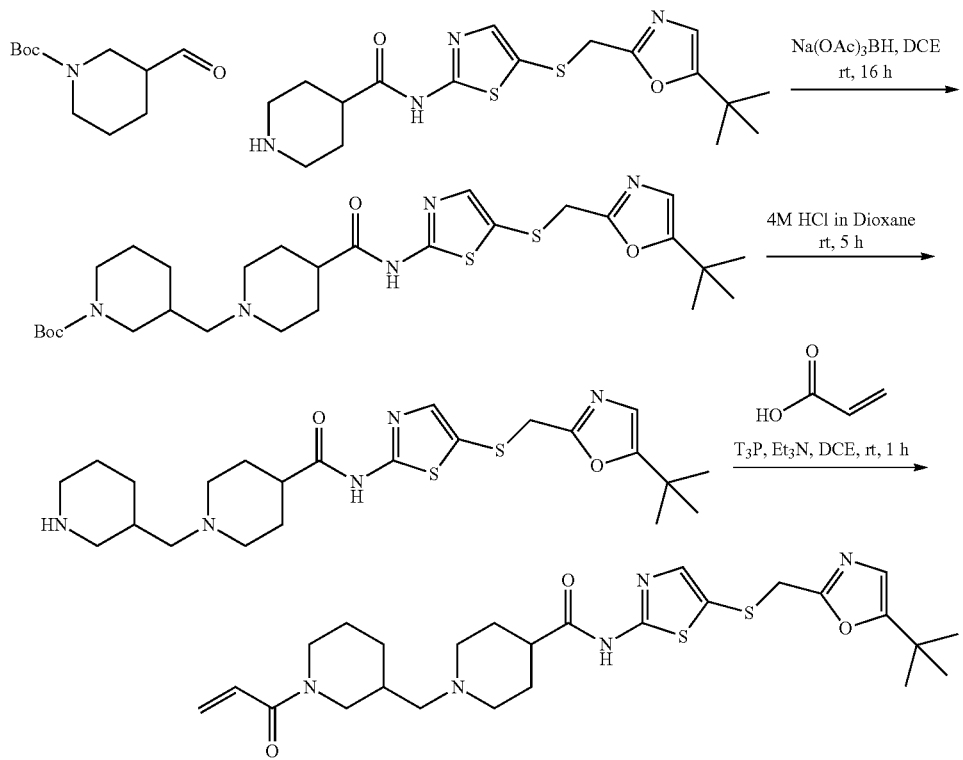

tert-Butyl 3-((4-((5-(((5-(tert-butyl)oxazol-2-yl) methyl)thio) thiazol-2-yl)carbamoyl)piperidin-1-yl) methyl)piperidine-1-carboxylate

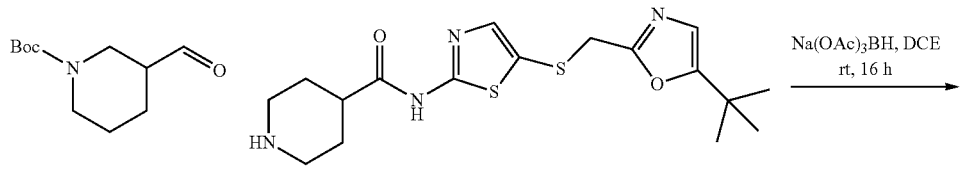

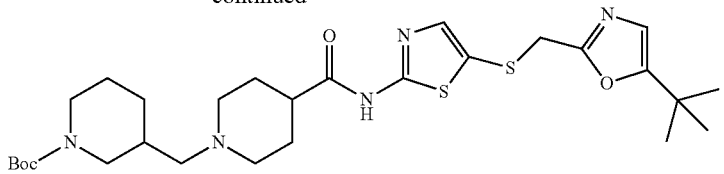

To a solution of tert-butyl 3-formylpiperidine-1-carboxylate (100 mg, 0.47 mmol) and N-(5-(((5-(tert-butyl)oxazol-2-yl)methyl)thio)thiazol-2-yl)piperidine-4-carboxamide (178 mg, 0.47 mmol) in DCE (20 mL) was added sodium triacetoxy borohydride (298 mg, 1.41 mmol) portion wise and the mixture was stirred at room temperature for 16 h. The reaction progress was monitored by TLC. The reaction mixture was diluted with water and extracted with DCM (2×20 mL). The combined organic layer was dried over $Na_2SO_4$ and concentrated under vacuum to afford the title compound (200 mg, yield 74%) as a light brown sticky liquid. The crude compound was used in the next step without further purification. $^1$H NMR (DMSO-$d_6$, 400 MHz): δ 12.22 (br. s, 1H), 7.39 (s, 1H), 6.72 (s, 1H), 4.05 (s, 2H), 3.88-3.92 (m, 1H), 3.76 (d, J=12.79 Hz, 1H), 3.17 (d, J=4.85 Hz, 1H), 2.89 (s, 1H), 2.70-2.83 (m, 3H), 2.05-2.08 (m, 2H), 1.91 (s, 3H), 1.51-1.83 (m, 7H), 1.39 (s, 9H), 1.23-1.32 (m, 1H), 1.17 (s, 9H). LCMS: $[M+H]^+$=578.20; $R_t$=2.40 min.

N-(5-(((5-(tert-butyl)oxazol-2-yl)methyl)thio)thiazol-2-yl)-1-(piperidin-3-ylmethyl)piperidine-4-carboxamide

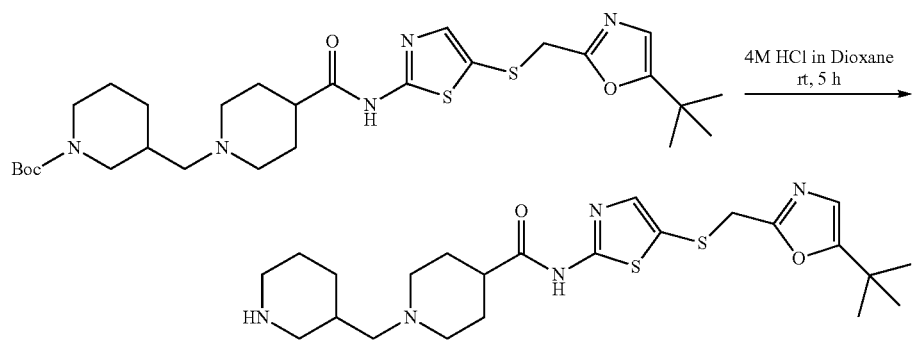

To a solution of tert-butyl 3-((4-((5-(((5-(tert-butyl)oxazol-2-yl)methyl)thio) thiazol-2-yl)carbamoyl)piperidin-1-yl)methyl)piperidine-1-carboxylate (245 mg, 0.34 mmol) in dioxane (10 mL) was added 4M HCl in dioxane (1 mL) at room temperature and stirred for 5 h. The completion of the reaction was monitored by TLC. The reaction mixture was concentrated under vacuum to obtain crude residue. The residue was washed with ethyl acetate (20 mL) and dried to afford 200 mg of the title compound as a light brown solid which was used directly in the next step without further purification. $^1$H NMR (DMSO-$d_6$, 400 MHz): δ 9.36 (br. s, 1H), 7.40 (s, 1H), 7.32 (br. s, 1H), 6.73 (s, 1H), 4.06 (s, 2H), 3.36-3.55 (m, 2H), 3.04-3.20 (m, 3H), 2.86-3.02 (m, 3H), 2.65-2.82 (m, 3H), 2.38 (br. s, 1H), 1.96-2.15 (m, 4H), 1.66-1.92 (m, 4H), 1.23-1.28 (m, 1H), 1.18 (s, 9H). LCMS: $[M+H]^+$=478.25; $R_t$=1.76 min

1-((1-Acryloylpiperidin-3-yl)methyl)-N-(5-(((5-(tert-butyl)oxazol-2-yl)methyl)thio)thiazol-2-yl)piperidine-4-carboxamide

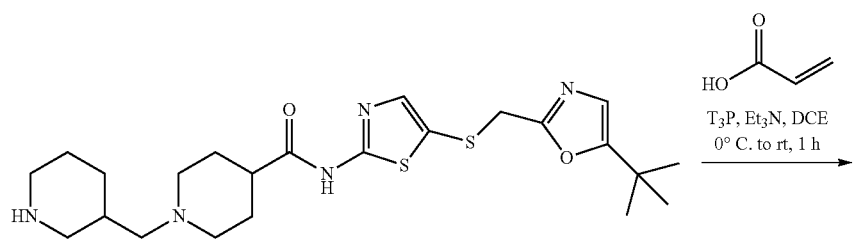

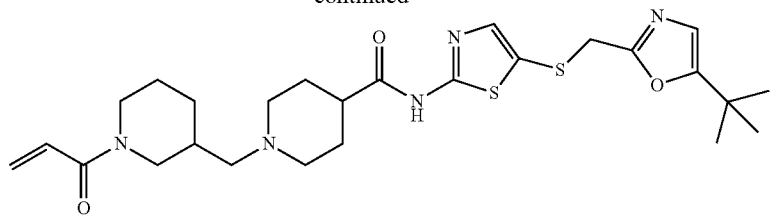

To a solution of N-(5-(((5-(tert-butyl)oxazol-2-yl)methyl)thio)thiazol-2-yl)-1-(piperidin-3-ylmethyl)piperidine-4-carboxamide (200 mg, 0.42 mmol) and acrylic acid (30 mg, 0.42 mmol) in DCE (19 mL) was added triethyl amine (0.17 mL, 1.25 mmol), $T_3P$ (2 mL, 3.14 mmol, 50% wt solution in ethyl acetate) and the mixture was stirred at room temperature for 1 h. The reaction progress was monitored by TLC. The reaction mixture was diluted with DCM (20 mL) and washed with water (2×20 mL). The combined organic solvents were dried over $Na_2SO_4$. After removal of solvent, the residue was purified by preparative HPLC to afford the title compound (70 mg, yield 31%) as a white solid. $^1$H NMR ($CD_3OD$, 400 MHz): δ 7.31 (s, 1H), 6.70-6.87 (m, 1H), 6.67 (s, 1H), 6.17 (d, J=17.12 Hz, 1H), 5.73 (t, J=9.05 Hz, 1H), 4.48 (d, J=13.69 Hz, 1H), 3.92-4.09 (m, 4H), 3.09-3.23 (m, 2H), 2.84-3.05 (m, 2H), 2.53-2.62 (m, 1H), 2.46 (d, J=6.36 Hz, 1H), 2.06-2.36 (m, 3H), 1.68-2.00 (m, 8H), 1.24 (s, 9H). LCMS: [M+H]$^+$=532.40; $R_t$=2.71 min.

Example 15: (E)-N-(5-(((5-(tert-butyl)oxazol-2-yl)methyl)thio)thiazol-2-yl)-1-(3-(4-(dimethylamino)but-2-enamido)benzyl)piperidine-4-carboxamide (Compound 127)

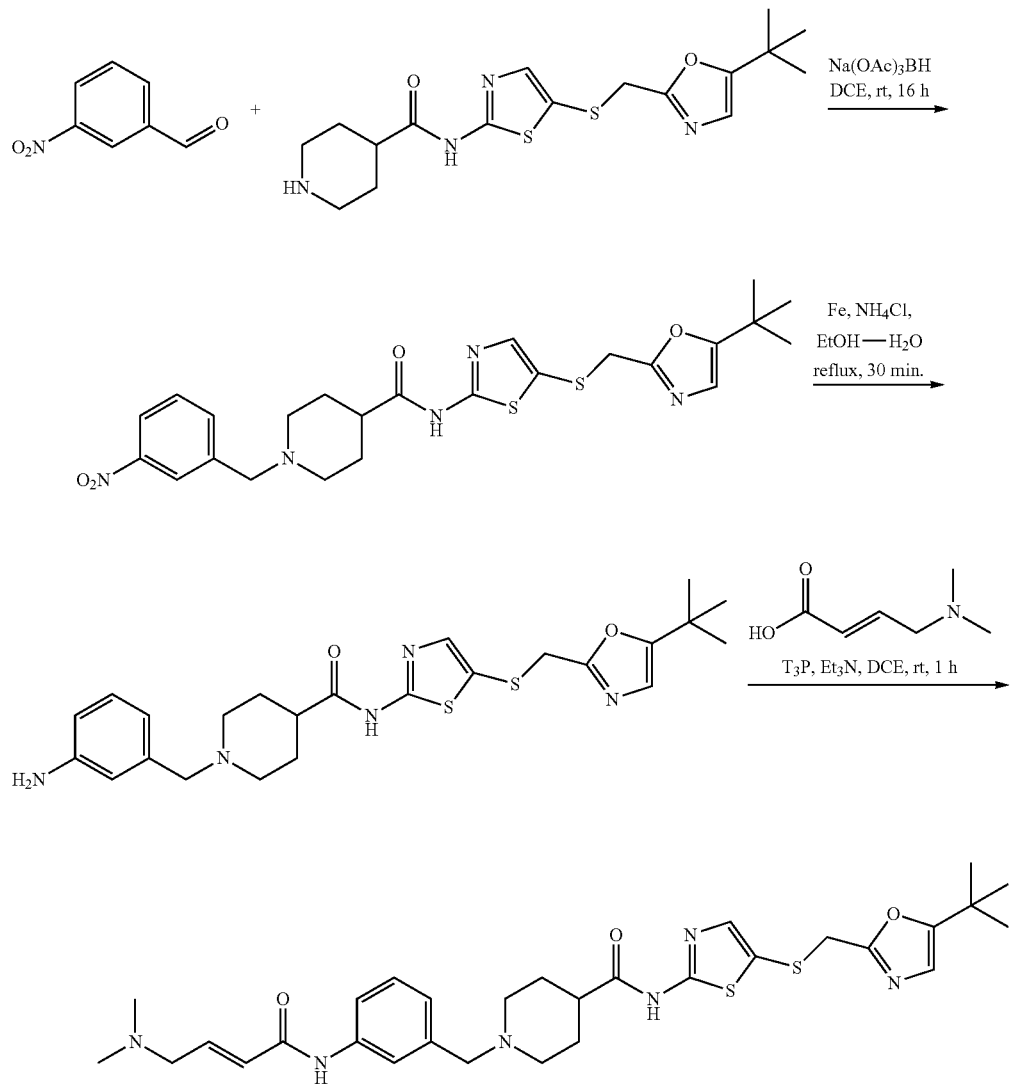

N-(5-(((5-(tert-butyl)oxazol-2-yl)methyl)thio)thiazol-2-yl)-1-(3-nitrobenzyl)piperidine-4-carboxamide

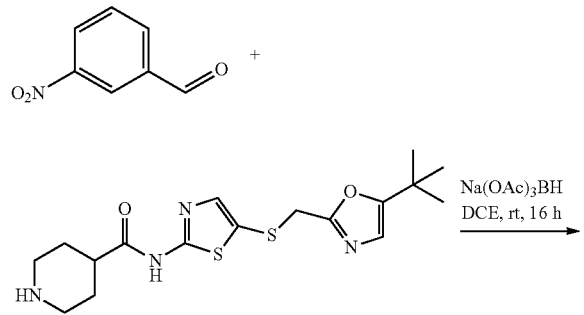

by TLC. The reaction mixture was quenched with saturated NH₄Cl solution and extracted with ethyl acetate (2×20 mL). The combined organic solvents were dried over Na₂SO₄ and concentrated under vacuum to afford the title compound (250 mg, yield 73%) as a brown sticky liquid. The crude compound was used in the next step without further purification. $^1$H NMR (DMSO-$d_6$, 400 MHz): δ 12.23 (s, 1H), 8.11-8.16 (m, 2H), 7.78 (d, J=7.63 Hz, 1H), 7.64 (t, J=7.87 Hz, 1H), 7.38 (s, 1H), 6.71 (s, 1H), 4.05 (s, 2H), 3.61 (s, 2H), 2.85 (d, J=11.44 Hz, 2H), 2.44-2.46 (m, 1H), 1.97-2.07 (m, 2H), 1.73-1.80 (m, 2H), 1.60-1.70 (m, 2H), 1.17 (s, 9H). LCMS: [M+H]$^+$=516.22; $R_f$=3.24 min.

1-(3-Aminobenzyl)-N-(5-(((5-(tert-butyl)oxazol-2-yl)methyl)thio)thiazol-2-yl)piperidine-4-carboxamide

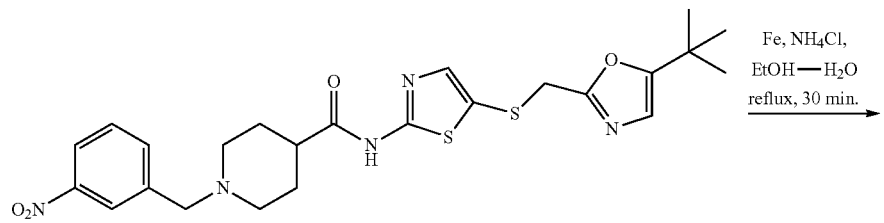

-continued

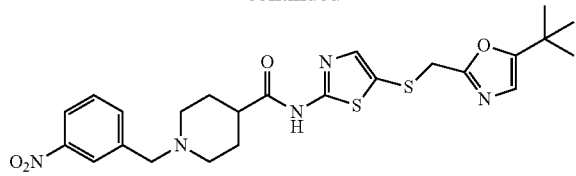

To a solution of 3-nitrobenzaldehyde (100 mg, 0.66 mmol) and N-(5-(((5-(tert-butyl)oxazol-2-yl)methyl)thio)thiazol-2-yl)piperidine-4-carboxamide (252 mg, 0.66 mmol) in DCE (20 mL) was added sodium triacetoxy borohydride (410 mg, 1.98 mmol) portion wise and stirred at room temperature for 16 h. The reaction progress was monitored To a solution of N-(5-(((5-(tert-butyl)oxazol-2-yl)methyl)thio)thiazol-2-yl)-1-(3-nitrobenzyl)piperidine-4-carboxamide (245 mg, 0.47 mmol) in EtOH:H₂O (5:2, 7 mL) was added iron powder (213 mg, 3.80 mmol) and ammonium chloride (25 mg, 0.47 mmol) at room temperature and the mixture was refluxed for 30 min. The completion of the reaction was monitored by TLC. The reaction mixture was filtered through a pad of celite, and the filtrate was concentrated under vacuum to obtain crude residue. The residue was dissolved in ethyl acetate (20 mL) and washed with water (2×10 mL). The combined organic solvents were dried over Na₂SO₄ and concentrated under vacuum to afford the title compound (190 mg, yield 83%) as a light brown solid which was used directly in the next step without further purification. LCMS: [M+H]$^+$=486.25; $R_f$=2.96 min (E)-N-(5-(((5-(tert-butyl)oxazol-2-yl)methyl)thio)thiazol-2-yl)-1-(3-(4-(dimethylamino)but-2-enamido)benzyl)piperidine-4-carboxamide

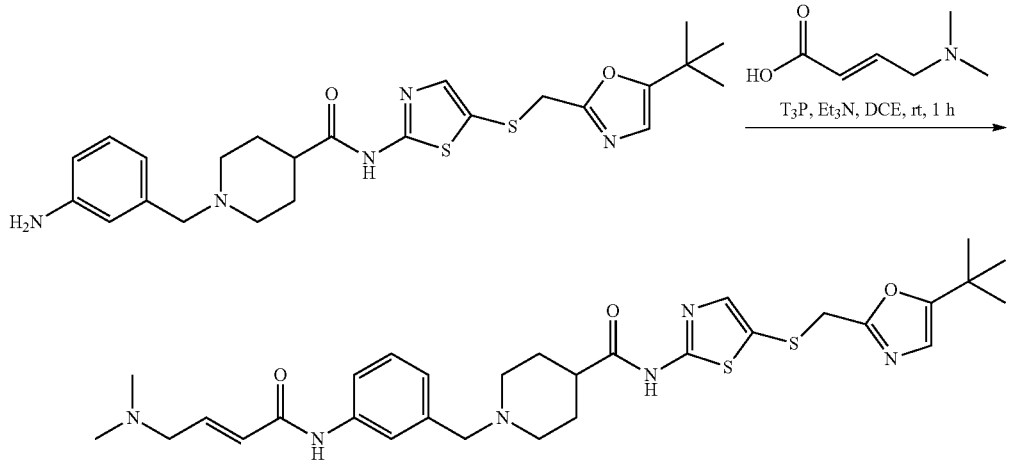

To a solution of 1-(3-aminobenzyl)-N-(5-(((5-(tert-butyl)oxazol-2-yl)methyl) thio)thiazol-2-yl)piperidine-4-carboxamide (190 mg, 0.39 mmol) and (E)-4-(dimethylamino)but-2-enoic acid (50 mg, 0.39 mmol) in DCE (19 mL) was added triethyl amine (0.16 mL, 1.17 mmol) followed by 50% wt T$_3$P solution in ethyl acetate (1.9 mL, 2.98 mmol) at 0° C. and the reaction mixture was stirred at room temperature for 1 h. The reaction progress was monitored by TLC. The reaction mixture was diluted with DCM (20 mL) and washed with water (2×10 mL). The combined organic solvents were dried over Na$_2$SO$_4$ and concentrated under reduced pressure. The residue was purified by preparative HPLC to afford the title compound (11 mg, yield 5%) as an off white solid. $^1$H NMR (CD$_3$OD, 400 MHz): δ 8.49 (br. s, 1H), 7.72 (br. s, 1H), 7.55 (d, J=7.34 Hz, 1H), 7.31-7.36 (m, 2H), 7.15 (d, J=7.34 Hz, 1H), 6.85-6.95 (m, 1H), 6.67 (s, 1H), 6.36 (d, J=15.16 Hz, 1H), 3.98 (s, 2H), 3.71 (s, 2H), 3.43 (d, J=6.36 Hz, 2H), 3.11 (d, J=11.74 Hz, 2H), 2.49 (s, 6H), 2.54 (br. s, 1H), 2.32-2.36 (m, 2H), 1.90 (d, J=4.89 Hz, 4H), 1.24 (s, 9H). LCMS: [M+H]$^+$=597.21; R$_t$=2.99 min.

Example 16: N-acryloyl-N-(6-((7-(benzylamino)-3-isopropylpyrazolo[1,5-a]pyrimidin-5-yl)amino)hexyl)acrylamide (Compound 100)

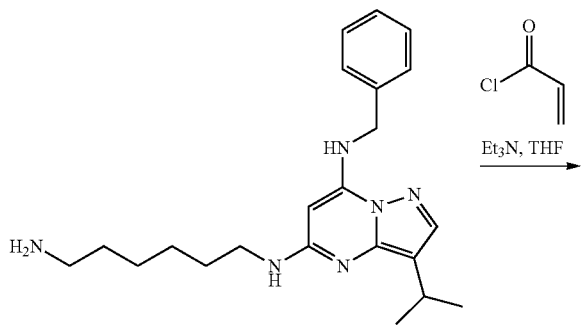

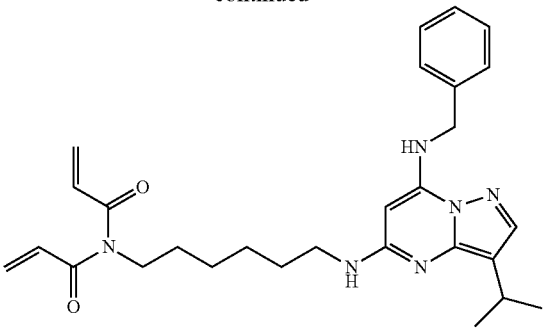

-continued

N5-(6-aminohexyl)-N7-benzyl-3-isopropylpyrazolo[1,5-a]pyrimidine-5,7-diamine (6 mg, 0.014 mmol) was dissolved in tetrahydrofuran (2.8 mL), followed by addition of triethylamine (63 μL, 0.44 mmol) and acryloyl chloride (0.14 μL, 0.17 mmol). The reaction was stirred at room temperature for 16 h. Upon completion, the reaction mixture was poured into sat. NaHCO$_3$ (10 mL) and extracted with dichloromethane (10 mL×3). The combined organics were dried over Na$_2$SO$_4$, filtered, and concentrated. The crude residue was purified by silica gel chromatography (0-15% methanol/dichloromethane) to afford the title compound (0.6 mg, yield 0.9%). LCMS: [M+H]$^+$=489.30; R$_t$=2.74 min.

Example 17: CDK7 Kinase Activity

Compounds of the invention were assayed for CDK7 activity at Life Technologies (Grand Island, N.Y.) using their commercially available Adapta® kinase assay services. Test compounds were tested at concentrations ranging from 10 μM down to 0.514 nM in a series of 3-fold serial dilutions. Details of this assay, including substrates used, are available on the Life Technologies web site (http://www.lifetechnologies.com/us/en/home/life-science/drug-discovery/target-and-lead-identification-and-validation/kinasebiology/kinase-activity-assays.html). The results of the assay are shown below in Table 2, where "A" represents a calculated IC$_{50}$ of less than 100 nM; "B" represents a calculated IC$_{50}$ of between 100 nM and 1 µM; and "C" represents a calculated $IC_{50}$ of greater than 1 µM.

TABLE 2

CDK7 Inhibitory Activity of Selected Compounds of the Invention.

| Compound No. | CDK7 Inhibition ($IC_{50}$) |
|---|---|
| 100 | C |
| 102 | C |
| 103 | B |
| 104 | A |
| 105 | A |
| 116 | B |
| 117 | C |
| 118 | B |
| 119 | B |
| 120 | C |
| 121 | B |
| 122 | C |
| 123 | C |
| 124 | C |
| 125 | B |
| 127 | B |

Example 18: Inhibition of A637 Cell Proliferation

Representative compounds of the invention were tested at different concentrations (from 4 µM to 126.4 pM; 0.5 log serial dilutions) for their ability to inhibit the proliferation of A673 cells. Known CDK inhibitors flavopiridol and triptolide were used as positive controls. Cells were grown in Dulbecco's Modified Eagle's Medium, +10% FBS+1 mM Sodium Pyruvate. The cells were cultured at 37° C. in a humidified chamber in the presence of 5% $CO_2$. Proliferation assays were conducted over a 72 hour time period. CyQUANT® (Life Technologies, Chicago, Ill. USA) was used to assess the anti-proliferative effects of the compounds following manufacturer's directions and utilizing the reagents supplied with the CyQUANT® kit. The results of the assay are shown below in Table 3, where "A" represents an $IC_{50}$ of less than 500 nM; "B" an $IC_{50}$ of between 500 nM and 5 µM; and "C" an $IC_{50}$ of greater than 5 µM.

TABLE 3

Inhibition of Proliferation of A673 Cells by Compounds of the Invention.

| Compound No. | A673 $IC_{50}$ |
|---|---|
| 102 | B |
| 103 | B |
| 104 | A |
| 105 | A |
| 117 | A |
| 118 | A |
| 119 | A |
| 120 | A |
| 121 | A |
| 122 | A |
| 123 | A |
| 124 | A |
| 125 | A |
| 127 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound having the structural formula (IIIc):

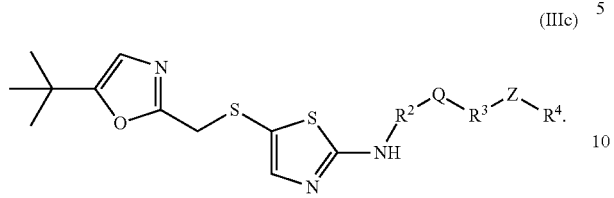
(IIIc)

or a pharmaceutically acceptable salt thereof, wherein:
$R^2$ is —C(O)—;
Q is

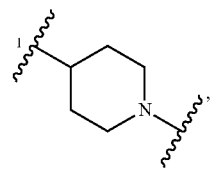 [SMILES: *C1CCN(*)CC1]

wherein "1" represents a point of attachment to $R^2$;
$R^3$ is a bond, optionally substituted —CH$_2$—, optionally substituted —NH—, —C(O), —N(CH$_3$)—, or optionally substituted —CH(CH$_3$)—;
Z is a monocyclic or bicyclic aryl, carbocyclyl, heterocyclyl, or heteroaryl, wherein Z is optionally substituted;
$R^4$ is

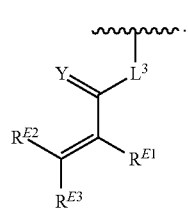
(ii-1)

wherein $L^3$ is a bond, an optionally substituted $C_1$-$C_7$ alkylene, or an optionally substituted $C_2$-$C_7$ alkenylene or alkynylene, wherein one or more methylene units of the alkylene, alkenylene or alkynylene are optionally and independently replaced with —O—, —S—, —S(O)—, —S(O)$_2$, —N— or —N(R$^6$)—;
Y is O, S, or N(R$^6$);
each $R^6$ is independently selected from hydrogen and optionally substituted —C$_1$-C$_6$ alkyl; and
each of $R^{E1}$, $R^{E2}$ and $R^{E3}$ is independently selected from hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CH$_2$OR$^9$, —CH$_2$N(R$^9$)$_2$, —CH$_2$SR$^9$, —CN, —OR$^9$, —N(R$^9$)$_2$, and —SR$^9$, wherein each occurrence of $R^9$ is independently selected from hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or
$R^{E1}$ and $R^{E3}$, or $R^{E2}$ and $R^{E3}$, or $R^{E1}$ and $R^{E2}$ are joined to form an optionally substituted carbocyclic or optionally substituted heterocyclic ring.

2. The compound of claim 1, wherein the compound is:

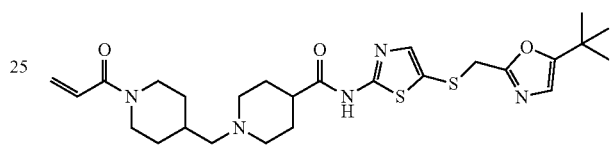

or a pharmaceutically acceptable salt thereof,

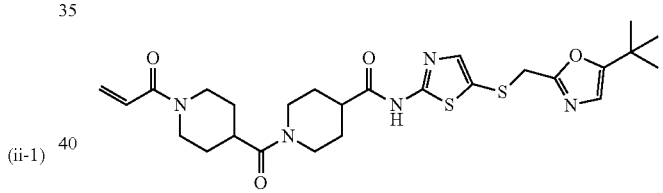

or a pharmaceutically acceptable salt thereof,

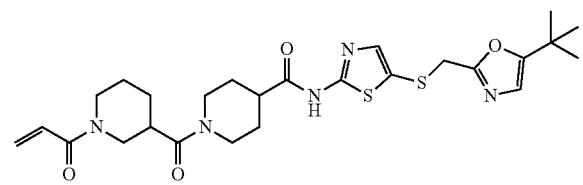 [SMILES: C=CC(=O)N1CCCC(C(=O)N2CCC(C(=O)Nc3ncc(SCc4ncc(C(C)(C)C)o4)s3)CC2)C1]

or a pharmaceutically acceptable salt thereof,

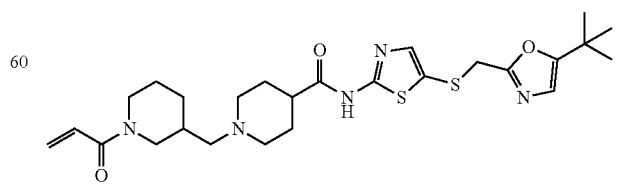

or a pharmaceutically acceptable salt thereof,

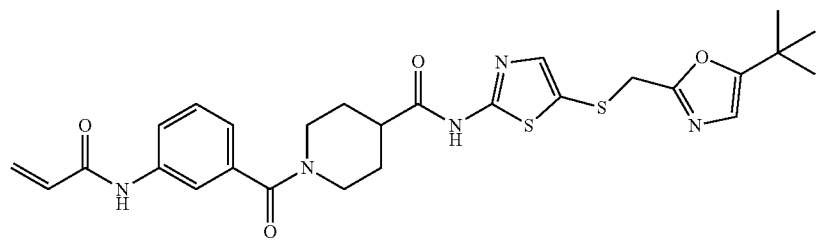 [SMILES: C=CC(=O)Nc1cccc(C(=O)N2CCC(C(=O)Nc3ncc(SCc4ncc(C(C)(C)C)o4)s3)CC2)c1]
or a pharmaceutically acceptable salt thereof,
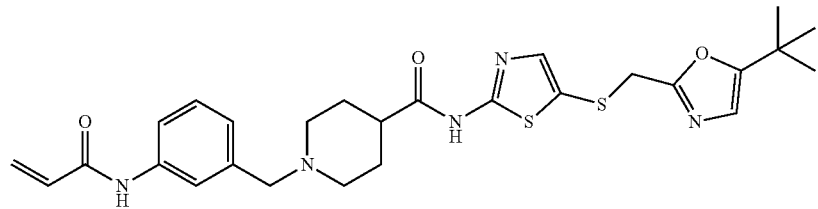 [SMILES: C=CC(=O)Nc1cccc(CN2CCC(C(=O)Nc3ncc(SCc4ncc(C(C)(C)C)o4)s3)CC2)c1]
or a pharmaceutically acceptable salt thereof,
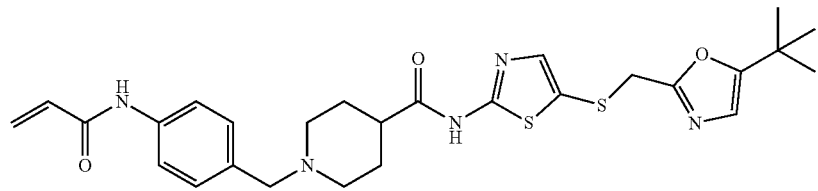 [SMILES: C=CC(=O)Nc1ccc(CN2CCC(C(=O)Nc3ncc(SCc4ncc(C(C)(C)C)o4)s3)CC2)cc1]
or a pharmaceutically acceptable salt thereof,
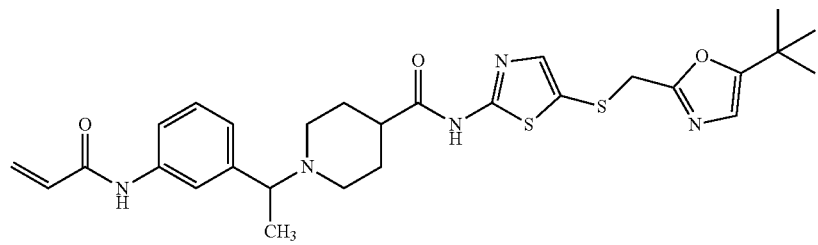 [SMILES: C=CC(=O)Nc1cccc(C(C)N2CCC(C(=O)Nc3ncc(SCc4ncc(C(C)(C)C)o4)s3)CC2)c1]
or a pharmaceutically acceptable salt thereof,
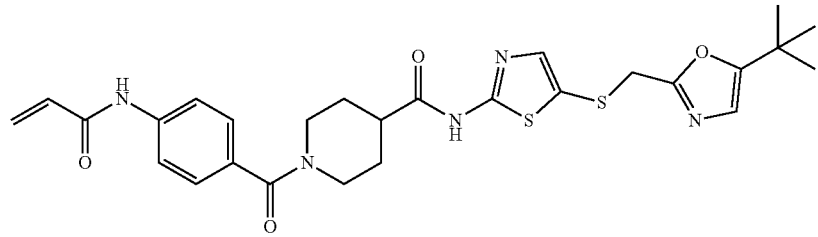 [SMILES: C=CC(=O)Nc1ccc(C(=O)N2CCC(C(=O)Nc3ncc(SCc4ncc(C(C)(C)C)o4)s3)CC2)cc1]
or a pharmaceutically acceptable salt thereof, or

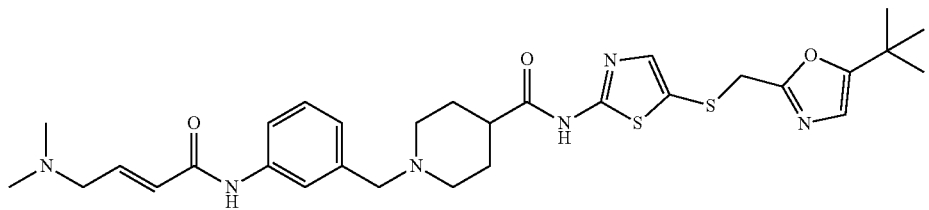 [SMILES: CN(C)C/C=C/C(=O)Nc1cccc(CN2CCC(C(=O)Nc3ncc(SCc4ncc(C(C)(C)C)o4)s3)CC2)c1]
or a pharmaceutically acceptable salt salt thereof.
3. The compound of claim 2, wherein the compound is
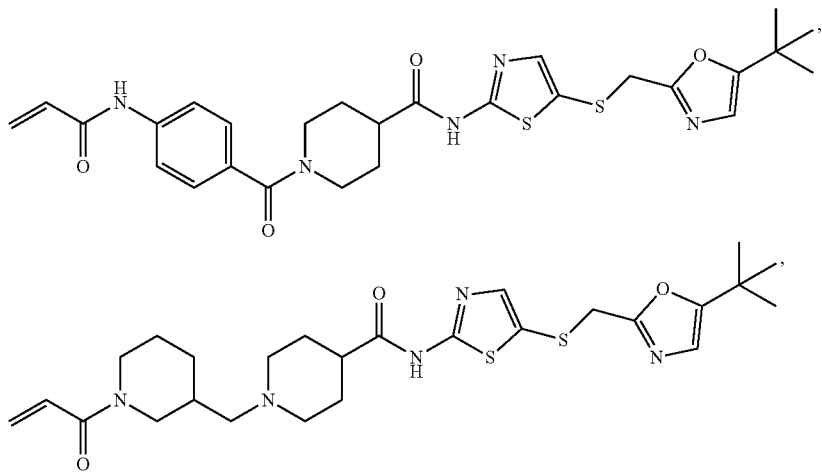
or a pharmaceutically acceptable salt of either compound.
4. The compound of claim 1, wherein Z is selected from
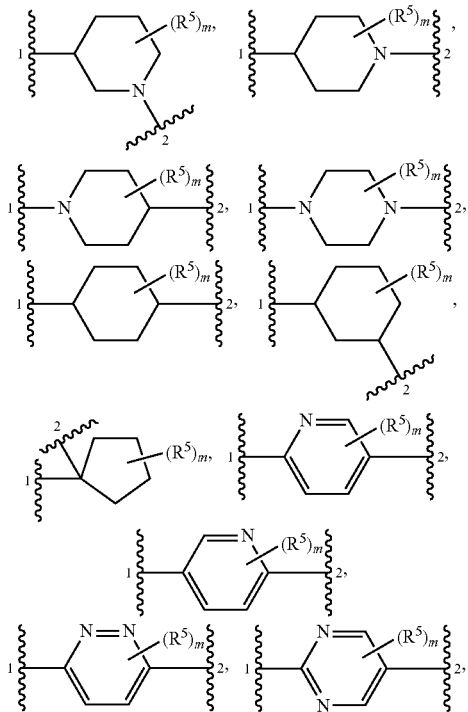
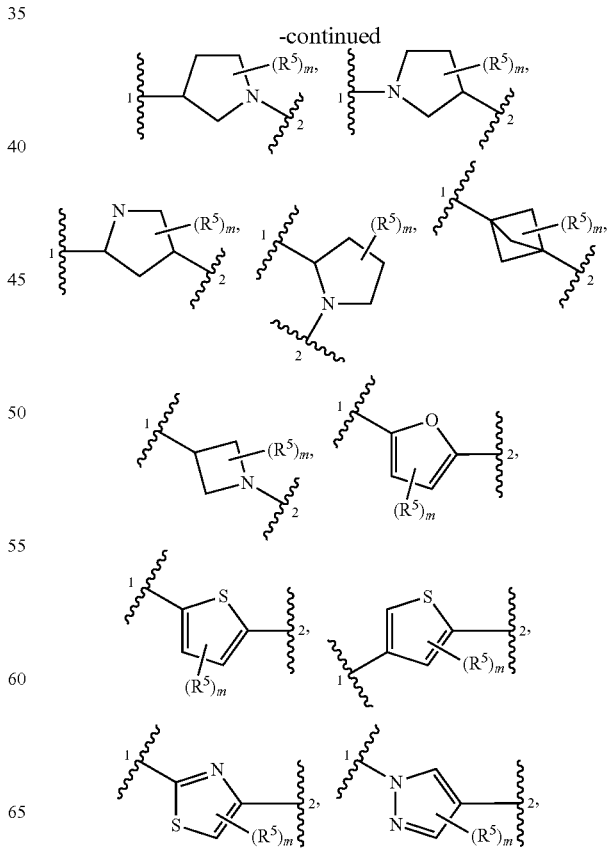

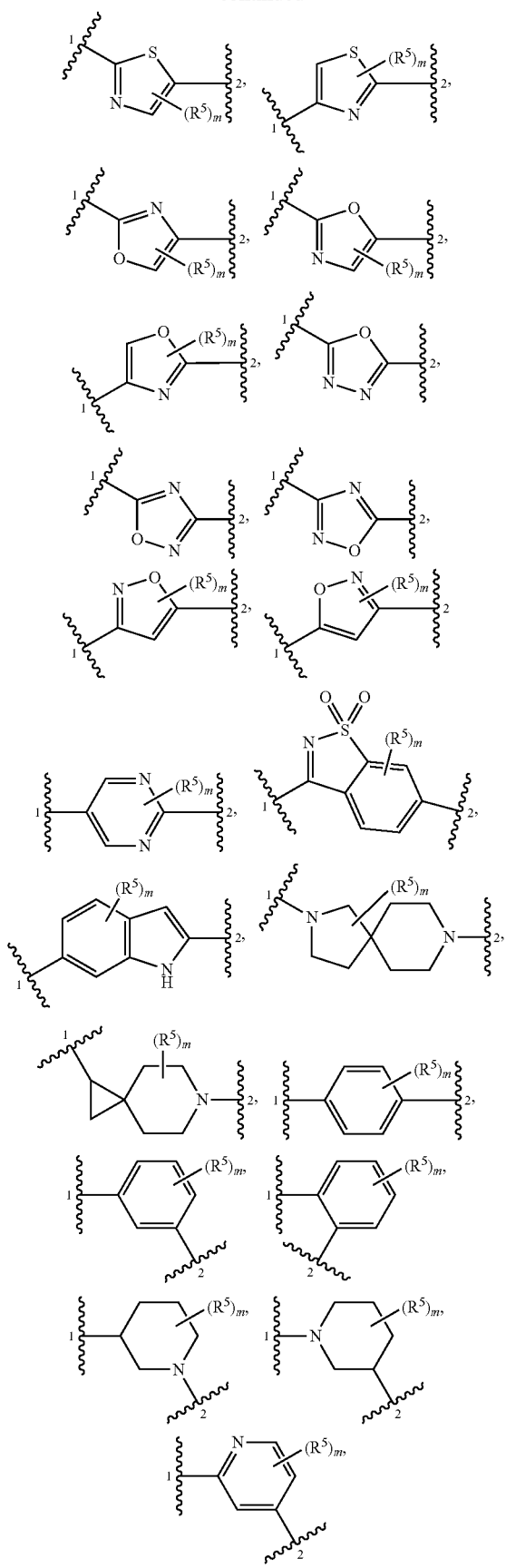

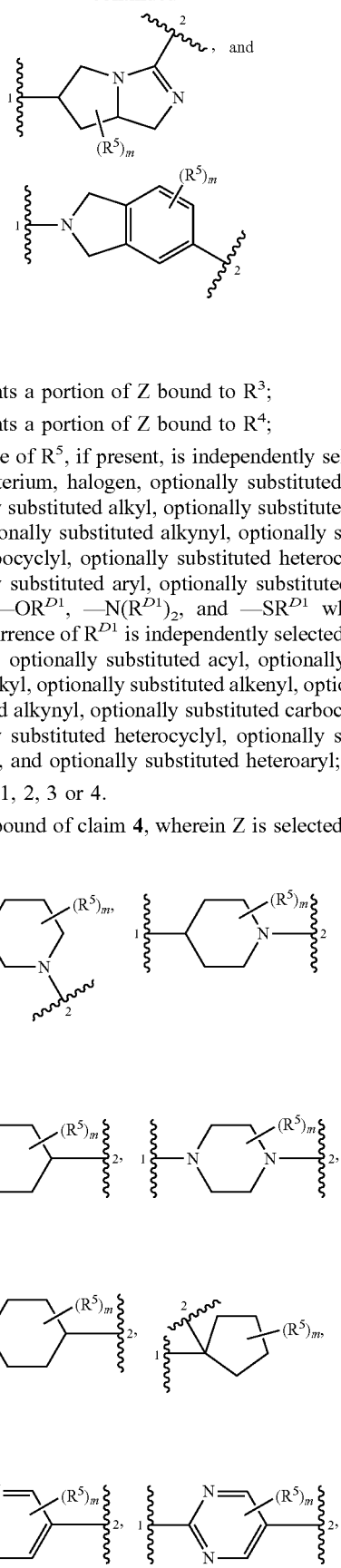

wherein:

"1" represents a portion of Z bound to $R^3$;

"2" represents a portion of Z bound to $R^4$;

each instance of $R^5$, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1})_2$, and $-SR^{D1}$ wherein each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

and m is 0, 1, 2, 3 or 4.

5. The compound of claim 4, wherein Z is selected from

-continued

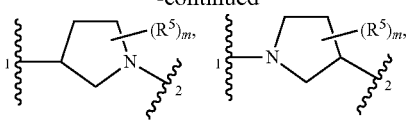

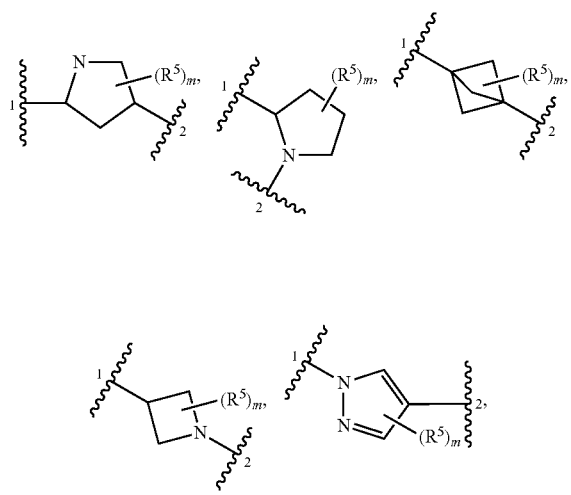

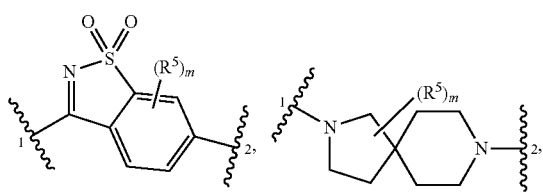

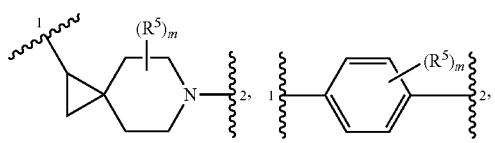

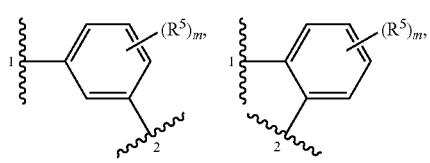

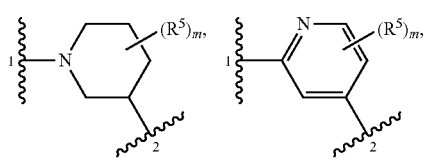

-continued

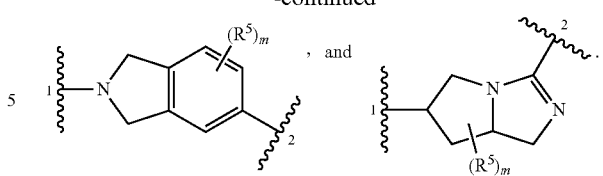, and

6. The compound of claim 1, wherein $L^3$ is selected from a bond, —NH—, —CH$_2$—NH—, —S(O)$_2$—NH—, and —NH—S(O)$_2$—NH—, wherein "" represents a portion of $L^3$ bound to —C(=Y)—.

7. The compound of claim 1, wherein $R^4$ is selected from: —CH$_2$—NH—C(O)—CH=CH—CH$_2$—N(CH$_3$)$_2$, —NH—C(O)—CH=CH—CH$_2$—N(CH$_3$)$_2$, —C(O)—CH=CH—CH$_2$—N(CH$_3$)$_2$, —NH—C(O)—CH=CH$_2$, —C(O)—CH=CH$_2$, —S(O)$_2$—NH—C(O)—CH=CH$_2$, and —NH—S(O)$_2$—NH—C(O)—CH=CH$_2$—NH—C(O)—CH=CH$_2$.

8. A pharmaceutical composition comprising a compound of claim 1 and a pharmaceutically acceptable excipient.

9. The pharmaceutical composition of claim 8, wherein the compound is

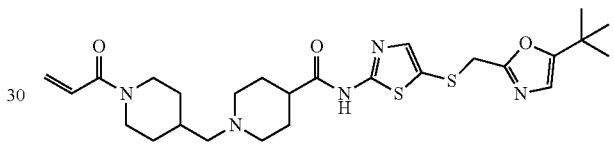

or a pharmaceutically acceptable salt thereof,

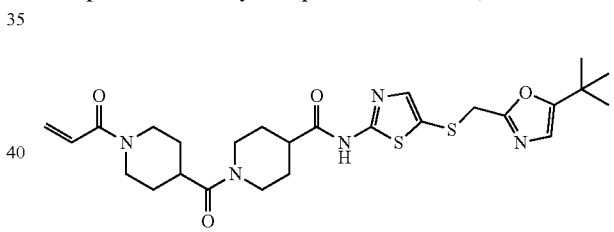

or a pharmaceutically acceptable salt thereof,

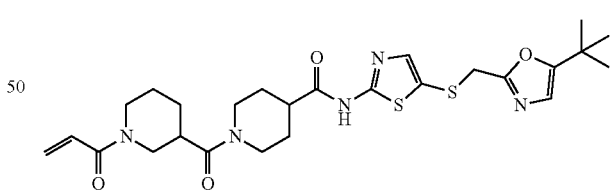

or a pharmaceutically acceptable salt thereof,

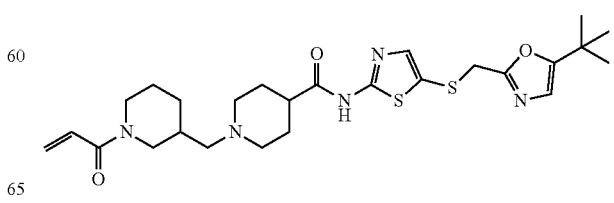

or a pharmaceutically acceptable salt thereof,

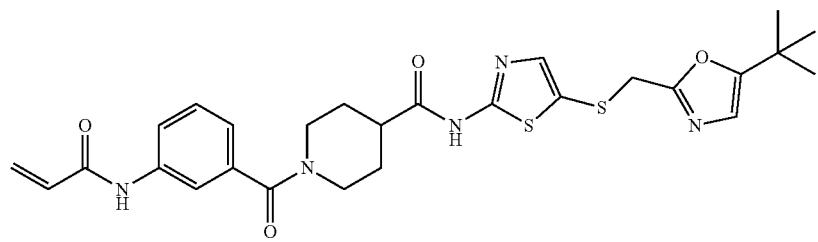 [SMILES: C=CC(=O)Nc1cccc(C(=O)N2CCC(C(=O)Nc3ncc(SCc4ncc(C(C)(C)C)o4)s3)CC2)c1]
or a pharmaceutically acceptable salt thereof,
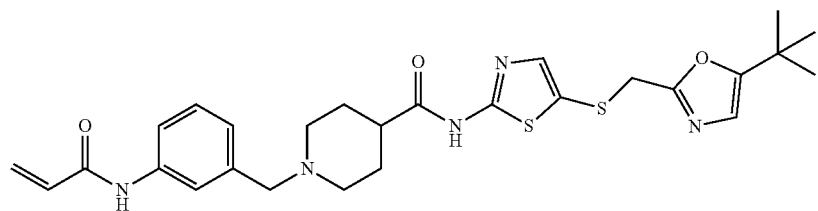 [SMILES: C=CC(=O)Nc1cccc(CN2CCC(C(=O)Nc3ncc(SCc4ncc(C(C)(C)C)o4)s3)CC2)c1]
or a pharmaceutically acceptable salt thereof,
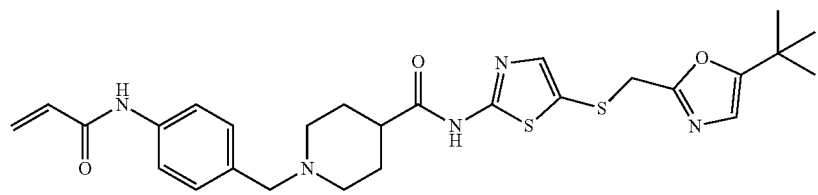 [SMILES: C=CC(=O)Nc1ccc(CN2CCC(C(=O)Nc3ncc(SCc4ncc(C(C)(C)C)o4)s3)CC2)cc1]
or a pharmaceutically acceptable salt thereof,
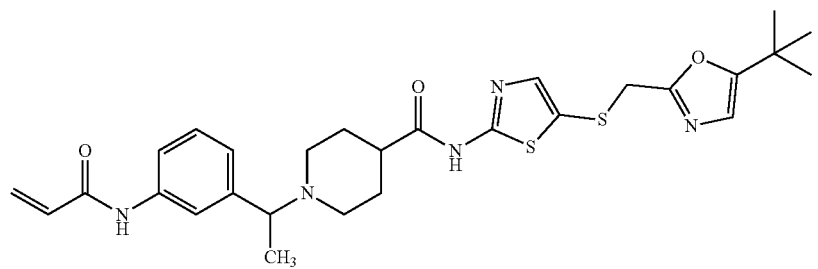 [SMILES: C=CC(=O)Nc1cccc(C(C)N2CCC(C(=O)Nc3ncc(SCc4ncc(C(C)(C)C)o4)s3)CC2)c1]
or a pharmaceutically acceptable salt thereof,
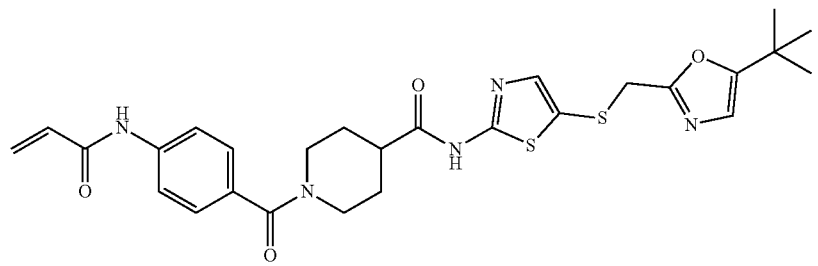 [SMILES: C=CC(=O)Nc1ccc(C(=O)N2CCC(C(=O)Nc3ncc(SCc4ncc(C(C)(C)C)o4)s3)CC2)cc1]
or a pharmaceutically acceptable salt thereof,

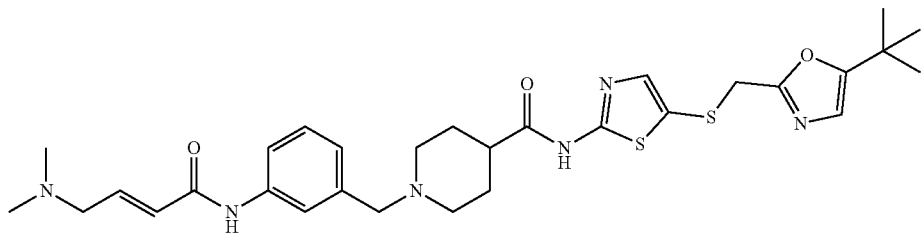 [SMILES: CN(C)C/C=C/C(=O)Nc1cccc(CN2CCC(C(=O)Nc3ncc(SCc4ncc(C(C)(C)C)o4)s3)CC2)c1]
or a pharmaceutically acceptable salt thereof.
10. The pharmaceutical composition of claim 9, wherein the compound is
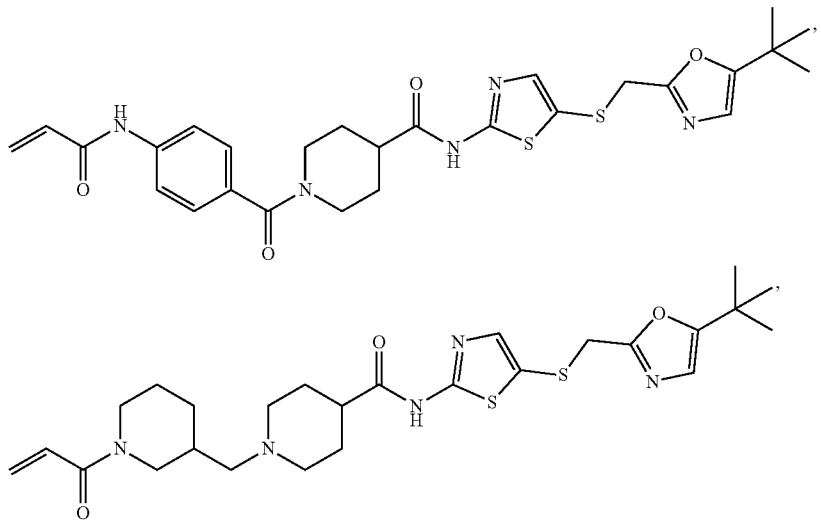
or a pharmaceutically acceptable salt of either compound.
11. The pharmaceutical composition of claim 8, wherein Z is selected from
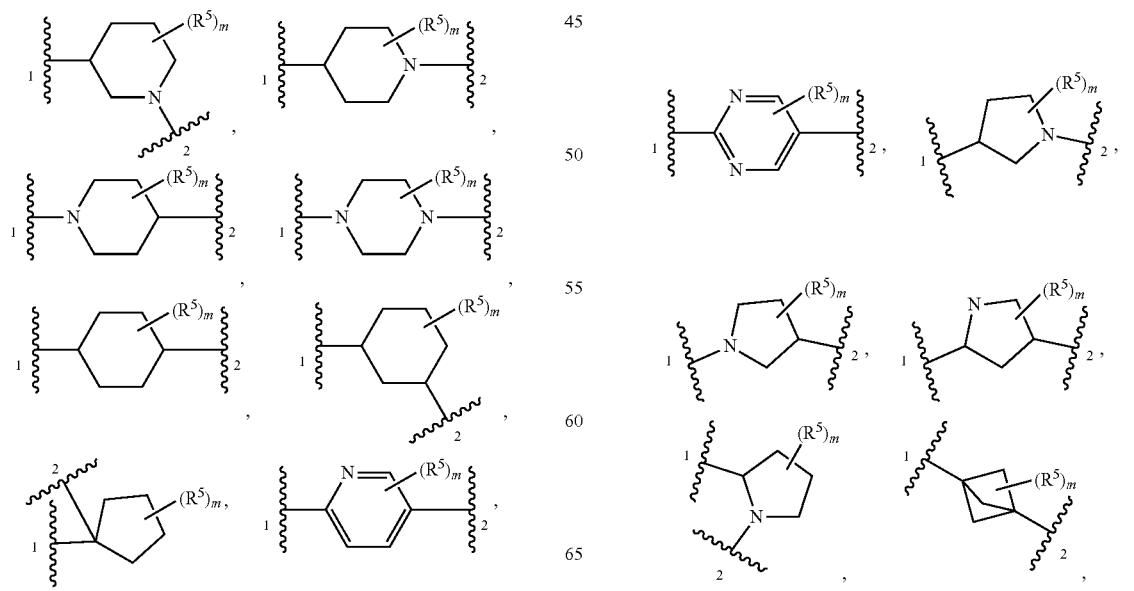

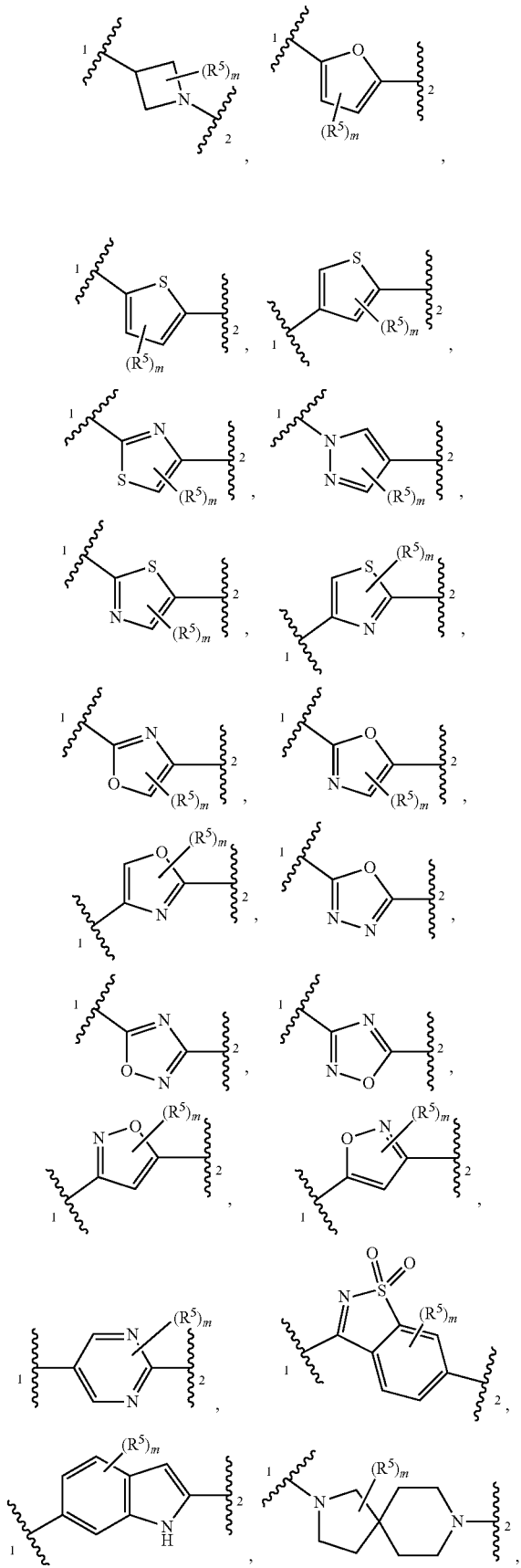

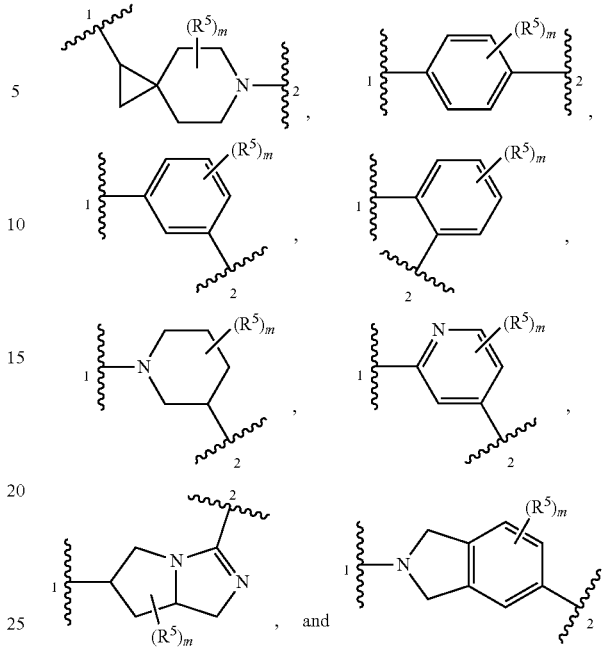

wherein:
"1" represents a portion of Z bound to $R^3$;
"2" represents a portion of Z bound to $R^4$;
each instance of $R^5$, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{D1}$, —$N(R^{D1})_2$, and —$SR^{D1}$ wherein each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;
and m is 0, 1, 2, 3 or 4.

12. The pharmaceutical composition of claim 8, wherein Z is selected from

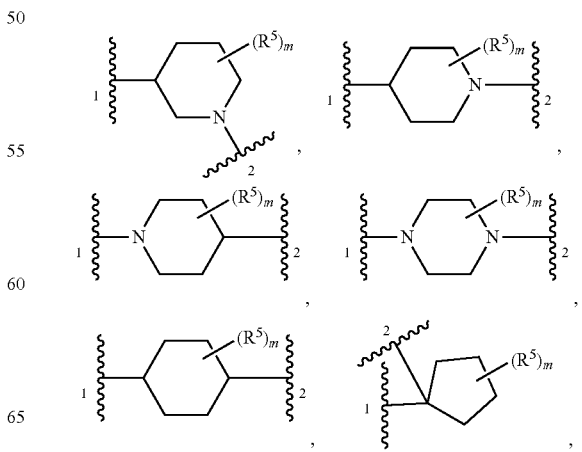

-continued

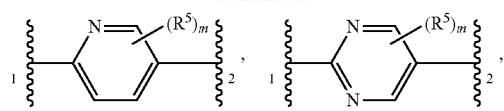

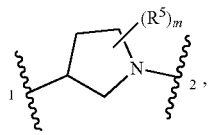, 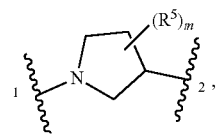,

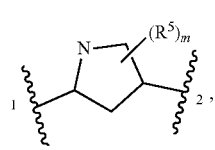, 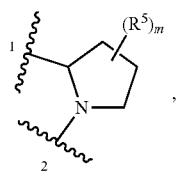,

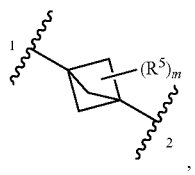, 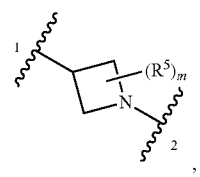,

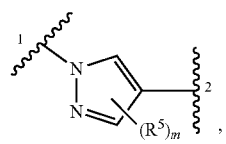, 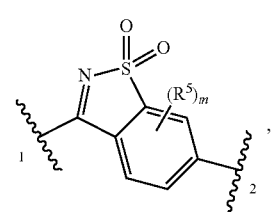,

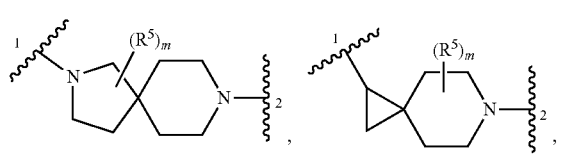,

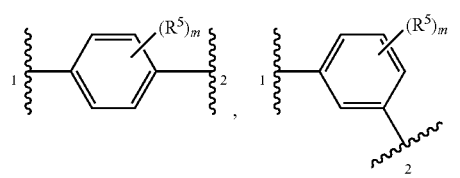,

-continued

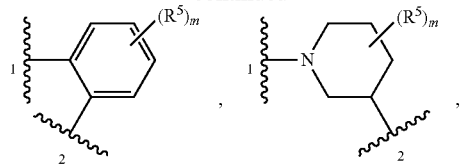

wherein:
"1" represents a portion of Z bound to $R^3$;
"2" represents a portion of Z bound to $R^4$;
each instance of $R^5$, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1})_2$, and $-SR^{D1}$, wherein each occurrence of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;
and m is 0, 1, 2, 3 or 4.

13. The pharmaceutical composition of claim 8, wherein $L^3$ is selected from a bond, $-NH-$, $-CH_2-NH-$, $-S(O)_2-NH-$, and $-NH-S(O)_2-NH-$, wherein "" represents a portion of $L^3$ bound to $-C(=Y)-$.

14. The pharmaceutical composition of claim 8, wherein $R^4$ is selected from: $-CH_2-NH-C(O)-CH=CH-CH_2-N(CH_3)_2$, $-NH-C(O)-CH=CH-CH_2-N(CH_3)_2$, $-C(O)-CH=CH-CH_2-N(CH_3)_2$, $-NH-C(O)-CH=CH_2$, $-C(O)-CH=CH_2$, $-S(O)_2-NH-C(O)-CH=CH_2$, and $-NH-S(O)_2-NH-C(O)-CH=CH_2-NH-C(O)-CH=CH_2$.

15. A method of treating a cancer selected from triple-negative breast cancer, neuroblastoma, small cell lung cancer, ovarian cancer, acute myelogenous leukemia, and Ewing's sarcoma in a subject in need thereof, the method comprising administering to the subject a therapeutically effective amount of the composition of claim 5.

16. The method of claim 15, wherein the composition comprises

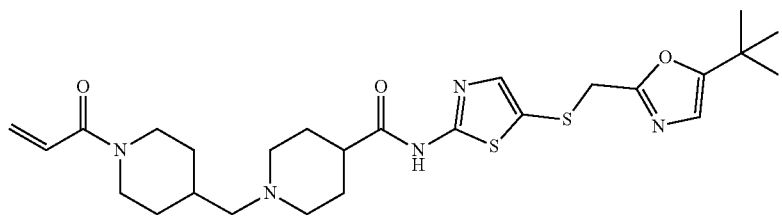 [SMILES: C=CC(=O)N1CCC(CN2CCC(C(=O)Nc3ncc(SCc4ncc(C(C)(C)C)o4)s3)CC2)CC1]
or a pharmaceutically acceptable salt thereof,
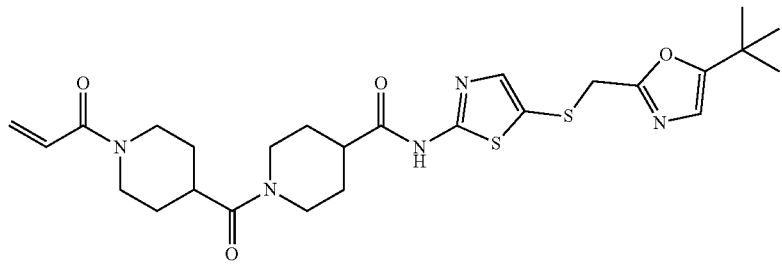 [SMILES: C=CC(=O)N1CCC(C(=O)N2CCC(C(=O)Nc3ncc(SCc4ncc(C(C)(C)C)o4)s3)CC2)CC1]
or a pharmaceutically acceptable salt thereof,
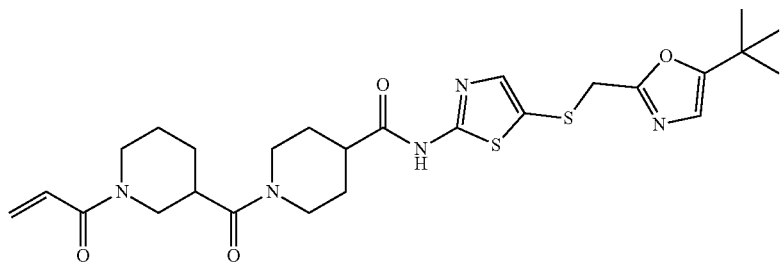 [SMILES: C=CC(=O)N1CCCC(C(=O)N2CCC(C(=O)Nc3ncc(SCc4ncc(C(C)(C)C)o4)s3)CC2)C1]
or a pharmaceutically acceptable salt thereof,
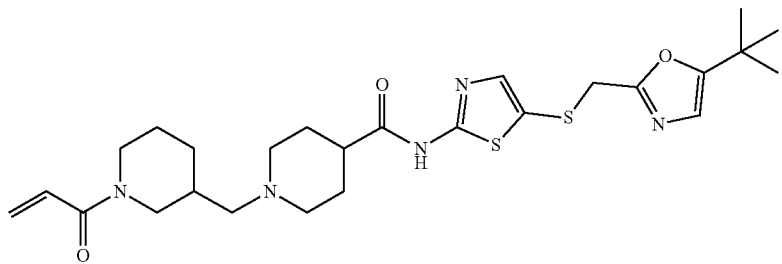 [SMILES: C=CC(=O)N1CCCC(CN2CCC(C(=O)Nc3ncc(SCc4ncc(C(C)(C)C)o4)s3)CC2)C1]
or a pharmaceutically acceptable salt thereof,
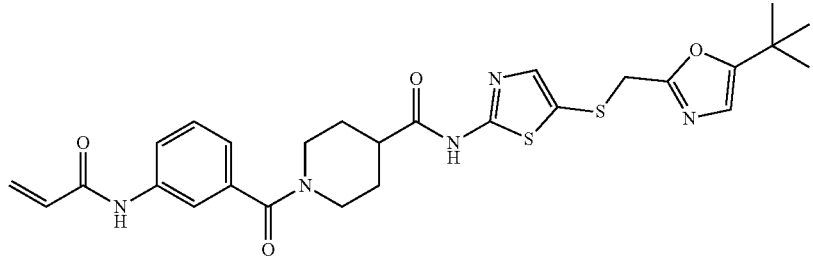 [SMILES: C=CC(=O)Nc1cccc(C(=O)N2CCC(C(=O)Nc3ncc(SCc4ncc(C(C)(C)C)o4)s3)CC2)c1]
or a pharmaceutically acceptable salt thereof,

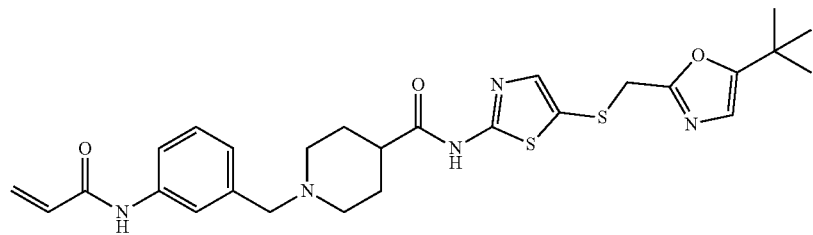 [SMILES: C=CC(=O)Nc1cccc(CN2CCC(C(=O)Nc3ncc(SCc4ncc(C(C)(C)C)o4)s3)CC2)c1]
or a pharmaceutically acceptable salt thereof,
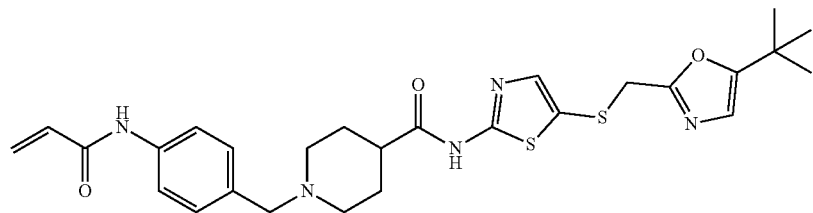 [SMILES: C=CC(=O)Nc1ccc(CN2CCC(C(=O)Nc3ncc(SCc4ncc(C(C)(C)C)o4)s3)CC2)cc1]
or a pharmaceutically acceptable salt thereof,
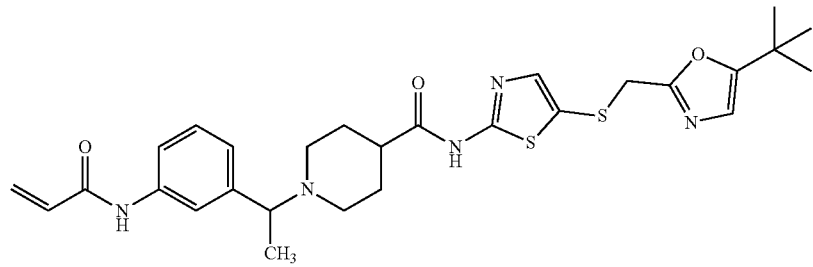 [SMILES: C=CC(=O)Nc1cccc(C(C)N2CCC(C(=O)Nc3ncc(SCc4ncc(C(C)(C)C)o4)s3)CC2)c1]
or a pharmaceutically acceptable salt thereof,
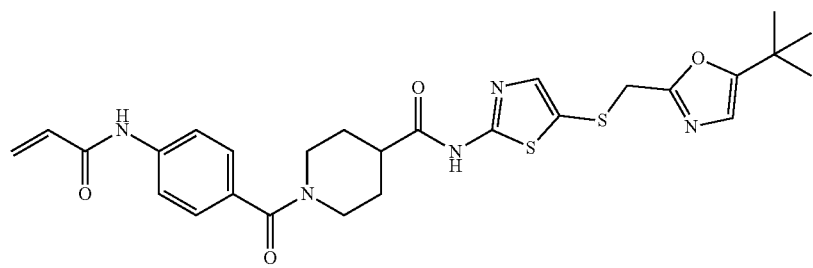 [SMILES: C=CC(=O)Nc1ccc(C(=O)N2CCC(C(=O)Nc3ncc(SCc4ncc(C(C)(C)C)o4)s3)CC2)cc1]
or a pharmaceutically acceptable salt thereof,
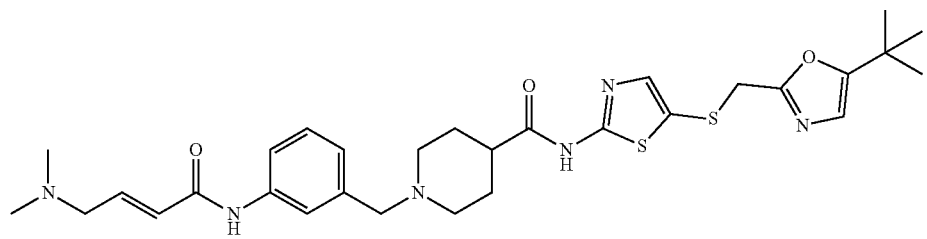 [SMILES: CN(C)C/C=C/C(=O)Nc1cccc(CN2CCC(C(=O)Nc3ncc(SCc4ncc(C(C)(C)C)o4)s3)CC2)c1]
or a pharmaceutically acceptable salt thereof.

17. The method of claim 16, wherein the composition comprises
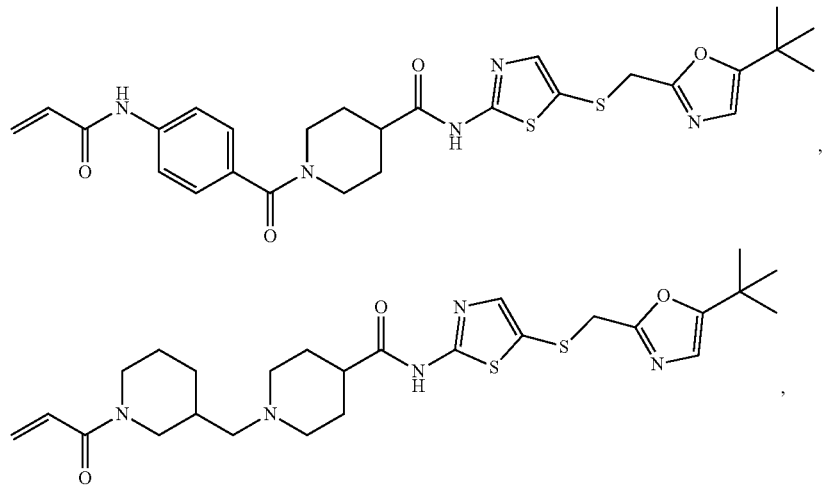
or a pharmaceutically acceptable salt of either compound.
18. The method of claim 15, wherein Z is selected from
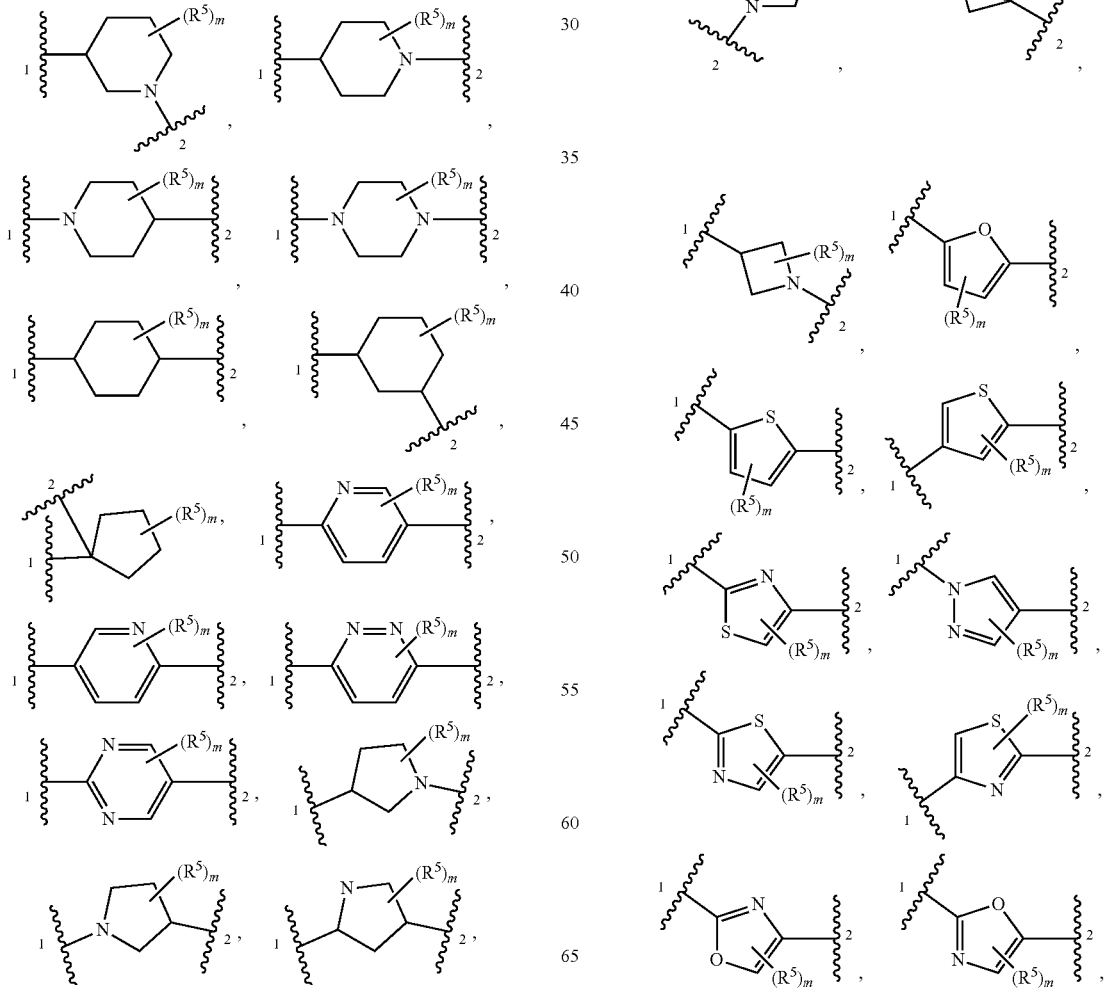

-continued

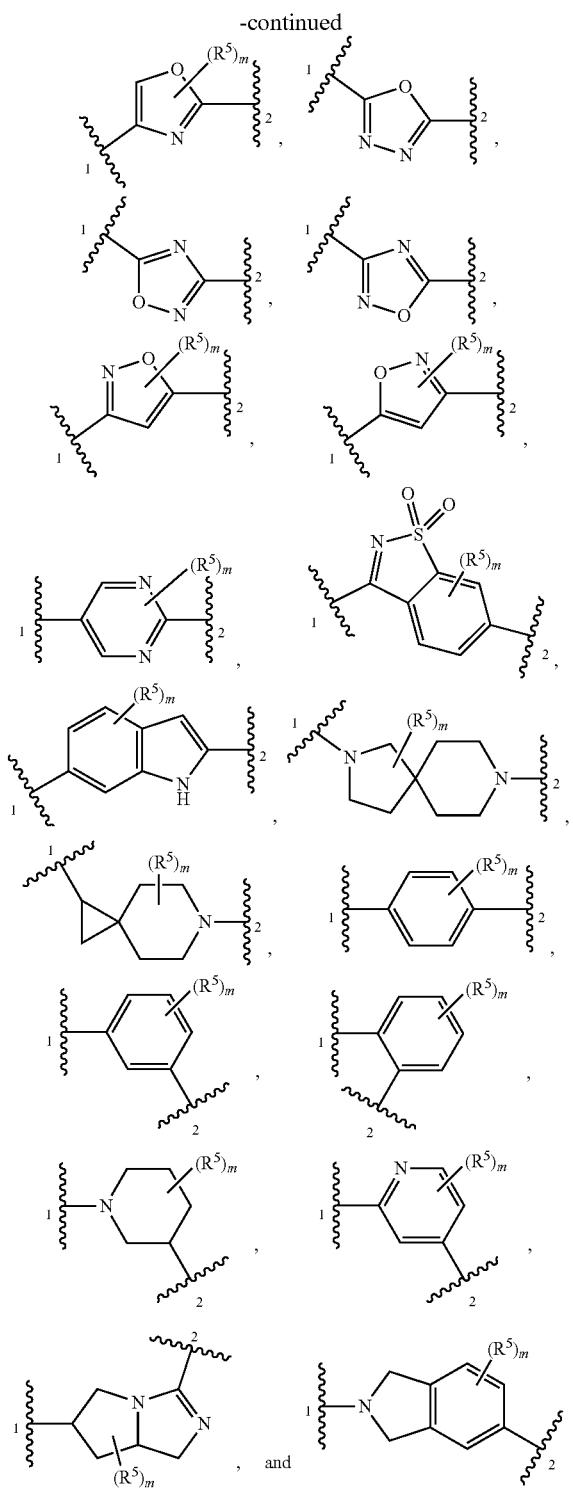

, and wherein:
"1" represents a portion of Z bound to R³;
"2" represents a portion of Z bound to R⁴;
each instance of R⁵, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$)$_2$, and —SR$^{D1}$ wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

and m is 0, 1, 2, 3 or 4.

19. The method of claim 15, wherein Z is selected from

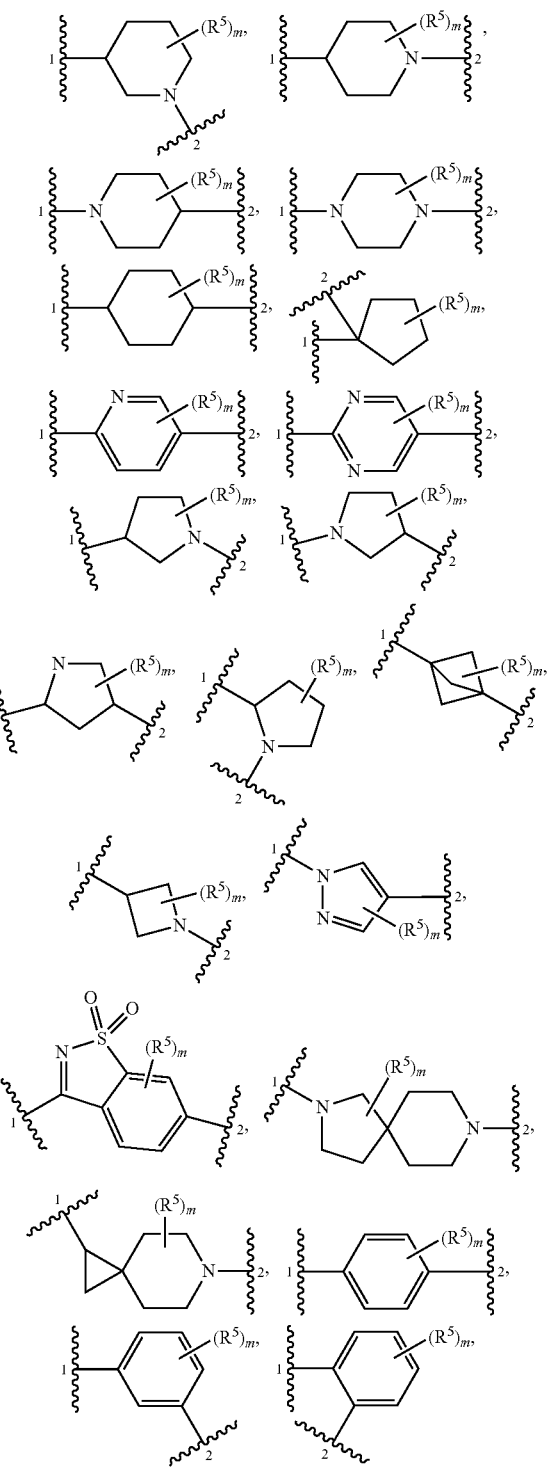

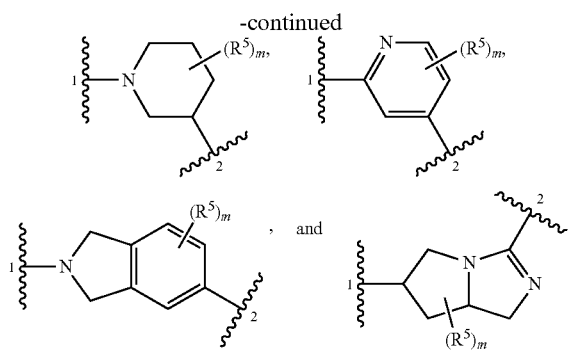

wherein:
"1" represents a portion of Z bound to R³;
"2" represents a portion of Z bound to R⁴;
each instance of R⁵, if present, is independently selected from deuterium, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1}$), and —SR$^{D1}$, wherein each occurrence of R$^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;
and m is 0, 1, 2, 3 or 4.

20. The method of claim 15, wherein L³ is selected from a bond, —NH—, —CH₂—NH—, —S(O)₂—NH—, and —NH—S(O)₂—NH—, wherein "" represents a portion of L³ bound to —C(=Y)—.

21. The method of claim 15, wherein R⁴ is selected from: —CH₂—NH—C(O)—CH=CH—CH₂—N(CH₃)₂, —NH—C(O)—CH=CH—CH₂—N(CH₃)₂, —C(O)—CH=CH—CH₂—N(CH₃)₂, —NH—C(O)—CH=CH₂, —C(O)—CH=CH₂, —S(O)₂—NH—C(O)—CH=CH₂, and —NH—S(O)₂—NH—C(O)—CH=CH₂—NH—C(O)—CH=CH₂.

* * * * *